United States Patent [19]

Harada et al.

[11] Patent Number: 4,729,381

[45] Date of Patent: Mar. 8, 1988

[54] LIVING BODY INFORMATION RECORDER

[75] Inventors: Chikao Harada, Nagoya; Masami Goto, Aichi, both of Japan

[73] Assignee: Nippon Colin Co., Ltd., Japan

[21] Appl. No.: 10,788

[22] Filed: Feb. 4, 1987

[30] Foreign Application Priority Data

| Feb. 4, 1986 | [JP] | Japan | 61-22424 |
| Feb. 4, 1986 | [JP] | Japan | 61-22425 |
| Feb. 6, 1986 | [JP] | Japan | 61-24568 |
| Feb. 6, 1986 | [JP] | Japan | 61-24569 |
| Feb. 6, 1986 | [JP] | Japan | 61-24570 |
| Feb. 6, 1986 | [JP] | Japan | 61-24571 |
| Feb. 10, 1986 | [JP] | Japan | 61-27632 |
| Feb. 26, 1986 | [JP] | Japan | 61-40983 |

[51] Int. Cl.⁴ .............................. A61B 5/02; A61B 5/04
[52] U.S. Cl. ..................................... 128/671; 128/700; 128/710; 128/712; 346/33 ME; 364/415
[58] Field of Search ............................... 128/670-671, 128/698, 710, 700, 712; 346/33 ME; 364/413, 415, 417

[56] References Cited

U.S. PATENT DOCUMENTS

| 4,085,407 | 4/1978 | Stratbucker et al. | 346/33 ME |
| 4,281,330 | 7/1981 | Warrick | 346/33 ME X |
| 4,513,294 | 4/1985 | Anderson et al. | 346/33 ME |
| 4,513,295 | 4/1985 | Jones et al. | 128/698 X |

Primary Examiner—Edward M. Coven
Assistant Examiner—Angela D. Sykes
Attorney, Agent, or Firm—Parkhurst & Oliff

[57] ABSTRACT

An apparatus for effecting automatic repetitive detection of items of living body information, such as blood pressure, heart rate and breathing rate, and for automatically recording the detected living body information in a predetermined two dimensional chart area provided on an anesthesia record sheet, by recording respective indicia representative of the living body information, at respective recording positions in the chart area, which corresponds to times of detection of the living body information, including: (A) a sensing device for detecting the living body information; (B) a recording device having a support for supporting the record sheet so as to permit manual recording of auxiliary information other than the living body information on the record sheet, and further having a recording member(s) movable relative to the record sheet for recording the indicia in the chart area; and (C) a control device, responsive to the sensing device, for determining the recording positions of the indicia based on the detected living body information and the times of detection of the living body information, and for controlling the recording device so as to record the indicia at the determined recording positions in the chart area.

26 Claims, 57 Drawing Figures

FIG. 57
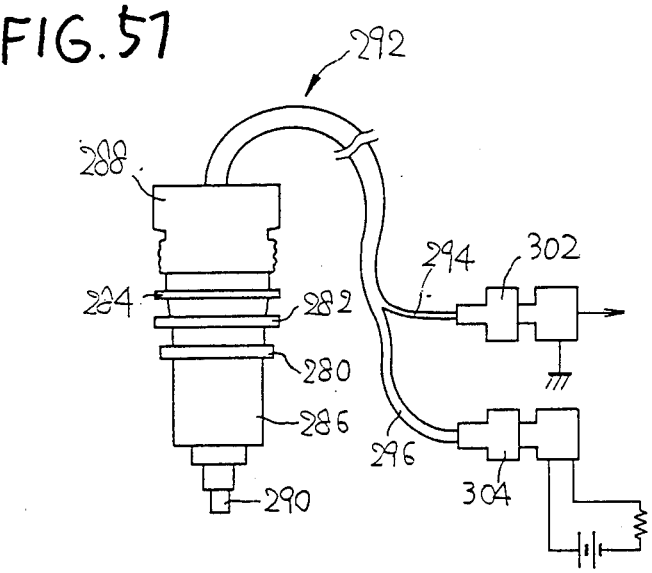
FIG. 52
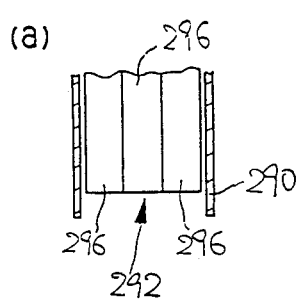
FIG. 53
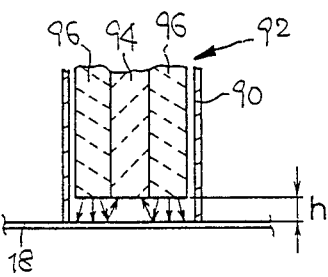
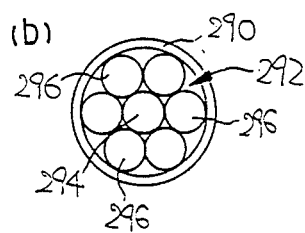
FIG. 56
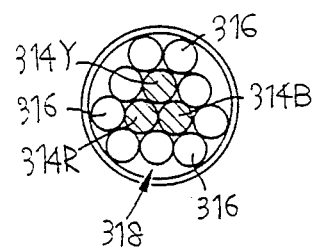

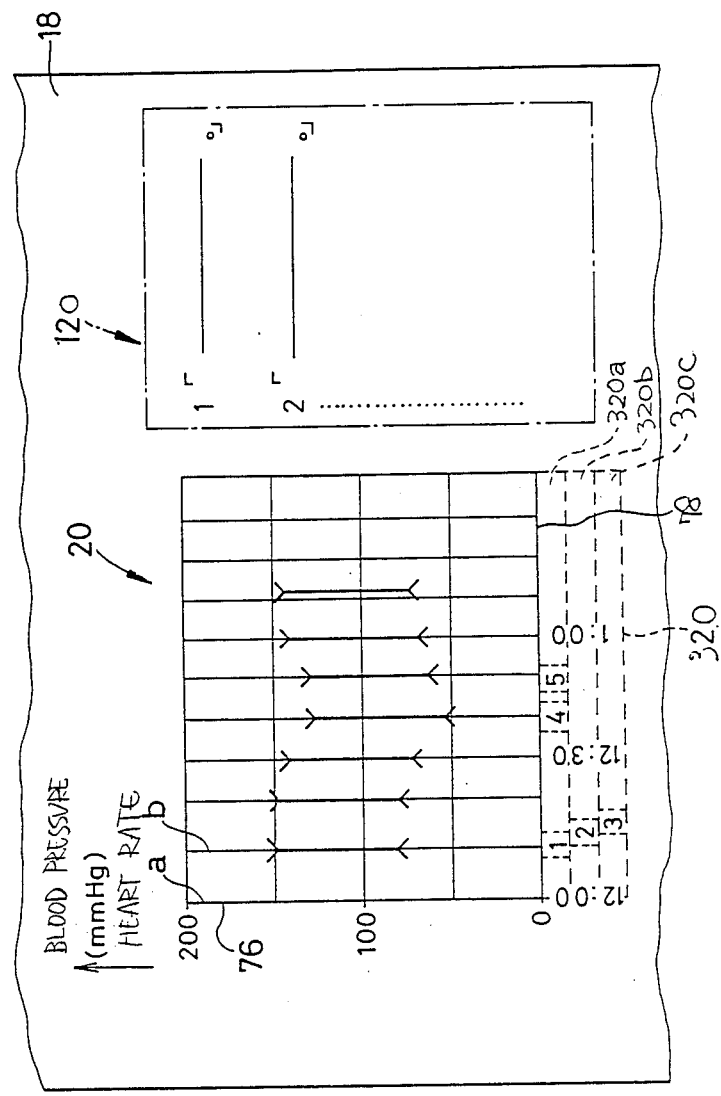

LIVING BODY INFORMATION RECORDER

BACKGROUND OF THE INVENTION

1. Field of the Art

The present invention relates in general to a living-body information recorder, and more particularly to an apparatus for effecting automatic repetitive detection of items of living-body information such as blood pressure, heart rate and breathing rate, and for automatically recording the detected living-body information in a two-dimensional chart area provided on a record sheet.

2. Related Art Statement

A plurality of items of living-body information on a patient are recorded in a predetermined two-dimensional chart area provided on a record sheet by means of recording respective indicia representative of the items, such as blood pressure, heart rate, breathing rate, body temperature, degree of saturation of oxygen in the blood, and concentration of a gaseous anesthetic contained in the expiration, so as to monitor the timewise varying trends of conditions of the patient during a surgical operation or in an intensive care unit (ICU). Such recordings of the living-body information, however, have been manually conducted by medical staff members.

Problem Solved by the Invention

It is time-consuming and troublesome to record the items of living-body information displayed by a monitor, in a predetermined two-dimensional chart area on the record sheet, because the number of medical staff members is apt to come short and they are very busy working in the hospital. As a result, the manual recordings of the living-body information might be conducted with errors.

SUMMARY OF THE INVENTION

It is therefore an object of the present invention to eliminate the time-consuming and troublesome job of manually recording living-body information in a record sheet.

It is another object of the invention to prevent the erroneous recordings of living-body information in the record sheet.

According to the present invention, there is provided an apparatus for effecting automatic repetitive detection of at least one item of living-subject information selected from a plurality of items of information on a living subject, and for automatically recording the detected living-subject information in a predetermined two-dimensional chart area provided on a recording medium, by means of recording respective indicia representative of the living-subject information, at respective recording positions in the chart area, which correspond to times of detection of the living-subject information, including: (A) a sensing device for detecting the living-subject information; (B) a recording device including a support for supporting the recording medium so as to permit manual recording of auxiliary information other than the living-subject information on the recording medium, and further including recording means movable relative to the recording medium for recording the indicia in the chart area; and (C) control means, responsive to the sensing device, for determining the recording positions of the indicia based on the detected living-subject information and the times of detection of the living-subject information, and for controlling the recording device so as to record the indicia at the determined recording positions in the chart area.

In the apparatus constructed as described above, the auxiliary information other than the living-body information which includes the names of medicines administered to the living subject, the times at which the medicines are administered, and the titles of medical treatments applied to the living subject, can be recorded by the operator or other members in a predetermined area other than the two dimensional chart area on the recording medium even during the automatic recording operation of the apparatus.

In accordance with an advantageous embodiment of the invention, the apparatus further includes a clock circuit which generates time signals representative of the times of detection, and the control means determines the recording positions based on the time signals and the living-subject information.

In a preferred form of the above-indicated embodiment, each of the recording positions of the indicia is determined along a first and a second chart axis of the two-dimensional chart area, and the times of detection and a value of the detected living-subject information are taken along the first and second chart axes, respectively. The control means includes alarm means for producing an alarm signal when the recording position which has been determined last is located outside the chart area in a direction along the first chart axis.

This form of the apparatus permits the operator to replace the recording medium by another at a time at which the recording medium cannot be recorded any longer. Therefore, it assures reliable recordings of the living-subject information.

According to another embodiment of the invention, the control means includes a detector for producing a signal indicative of the presence or absence of the recording medium on said support, and means for inhibiting the recording of the indicia while the signal indicates the absence of the recording medium, and permitting the recording of the indicia while the signal indicates the presence of the recording medium.

Since the above-indicated embodiment of the apparatus is inhibited from recording of the indicia while the recording medium is absent on the support, it assures reliable recordings like the previously-indicated preferred form of the invention.

According to a further embodiment of the invention, the apparatus further includes input means for specifying a location and a size of the two-dimensional chart area, by means of tracing a periphery of the chart area, and memory means for storing area data representative of the location and size of the chart area entered through the input means, and the control means determines the location and size of the chart area based on the area data stored in the memory means, and determines the recording positions of the indicia in the determined chart area, based on the living-subject information and the times of detection. The input means may include means for generating position signals indicative of operator-controlled movements of the recording means along the periphery of the chart area, so that the control means determines the area data based on the position signals.

The above-indicated embodiment of the apparatus permits accurate recordings of the indicia in the two dimensional chart area, even though the chart area is provided out of place with respect to the support due to out-of-place printing thereof on the recording medium, the shrinkage or expansion of the recording medium, and/or out-of-place positioning of the recording medium on the support.

In a preferred form of the above-indicated embodiment, the input means includes operator-controlled means for moving the recording means relative to the recording medium along the periphery of the chart area, and the area data is stored into the memory means as the operator-controlled means is operated to move the recording means along the periphery of the chart area.

The above-indicated preferred form of the apparatus permits the operator to conduct the tracing operation with accuracy, because the operator can follow the recording means with his eyes.

In another preferred form of the embodiment, each of the recording positions of the indicia is determined along a first and a second chart axis of the two-dimensional chart area, and the times of detection and a value of the detected living-subject information are taken along the first and second chart axes, respectively. The input means of this form includes operator-controlled means for specifying maximum values that are taken along the first and second chart axes.

In still another form of the embodiment, the control means includes means for moving the recording means according to the area data stored in the memory means, to permit verification of the location and size of the specified chart area through movements of the recording means.

According to a still further embodiment of the invention, the apparatus further includes input means for selecting one of a plurality of markings indicative of items of the auxiliary information, and the control means is responsive to the input means, for activating the recording device to record the selected marking in the chart area at a position corresponding to the time at which the selected marking is inputted, and to record the selected marking at a corresponding position in an auxiliary recording area provided on the recording medium for recording the auxiliary information.

The above-indicated embodiment makes the operator free from the troublesome job of writing the indicia corresponding to the items to be recorded, not only in the two dimensional chart area but in the auxiliary area on the recording medium. It also eliminates the possibility of an erroneous recording that an indicia is recorded out of position in the chart area.

In a preferred form of the above-indicated embodiment, the two dimensional chart area includes a plurality of recording tracks provided along one of adjacent two sides thereof. The control means judges whether or not a marking has been already recorded at a position at which the selected marking is to be recorded, in one of the plurality of recording tracks, and records the selected marking at the position if the judgement is negative, but records the selected marking at a position correspondong to the time in another recording track of the plural recording tracks if the judgement is affirmative.

According to still another embodiment of the invention, the apparatus further includes a display device for indicating the living-subject information detected by the sensing device, and operator-controlled means for inhibiting the recording device from recording the indicia representative of the living-subject information indicated on the display device, in the chart area.

In a preferred form of the above embodiment, the apparatus further includes another operator-controlled means for activating the sensing device to re-detect the living-subject information, and the another operator-controlled means is operable after the operation of the recording device is inhibited by activation of the operator-controlled means described in the above paragraph.

According to another embodiment of the invention, the apparatus further includes judging means for checking if a value of the living-subject information detected by the sensing device falls within a predetermined valid range, and inhibiting means for inhibiting the recording device from recording the indicia representative of the detected living-subject information, if the judging means judges that the detected value does not fall within the predetermined valid range.

This embodiment of the apparatus prevents the recording device from recording erroneous living-subject information due to physical activities and/or artifact noises of the subject. Therefore, the reliability of the living-subject information recorded on the recording medium is increased.

In a preferred form of the above-indicated embodiment, the apparatus further includes operator-controlled means for activating the sensing device to re-detect the selected item of living-subject information, and the operator-controlled means is operable after the inhibiting means is activated to inhibit the operation of the recording device.

This preferred form of the appartus is advantageous in that, in the case where the erroneous living-subject information is found, a good measurement of the living-subject information is newly obtained so as to prevent a lacking of living-subject information in that case.

According to a further embodiment of the invention, the apparatus further includes sensing means for detecting a location of the predetermined chart area on the recording medium on the support, and memory means for storing position data representative of the detected location of the chart area. The control means determines the recording positions of the indicia in the chart area, based on the detected living-subject information, the times of detection and the position data stored in the memory means.

This embodiment of the invention assures accurate recordings of the indicia in the two dimensional chart area in spite of possibly out-of-place positioning of the recording medium on the support, or variation of the location of the chart area on the recording medium due to shrinkage or expansion of the recording medium and/or inaccurate printing of the chart area on the recording medium.

In a preferred form of the above-indicated embodiment, the recording device further includes a carriage capable of holding the recording means and movable relative to the recording medium, and wherein the sensing means includes a photosensor which is disposed on the carriage and detects light reflected by the recording medium. The sensing means detects the location of the predetermined chart area on the recording medium by means of the photosensor.

In another preferred form of the embodiment, the recording device further includes a carriage movable relative to the recording medium in an X direction and a Y direction normal to the X direction, and a holder member fixed to the support and capable of holding a plurality of the recording means. The carriage is capable of selectively fetching one of the plural recording means from the holder member and returning the one recording means to the holder member. The sensing means including a light receiving element and an optical fiber which is connected to the light receiving element at one end thereof and fixed at the other end thereof to the lower end portion of one of the plural recording means. The optical fiber receives light reflected by the recording medium and transmitting the light to the light receiving element.

According to a still further embodiment of the invention, the apparatus further includes memory means for storing the detected living-subject information and position data representative of the recording positions of the corresponding indicia which have been recorded in the chart area; operator-controlled means for commanding re-recording of the corresponding indicia; and re-recording control means, responsive to the operator-control means, for activating the recording device according to the living-subject information and the position data stored in the memory means, for re-recording the corresponding indicia.

In the above-indicated embodiment of the invention, an indicia recorded in a scratchy or broken state due to shortness or drying of the ink can be re-recorded so as to allow the operator to read the indicia. Further, a copy of the recording medium recorded is obtained by means of replacing the recorded medium by another and operating the operator-controlled means. In the case where a plurality of recording media are stacked on each other on the support, the auxiliary information other than the living-subject information is transcribed from the top recording medium to the next below one, by means of writing the information in a (carbon-)copying part of the recording medium with substantial forces. Moreover, the present embodiment is advantageous in that, in the case where a plurality of indicia corresponding to the different items of living-subject information are recorded with respective specified colors, a copy is obtained such that the indicia recorded on the copy have the same specified colors as on the original recording medium.

According to still another embodiment of the invention, the recording device is an X-Y plotter including drive means for moving the recording means relative to the recording medium on the support, along an X axis and a Y axis in a plane parallel to a recording surface of the recording medium, and the apparatus further includes; (A) is detector for detecting a manual-recording state in which the manual recording of the auxiliary information on the recording medium is permitted, the detector generating a manual-recording signal when the manual-recording state is detected; and (B) drive control means, responsive to the manual-recording signal, for controlling the drive means so as to retract the recording means to a predetermined retracted position which is selected so that the recording means located at the retracted position will not interfere with a hand of a person who achieves the manual recording of the auxiliary information, the recording means being held at the retracted position while the manual-recording signal is present.

The above-indicated embodiment of the invention permits the operator to perform the manual recording of the auxiliary information with ease, because it has eliminated the possibility of a sudden starting of the recording means.

In a preferred form of the above-indicated embodiment, the detector includes a pen holder for accommodating a marker used for effecting the manual-recording of the auxiliary information, and a sensor for sensing the marker accommodated in the pen holder.

In another preferred form of the embodiment, the detector includes a photoelectric sensor array of reflection type for sensing the hand of the person positioned above the support of the recording device.

According to a still further embodiment of the invention, the apparatus further includes: (A) a sensor for detecting positions of at least two markings provided on the recording medium such that the markings are spaced apart from each other by a predetermined nominal distance from each other in a plane parallel to the recording medium; (B) determining means for determining an actual distance between the two markings based on the detected positions thereof, and determining a ratio of the determined actual distance to said nominal distance, which indicates a degree of shrinkage or expansion of the recording medium; and (C) compensation means for modifying drive signals to be applied to drive means to operate the recording means according to the ratio, so as to compensate the recording positions of the indicia for a variation of the actual distance from the nominal distance.

The above-indicated embodiment of the invention is advantageous in that the indicia is accurately recorded in the two dimensional chart area even though the recording medium is subjected to shrinkage or expansion thereof.

In a preferred form of the above-indicated embodiment, the determining means determines the ratio before the recording device records the indicia, or at predetermined time intervals during an entire period of recording of the indicia on the recording medium.

In another preferred form of the embodiment, the chart area is substantially rectangular and the at least two markings include a pair of first markings which are spaced from each other by a first nominal distance along a first axis parallel to one of two adjacent sides of the chart area, and a pair of second markings which are spaced from each other by a second nominal distance along a second axis parallel to the other of the two adjacent sides. The sensor detects a first actual distance between the first markings, and a second actual distance between the second markings. The determining means determines a first ratio of the first actual distance to the first nominal distance, and a second ratio of the second actual distance to the second nominal distance. The compensation means modifies the drive signals according to the determined first and second ratios, to compensate the recording postions of the indicia for variations of the first and second actual distances from the first and second nominal distances, respectively.

According another embodiment of the present invention, the plurality of items of information on a living body include blood pressure, heart rate, respiration rate, body temperature, degree of saturation of oxygen in the blood, and concentration of an anesthetic contained in the expiratory gas.

BRIEF DESCRIPTION OF THE DRAWING

The above and optional objects, features and advantages of the present invention will become more apparent from reading the following detailed description of preferred embodiments of the invention, when considered in connection with the accompanying drawings in which:

FIGS. 31 and 32 are a flow chart showing the operation of the control device of FIG. 30, respectively;

FIG. 51 is a view showing a sensor pen employed in the apparatus of FIG. 49;

FIG. 52(a) is a partially cross sectional view showing an optical fiber cable disposed in the sensor pen of FIG. 51;

FIG. 52(b) is a bottom view showing an arrangement of the optical fiber cable;

FIG. 53 is an illustrative view in cross section showing light emission and light reception of the optical fiber cable;

FIG. 56 is a view, corresponding to FIG. 52(b), showing another optical fiber cable employed in the apparatus of FIG. 49; and FIG. 57 is a view showing an anesthesia record sheet employed in another embodiment of the apparatus according to the present invention.

DETAILED DESCRIPTION OF THE PREFERRED EMBODIMENTS

To further clarify the present invention, there will be described in detail preferred embodiments of the apparatus according to the invention for automatically recording information about a living body on a record sheet, with reference to the accompanying drawings.

EXAMPLE I

Figure 1:
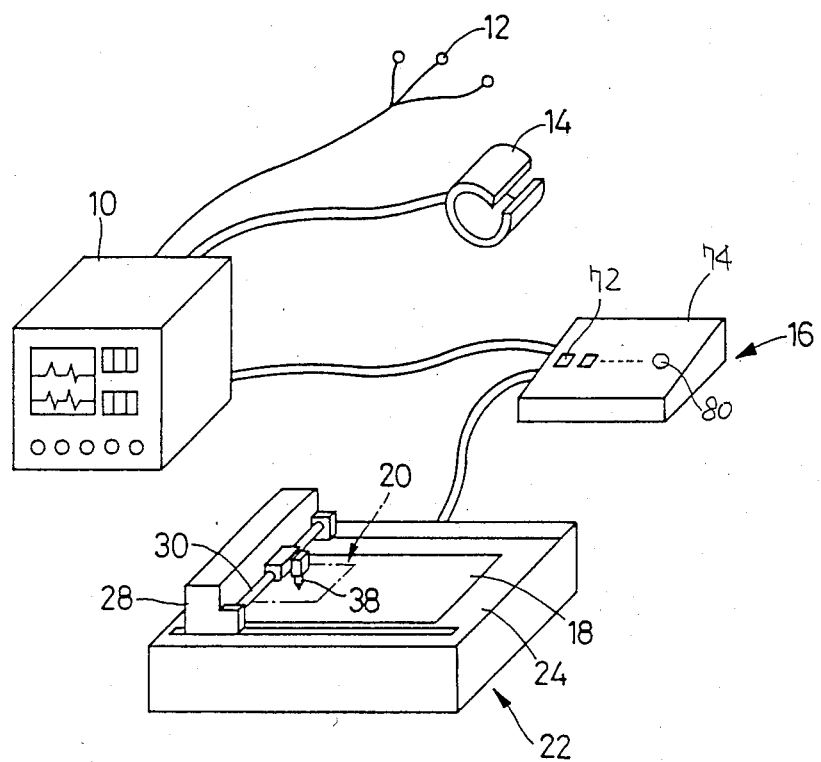
FIG. 1 shows a general arrangement of a preferred embodiment of an apparatus according to the present invention.

Referring first to FIG. 1, there is illustrated an apparatus according to the present invention for automatically recording a plurality of items of living body information on a subject or a patient under anesthesia during a surgical operation, wherein reference numeral 10 designates a sensing device in the form of an automatic blood pressure monitor provided with an electrocardiograph. A plurality of electrodes 12 and an inflatable cuff 14 are each connected to the blood pressure monitor 10. The blood pressure monitor 10 detects, periodically or in response to an operator's manual operation, plural items of living body information on a living subject, such as systolic and diastolic blood pressure, heart rate, breathing rate (number of respiration), anesthetic-gas concentration, and blood-oxygen concentration. The monitor 10 applies a detection signal representative of the value of the detected living subject information to control means in the form of the control device 16. The above-indicated breathing rate is determined, for example, by detecting variations of impedance between the electrodes 12. An X-Y plotter 22 as recording means of the instant embodiment records on an anesthesia record sheet 18 respective kinds of indicias corresponding to the plural items of living body information. Based on a detection signal from the blood pressure monitor 10, the control deveice 16 determines a recording position at which an indicia corresponding to the detection signal is recorded, in a two-dimensional chart area 20 provided at a predetermined location on the anesthesia record sheet 18. The control device 16 causes the X-Y plotter 22 to record the indicia at the recording position determined. The control device 16, automatic blood pressure monitor 10 and X-Y plotter 22 may be formed as a unitary device.

Figure 2:
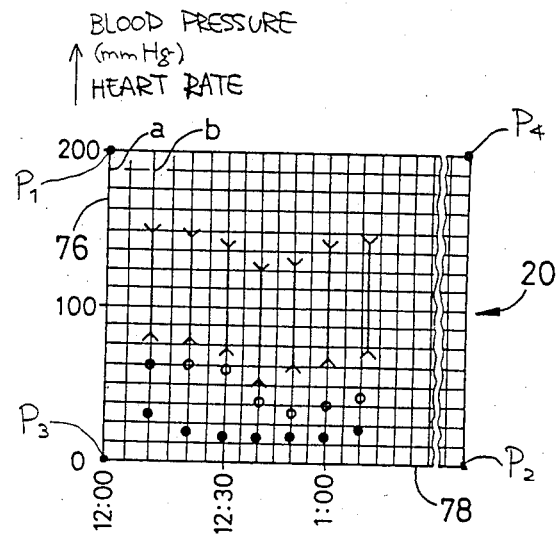
FIG. 2 shows a two dimensional chart area provided on an anesthesia record sheet which is used with the apparatus of FIG. 1.

The anesthesia record sheet 18 is used for recording thereon timewise varying trends of living-body information on a subject under anesthesia, together with the titles or names of administered anesthetics or other medicines. The record sheet 18 has the two-dimensional chart area 20 such that the chart area 20 is located respective predetermined distances apart from two adjacent sides of the record sheet 18 which are positioned on the X-Y plotter 22. The two-dimensional chart area 20 is ruled into a multiplicity of squares. As can be seen in FIG. 2, the chart area 20 has a first axis, axis of abscissa, indicative of time and a second axis, axis of ordinate, indicative of the values of living body information, such as blood pressure, heart rate, respiration rate, body temperature, degree of saturation of oxygen in the blood, concentration of one or more anesthetics contained in the expiratory gas, and/or the like.

Figure 3:
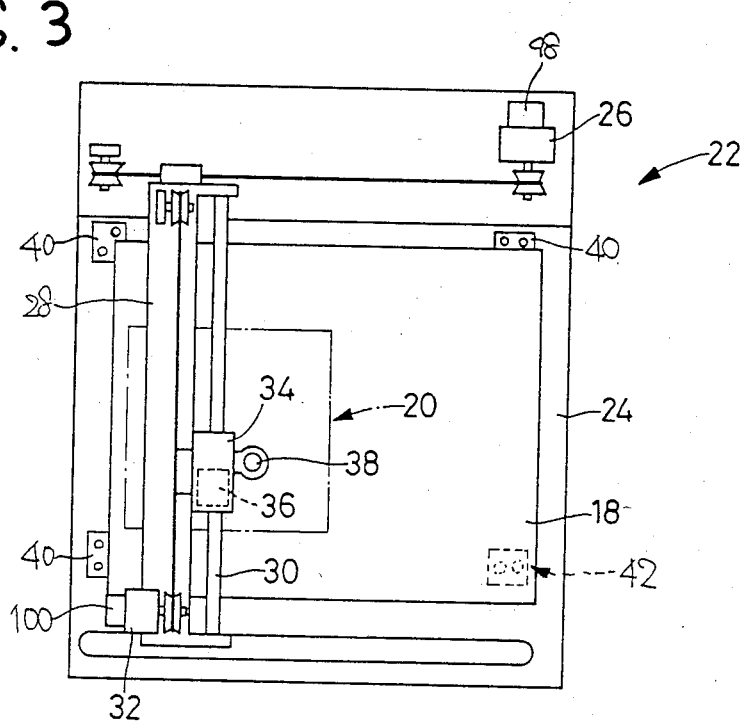
FIG. 3 shows an X-Y plotter used for the apparatus of FIG. 1.

As clearly shown in FIG. 3, the plotter 22 includes a support 24 for supporting the record sheet 18, a movable member 28 which is moved and positioned in an X direction by an X stepper motor 26, and a carriage 34 which is moved along a guide rod 30 disposed on the movable member 28 and is positioned in a Y direction normal to the X direction, by a Y stepper motor 32. The plotter further includes recording means in the form of a recording pen 38 which is disposed on the carriage 34 and elevated up and down by an up/down solenoid 36. On the support 24 are fixedly disposed positioning members 40 for accurately positioning the record sheet 18 at a predetermined location. In order to retain the record sheet 18 on the support 24, a vacuum attraction device or an electrostatic attraction device may be utilized as needed. In the support 24 is embedded a sheet sensor 42 for checking if the record sheet 18 is on the support 24.

Figure 4:
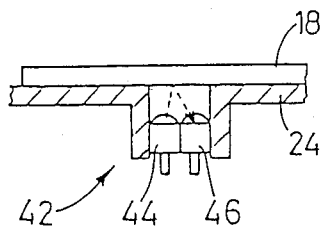
FIG. 4 shows a sheet sensor embedded in a support of the X-Y plotter of FIG. 3.

As illustrated in FIG. 4, the sheet sensor 42 includes a light emitter 44 for emitting light beams toward the under surface of the record sheet 18, and a light receiver 46 for receiving the light beams reflected by the same 18. The sheet sensor 42 detects the record sheet 18 placed on the support 24 by means of detecting the light beams reflected by the record sheet 18, and supplies a sheet signal representative of the presence or absence of the record sheet 18 on the support 24, to the control device 16.

Figure 5:
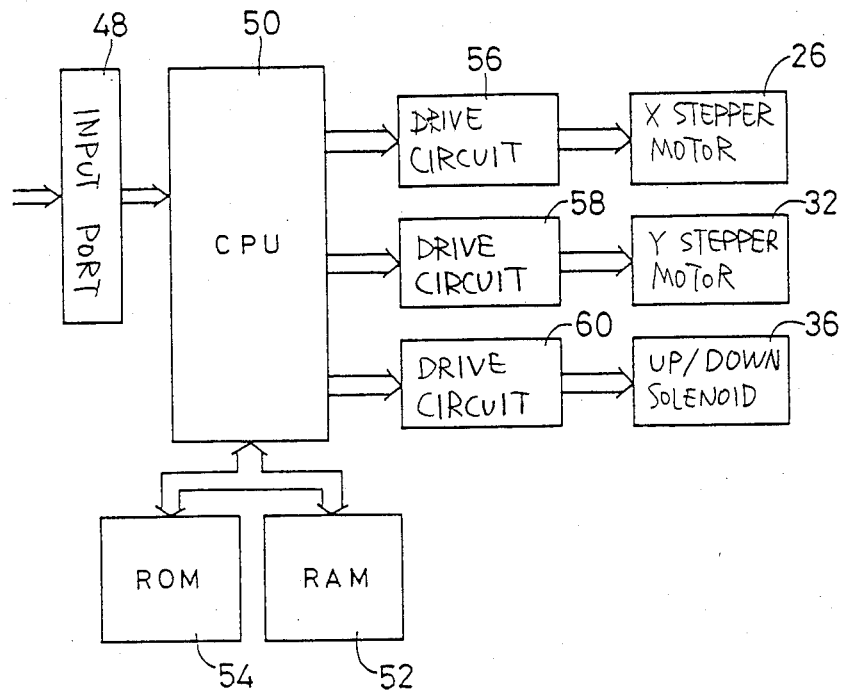
FIG. 5 is a block diagram showing a control circuit employed for the X-Y plotter.

The X-Y plotter 22 is provided 22 is provided with a control circuit illustrated in FIG. 5. The control device 16 supplies to an input port 48 of the control circuit a record signal representative of the indicia to be recorded and its recording position in the two-dimensional chart area 20. A central processing unit (CPU) 50 processes the record signal received while utilizing the storing function of a random access memory (RAM) 52 and the programs pre-stored in a read only memory (ROM) 54. The CPU 50 applies respective drive signals to a drive circuit 56 for supplying drive power to the X stepper motor 26, to a drive circuit 58 for supplying drive power to the Y stepper motor 32 and to a drive circuit 60 for supplying drive power to the up/down solenoid 36.

Figure 6:
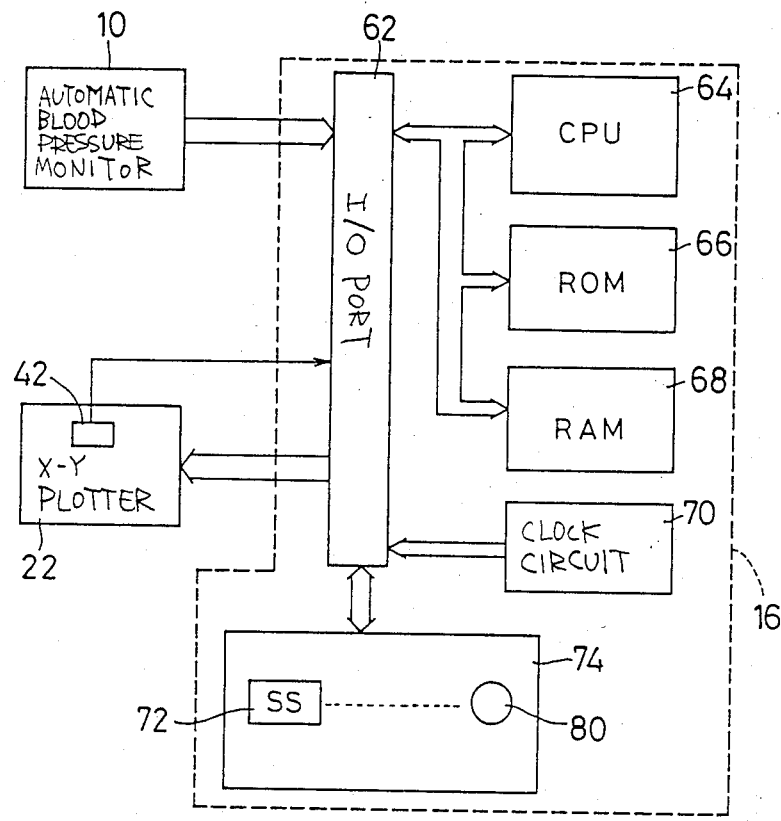
FIG. 6 is a block diagram showing a construction of a control device which is used for the apparatus of FIG. 1.

Referring next to FIG. 6, the control device 16 includes an I/O port 62, CPU 64, ROM 66, RAM 68, clock circuit 70 for generating a time signal representative of current time, and an input console 74 having a start/stop pushbutton 72 and an alarm lamp 80 for ordering the operator to replace the record sheet 18 by another. The CPU 64 processes an detection signal while using the storing function of the RAM 68 and the programs pre-stored in the ROM 66, and applies to the X-Y plotter 22 a record signal representative of a recording position of an indicia in the two-dimensional chart area 20.

Referring to a flow chart shown in FIG. 7, there will be described the operation of the control device 16. This flow chart indicates a control routine which is started upon depression of the start/stop pushbutton 72 and stopped by another depression of the same 72.

Usually, prior to depression of the start/stop pushbutton 72, the automatic blood pressure monitor 10 had been activated to be ready for periodically measuring maximum and minimum blood pressure, heart rate, breathing rate and the like of the subject in an automatic fashion. Upon depression of the start/stop pushbutton 72, step S1 is started for executing initialization operations. Step S1 is followed by step S2. Step S2 is repeatedly executed until a detection signal is supplied from the monitor 10. When a detection signal is supplied, step S3 is subsequently executed to store not only the data represented by the detection signal but the current time at which the detection signal is received based on a time signal generated by the clock circuit 70.

Step S3 is followed by step S4 wherein an indicia to be recorded and its recording position in the chart area 20 are determined based on the location and the size of the chart area 20 which have been pre-stored, and the data and current time of the detection signal which have been stored at the preceding step S3. More specifically described, the recording position of an indicia is determined as follows. Firstly, a line parallel to the axis of ordinate 76, which corresponds to the current time of the axis of abscissa 78, is selected in the two-dimensional chart area 20. Then, a point of corresponding to the value of the data is placed on the above-selected line having the pre-sorted full-scale value.

At the following step S5, it is checked whether or not the recording position determined at step S4 is outside the two-dimensional chart area 20. This step is mainly intended for checking if the selected point is positioned out of the length of the axis of abscissa 78 (time axis). Usually, the selected point falls within the chart area 20, and step S5 is followed by step S6. At step S6, a record signal indicative of the indicia and its recording position is outputted to the X-Y plotter 22. The plotter 22 records, based on the record signal received, the value of living-body information measured by the automatic monitor 10, by way of writing the indicia at its recording position in the two-dimensional chart area 20. As illustrated in FIG. 2, immediately after the activation of the monitor 10, the indicia is recorded along a line indicated at "a", and after 10 minutes the indicia is recorded along a line indicated at "b". FIG. 2 shows the indicia " >--< " that represents maximum and minimum blood pressure, the indicia "O" that represents breathing rate (number of respiration) and the indicia "●" which represents heart rate (number of blood pressure pulses). The current time is recorded near the time axis 78 each time an indicia is recorded or at suitable intervals.

After repetition of the above described steps, the timewise varying trends of items of living body information are illustrated on the two-dimensional chart area 20 as a result of successively recording the indicia representative of blood pressure, together with other indicias as shown in FIG. 2. And when time has elapsed over the full-scale time (e.g., 3 hours) corresponding to the length of the time axis 78, the judgement at step S5 turns affirmative (YES). That is, it is judged at step S5 that the recording position determined at step S4 goes outside the time axis 78. In this case, step S7 is subsequently executed to stop the recording operation and produce an alarm signal. Thus, an alarm lamp 80 is turned on while alarm sound is generated by a alarm device (not shown). At the following step S8, the full-scale time value of the time axis 78 is automatically set, and the recording position is determined based on the new full-scale value. The length of the time axis 78 of the chart area 20 on the new record sheet 18 corresponds to the full-scale time value newly set. At step S9, it is judged whether or not the recording sheet 18 has been replaced by another. This judgement is made by means of checking for the absence and susequent presence of the sheet signal supplied from the sheet sensor 42. Step S9 is repeated until the recording sheet 18 is replaced, and after a replacement the CPU 64 goes to step S6 to execute further operations.

As described hitherto, in the present embodiment, the control device 16 determines the recording position in the two dimensional chart area 20 corresponding to the measurement value obtained by the automatic blood pressure monitor 10 and the time at which the monitor 10 obtained the measurement value, and the X-Y plotter 22 automatically records the indicia representative of the measurement value at the recording position determined. Therefore, the time-consuming and troublesome job of recording items of living body information on the record sheet 18 is completely eliminated without producing any recording errors. In this connection, it is appreciated that the record sheet 18 is placed on the X-Y plotter 22, thereby permitting the operator to easily access to the sheet 18. In other words, even during the automatic recording operation, the operator can write by hand the name of an administered anesthetic and the administration time at which the anesthetic is administered, in a suitable area on the record sheet 18.

Further, in the present embodiment, alarm sound is automatically generated in the case where the predetermined recording position of an indicia is over the length of the time axis 78 of the two dimensional chart area 20. This allows replacement of the recording sheet 18 by another, and subsequent recordings of the indicias on the record sheet 18. As a result, the recording operation is conducted with certainty.

While the present embodiment employs the automatic blood pressure monitor 10 which measures blood pressure, heart rate, breathing rate and the like, it may employ other monitors which measure essential living body information, for example, body temperature, in place of or in addition to the blood pressure monitor 10.

Also, the X-Y plotter 22 may be replaced by other types of recording devices, such as a dot printer which records figures in a serial or parallel fashion, an ink-jet printer and an X-Y recorder.

While the X-Y plotter 22 is provided with the control circuit of FIG. 5 in this embodiment, the control device 16 may be adapted to directly control the X stepper motor 26, Y stepper motor 32 and up/down solenoid 36.

The clock circuit 70 of the control device 16 of the present embodiment may be omitted in the case where the automatic monitor 10 generates a signal representative of a measurement time at which a measurement is conducted, or in the case where the monitor 10 periodically generates a detection signal and only the indicias corresponding to the periodical detection signals are recorded at their recording positions which are equally spaced from each other in a direction of the time axis 78.

Furthermore, the positioning members 40 disposed on the X-Y plotter 22 may be replaced by a combination of plural holes formed at suitable positions of the record sheet 18 and projections which are formed on the support 24, and enagage with those holes of the record sheet 18.

Throughout the following descriptions about further embodiments, there will be held a rule that, if an element of the above-indicated embodiment and an element of another embodiment have the same feature, both are given the same reference numeral and the description for the element of the another embodiment is omitted.

EXAMPLE II

Another embodiment of the apparatus according to the invention will be described.

Figure 8:
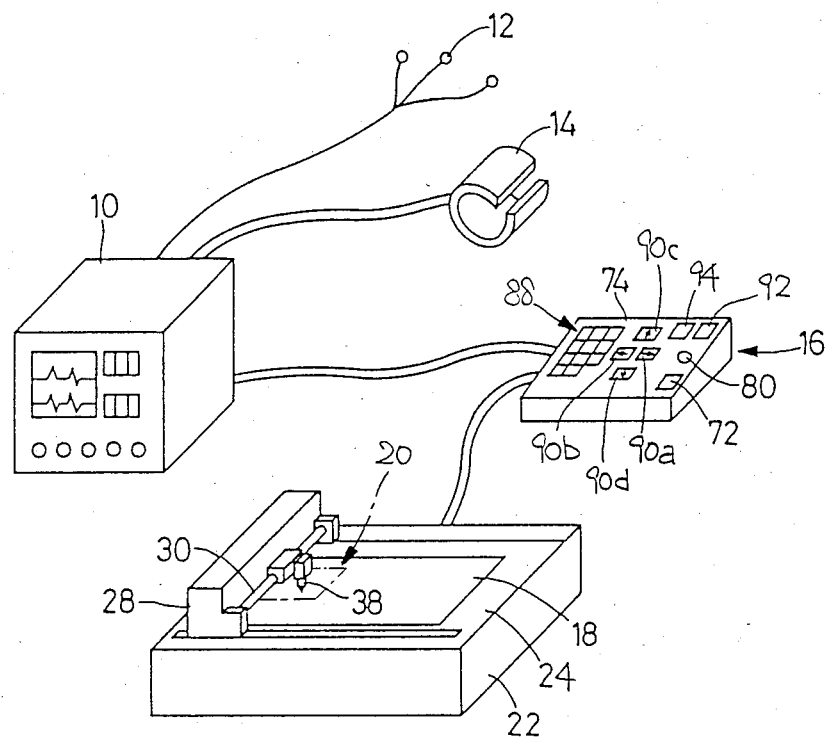
FIG. 8 is a view, corresponding to FIG. 1, showing a general arrangement of another embodiment of the apparatus.
Figure 9:
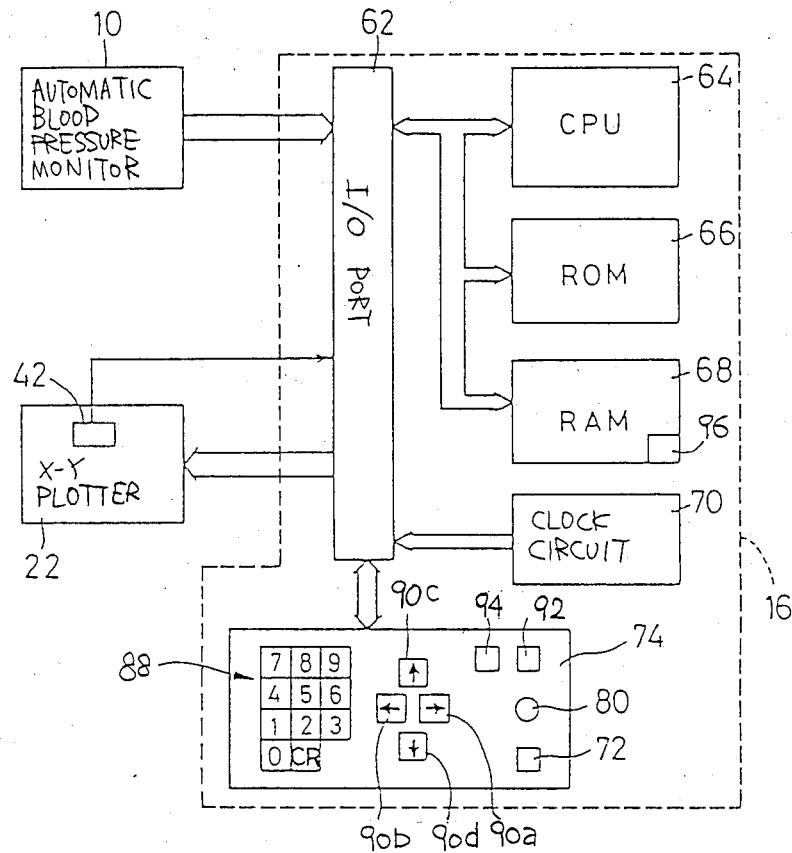
FIG. 9 is a block diagram, corresponding to FIG. 6, showing a construction of a control device of the apparatus of FIG. 8.

Referring to FIGS. 8 and 9, there is illustrated a control device 16 of this embodiment which includes an I/O port 62, central processing unit (CPU) 64, read only memory (ROM) 66, random access memory (RAM) 68, clock circuit 70 and input console 74. The input console 74 has ten numeral keys 88, four direction keys 90a, 90b, 90c and 90d, memory key 92, test key 94, start/stop pushbutton 72 and alarm lamp 80. The CPU 64 processes a detection signal by means of utilizing the storing function of the RAM 68 and using the programs pre-stored in the ROM 66, and applies to the X-Y plotter 22 (FIG. 3) a record signal representative of the indicia to be recorded and its recording position in the two dimensional chart area 20.

Figure 7:
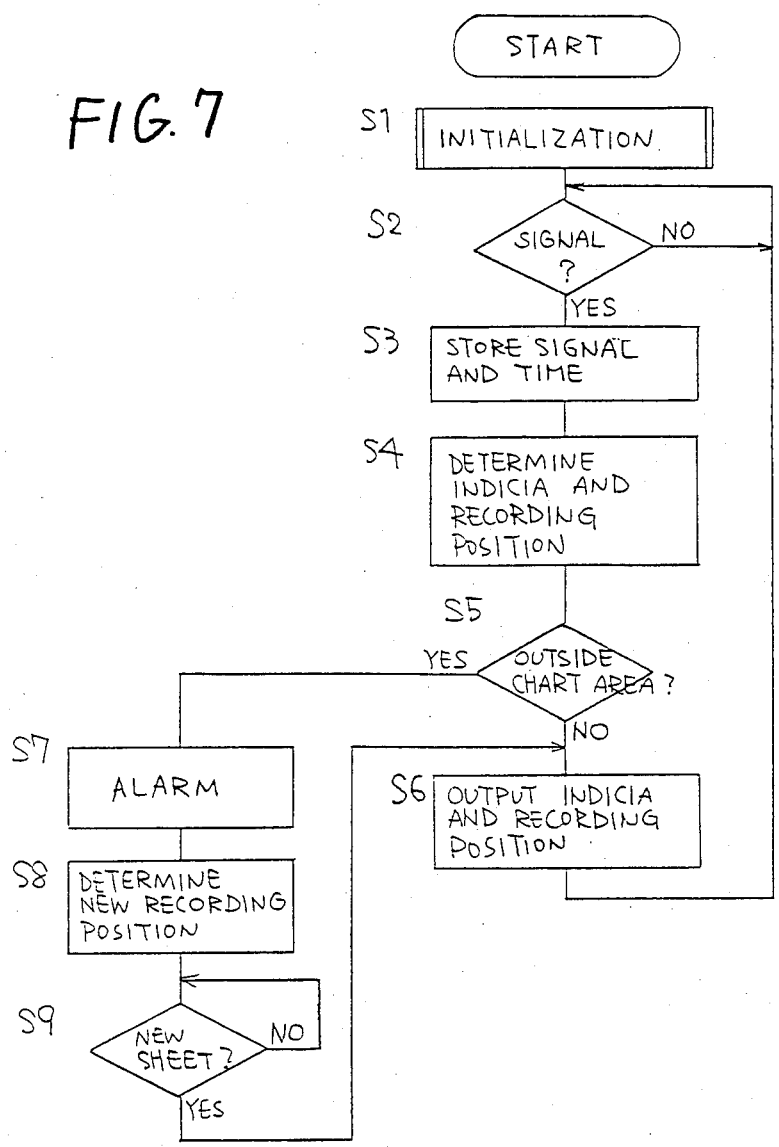
FIG. 7 is a flow chart showing the operation of the control device of FIG. 6.

The control device 16 of the prevent embodiment is operated according to the flow chart of FIG. 7, except the initializing operations. The instant control device 16 executes the initializtion operations according to a chart area input routine shown in FIG. 10 wherein the location and size of the chart area 20 are entered and stored, and wherein the full-scale values for the axes of ordinate and abscissa 76 and 78 are also entered and stored.

Figure 10:
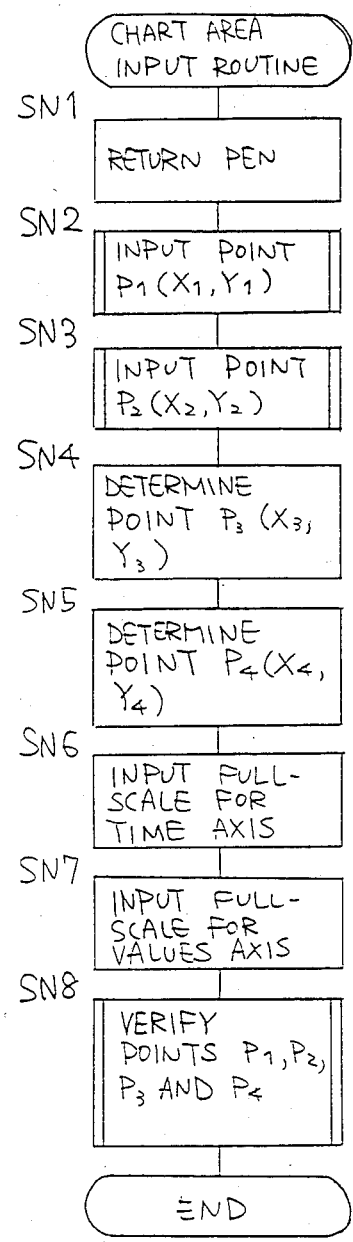
FIGS. 10 and 11 are a flow chart showing the operation of entering the location and size of a two dimensional chart area in the apparatus, respectively.

The chart area input routine of FIG. 10 will be described in detail. The location and size of the chart area 20 are entered by means of positioning the pen 38 at each of the four corners of the chart area 20 and then operating the memory key 92 at each time. The full-scale values for the axes 76 and 78 are entered and stored by means of operating the numeral keys 88 and memory key 92.

At step SN1 of the routine, the X-Y plotter 22 is supplied with a signal to position the pen 38 at an initial point, and the plotter 22 causes the pen 38 to move to the initial point, for example, point (X0, Y0) at the left and lower corner of a predetermined range within which the pen 38 is adapted to move around (FIG 3). At step SN1, an X and a Y register (described below) are zeroed, respectively. At the following step SN2, is entered point P1(X1, Y1) at the left and upper corner of the chart area 20 of FIG. 2. This is made by means of operating the four direction keys 90a(RIGHTWARD), 90b(LEFTWARD), 90c(UPWARD) and 90d(DOWNWARD). At step SN2, is executed a point position input routine shown in FIG. 11 wherein, first at step ST1, it is judged whether or not the RIGHTWARD key 90a has been operated. If the judgement at step ST1 is affirmative (YES), step ST1 is followed by step ST2 to supply, to the X-Y plotter 22, a signal to move the pen 38 by one step in a righward direction as seen in FIG. 3, and to add the value of one to the current content of the X register. These steps ST1 and ST2 are repeated until the operation of the RIGHTWARD key 90a is finished. If the judgement at step ST1 is negative (NO), that is, if the RIGHTWARD key 90a has not been operated, step ST1 is followed by step ST3 to judge whether or not the LEFTWARD key 90b has been operated. In the case where the judgement at step ST3 is affirmative, the CPU 64 goes to step ST4 to move the pen 38 by one step in a leftward direction as viewed in FIG. 3, and to subtract one from the current content of the X register. In the case where the judgement at step ST3 is negative (NO), that is, where the LEFTWARD key 90b has not been operated, step ST3 is followed by step ST5 to check whether or not the UPWARD key 90c has been oparated. If the judgement at step ST5 is affirmative, step ST5 is followed by step ST6 to move the pen 38 by one step in a upward direction as seen in FIG. 3, and to add one to the current content of the Y register. On the other hand, if the judgement at step ST5 is negative, that is, if the UPWARD key 90c has not been worked, step ST5 is followed by step ST7 to see whether or not the DOWNWARD key 90d has been operated. If the judgement at step ST7 is affirmative, step ST8 is executed to move the pen 38 by one step in the downward direction as viewed in FIG. 3, and to substract the value of one from the current content of the register Y. In this way, the pen 38 is moved to the position of point P1(X1, Y1) at the left and upper corner of the two dimensional chart area 20. Then, the memory key 92 is operated. The operation of the memory key 92 results in the affirmative judgement at step ST9 and permits the execution at step ST10. At step ST10, the contents of the X and Y registers are stored as the position of point P1 (X1, Y1) at the left and upper corner of the chart area 20.

Referring back to FIG. 10, at step SN3, the position of point P2(X2, Y2) at the right lower corner of the two dimensional chart area 20 is entered as the position of point P1(X1, Y1) is entered at step SN2.

Once the positions of point P1(X1, Y1) and P2(X2, Y2) are entered, steps SN4 and SN5 are subsequently executed to automatically determine and store the positions of point P3(X3, Y3) at the right and upper corner of the chart area 20 and point P4(X4, Y4) at the left and lower corner of the same 20, respectively. At the following step SN6, the full-scale value for the axis of abscissa (time axis) 78 are entered by means of operating the numeral keys 69 and then operating the memory key 92. Similarly, the full-scale value for the axis of ordinate 76 is entered and stored at the next step SN7. In order to make the overall length of the axis 78 equal to 3 hours, for example, the full-scale value of 300 is entered while, in order to make the length of the axis 76 to correspond to 200 mmHg, the full-scale value of 200 is entered. The thus entered actual location and size of the chart area 20 and full-scale values for the two axes 76 and 78 are stored in a chart area storing region 96 in the RAM 68 (FIG. 9). The CPU 64, RAM 68 and other members for executing the chart area input routine cooperate to serve as chart area input means.

Finally, at step SN8, based on operation of the test key 94, a signal is supplied to cause the X-Y plotter 22 to move the pen 38 from point P1 to points P2, P3 and P4 to verify that the enterings of the positions of points P1, P2, P3 and P4 have been conducted with accuracy. In other words, the operation of the test key 94 allows the pen 38 to travel along points P1, P2, P3 and P4 while illustrating a rectangular shape in the air. This operation permits the operator to confirm the entered positions of the points with his eyes.

After the various parameters about the two dimensional chart area 20 are stored by the control device 16, are executed further steps similar to step S2 and the subsequent steps of FIG. 7. As time elapses, the indicia " >-< " indicative of maximum and minimum blood pressure, the indicia "O" indicative of breathing rate and the indicia "●" indicative of heart rate are respectively recorded along the positive direction of the time axis 78 on the two dimensional chart area 20 of FIG. 2. At the same time, the current time is recorded near the time axis 78 each time the data is recorded or at suitable intervals. Thus, the timewise trends of items of living body information are recorded on the record sheet 18.

As described hitherto, in the present embodiment, the location and size of the two dimensional chart area 20 are entered by operating the four direction keys 90a through 90d, and stored in the chart area storing region 96 in the RAM 68. An indicia indicative of living body information is automatically recorded at its recording position on the chart area 20. Consequently, the indicias are written at their recording positions with accuracy, in spite of possible out-of-place printing of the chart area 20 on the record sheet 18, variation of the location of the chart area 20 due to shrinkage or expansion of the record sheet 18 or out-of-place positioning of the sheet 18 onto the support 24. Therefore, in the present embodiment, the recording sheet 18 may be placed on the support 24 according to lines printed on the support 24, and the positioning members 40 for positioning the record sheet 18 may be omitted.

Figure 12:
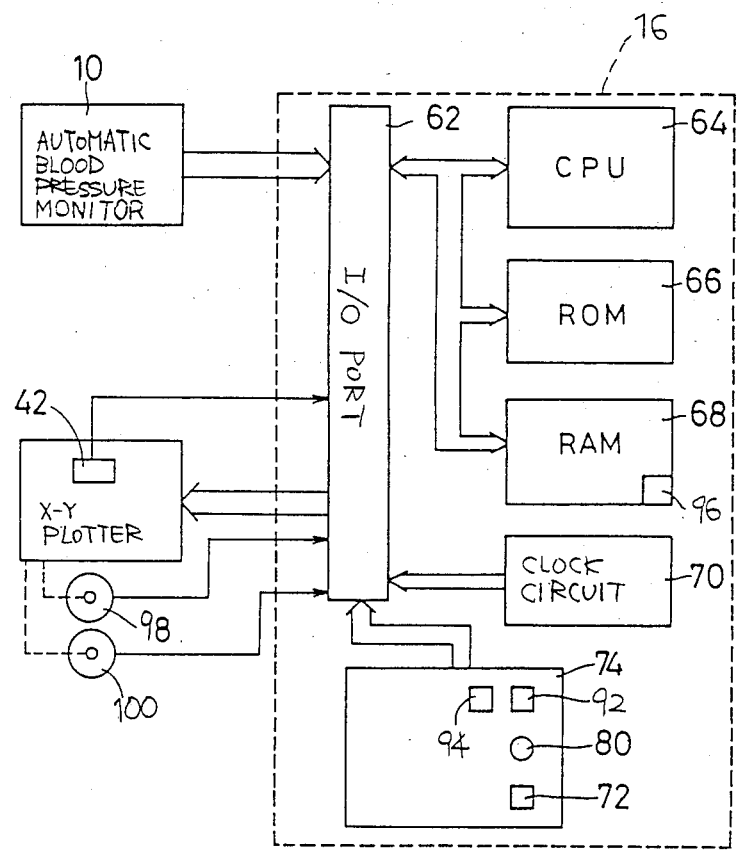
FIG. 12 is a block diagram showing a construction of a control device which is used in a preferred form of the embodiment of FIG. 8.

The chart area input means of this embodiment may be given another arrangement. As shown in FIGS. 3 and 12, the X stepper motor 26 and Y stepper motor 32 have an X rotary encode 98 and a Y rotary encode 100, respectively. A pulse signal is outputted from the X and Y encodes 98 and 100 to the control device 16 as control means. The pulse signal from the X rotary encode 98 indicates in which direction the pen 38 has been moved along the X direction, i.e., rightward or leftward as viewed in FIG. 3. Similarly, the Y rotary encode 100 generates a pulse signal representative of which direction the pen 38 taken of, the positive or negative directions along the Y direction, i.e., upward or downward direction as viewed in FIG. 3.

The chart area input means arranged above allows an INSTRUCTIVE operation for entering the positions of points P1, P2, P3 and P4 of the two dimensional chart area 20 by way of manually positioning the pen 38 at those points.

Figure 11:
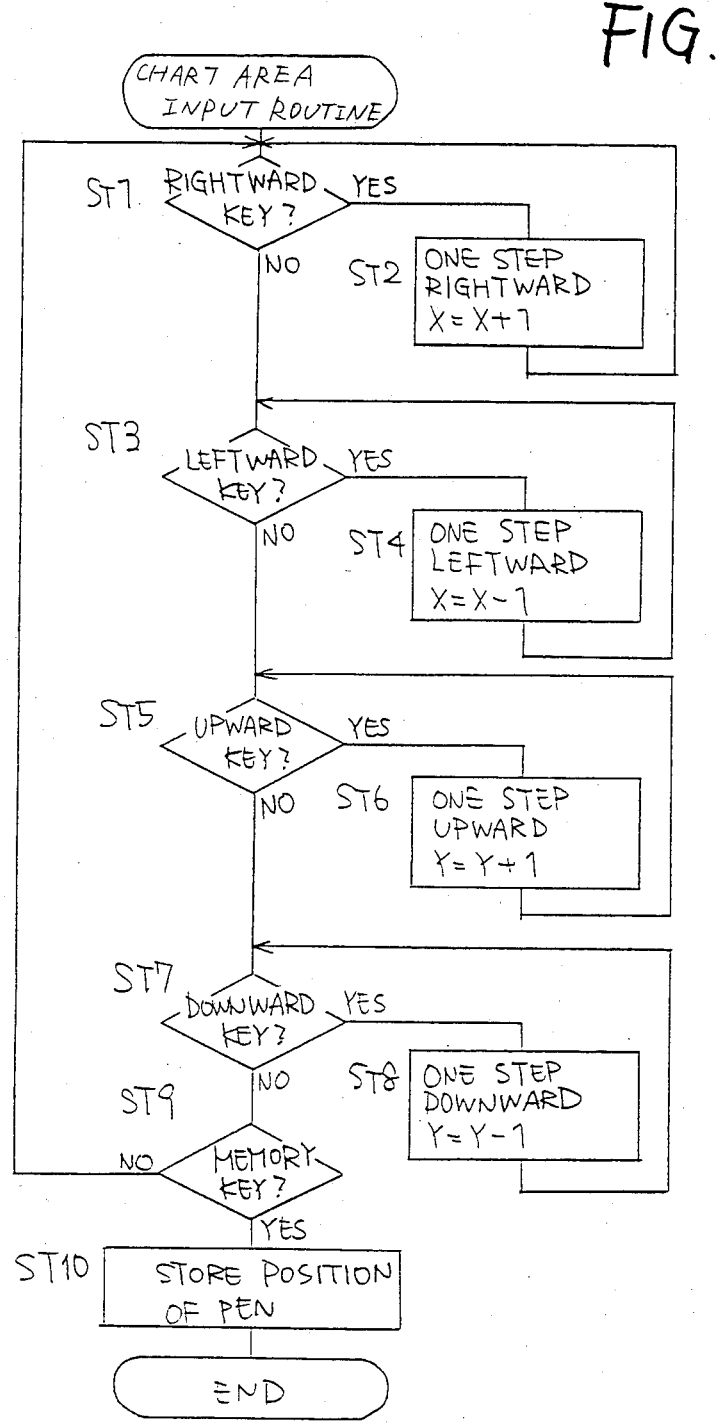
Figure 13:
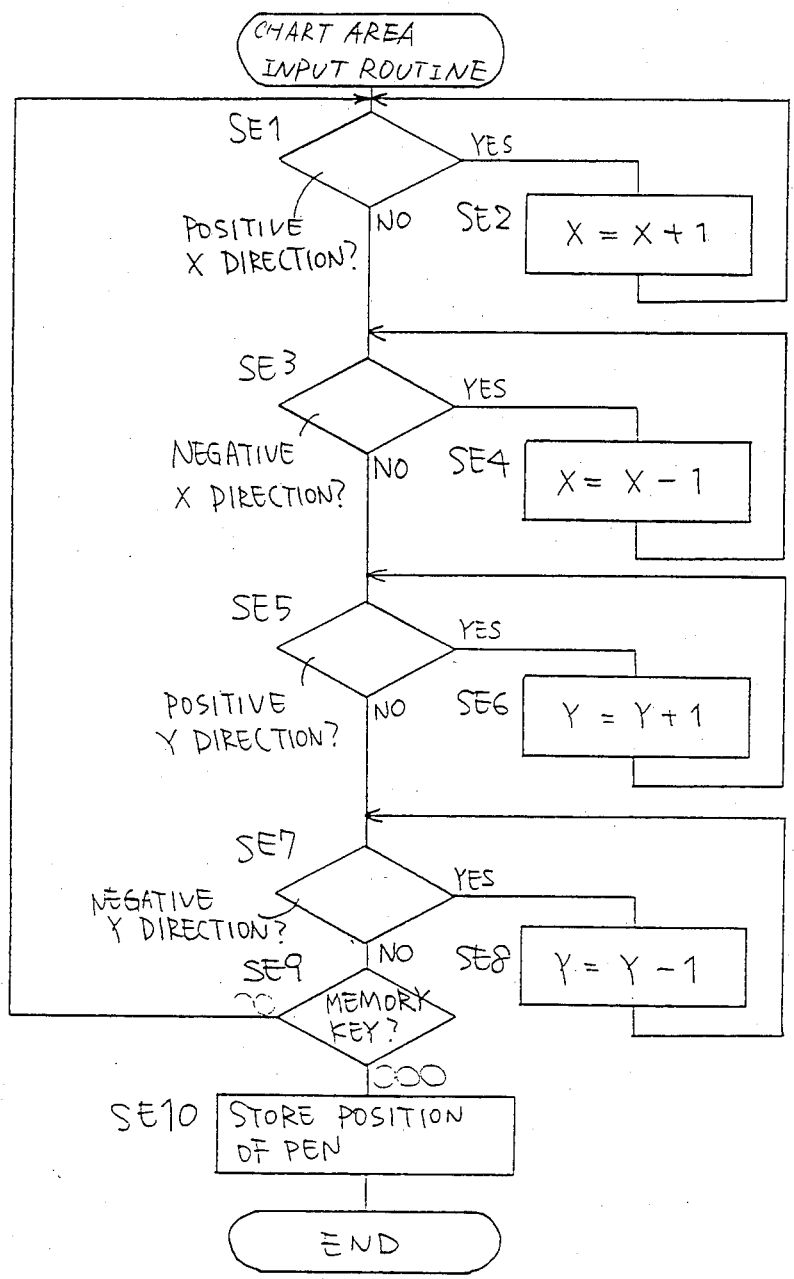
FIG. 13 is a flow chart, corresponding to FIG. 11, showing the operation of entering the size and location of a two dimensional chart area of the form of FIG. 12.

The operation of this chart area input means will be described hereafter with reference to a flow chart shown in FIG. 13, in place of the flow chart of FIG. 11 which has been referred to with regard to the previously-described input means. First, step SE1 is executed to judge whether or not the X rotary encode 98 has generated a positive signal representative of one-step movement of the pen 38 in the positive direction of the X direction. If the judgement at step SE1 is affirmative (YES), step SE1 is followed by step SE2 to add the value of one to the current content of the X register. These steps SE1 and SE2 are executed each time a positive pulse is generated from the X rotary encode 98. If the judgement at step SE1 is negative (NO), step SE1 is followed by step SE3 to check whether or not the X rotary encode 98 has generated a negative signal representative of one-step movement of the pen 38 in the negative direction of the X direction. If the judgement at step SE3 is affirmative, the CPU 64 goes to step SZ4 to subtract one from the current content of the X register. If the judgement at step SE3 is negative, the CPU 64 goes to step SE5 to see whether or not the Y rotary encode 100 has generated a positive signal representative of one-step movement of the pen 38 in the positive direction of the Y direction. In the case where the judgement at step SE5 is affirmative, step SE5 is followed by step SE6 to add one to the current content of the Y register. In the case where the judgement at step SE5 is negative, the CPU 64 goes to step SE7 to see whether or not the Y rotary encode 100 has produced a negative signal indicative of one-step movement of the pen 38 in the negative direction of the Y direction. If the judgement at step SE7 is affirmative, step SE7 is followed by step SE8 to subtract the value of one from the current content of the Y register. After the pen 38 is thus positioned at point P1(X1, Y1) at the left and upper corner of the chart area 20 by hand, the memory key 92 is operated. Consequently, the judgement at step SE9 turns affirmative, and the following step SE10 is executed to store the current contents of the X and Y registers as the position of point P1(X1, Y1). Therefore, the instant chart area input means includes the X and Y rotary encodes 98 and 100, memory key 92, RAM 68, ROM 66 having a chart area input program corresponding to the flow chart of FIG. 10, and CPU 64 which executes the flow chart of FIG. 10.

While the present embodiment is adapted to store the location and size of the two dimensional chart area 20 by means of storing the positions of two points P1 and P2 at the left and upper corner and right and lower corner of the chart area 20, it may be adapted to store those parameters by means of storing the positions of three points including point P3 or P4 in addition to points P1 and P2, permitting an inclination of the chart area 20 to be also stored. Furthermore, the positions of four points P1, P2, P3 and P4 may be entered so as to store the inclination and deformation of the chart area 20.

Further, it is possible to store the location and size of the two dimensional chart area 20 by means of storing the positions of predetermined points on the four sides of the chart area 20, such as middle points of those sides.

EXAMPLE III

There will be described still another embodiment of the invention.

Figure 14:
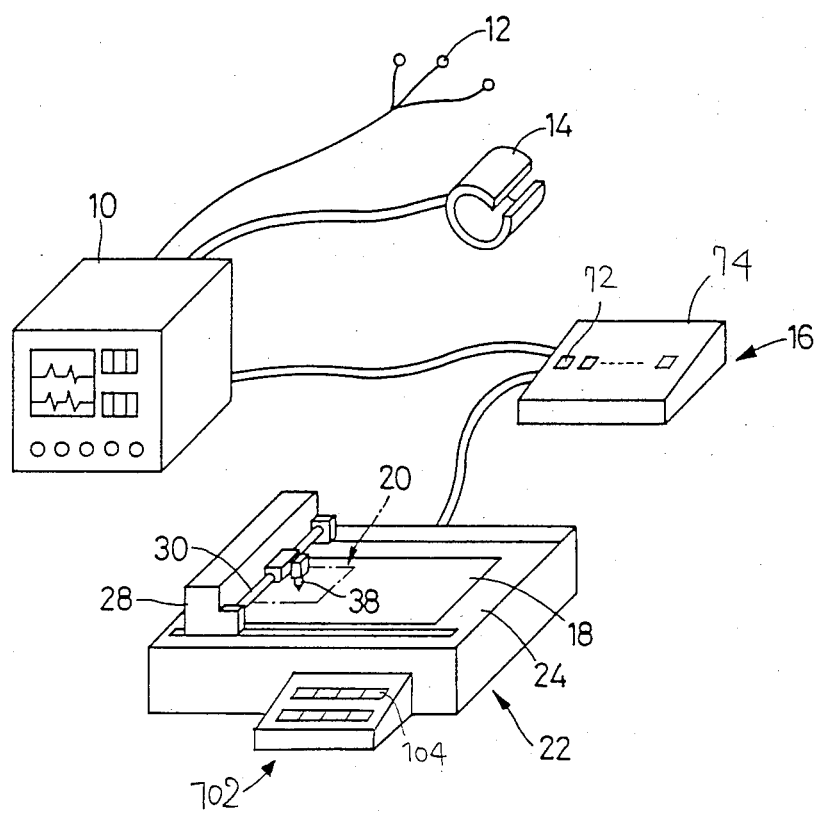
FIG. 14 is a view, corresponding to FIG. 1, showing a general arrangement of still another embodiment of the apparatus.
Figure 15:
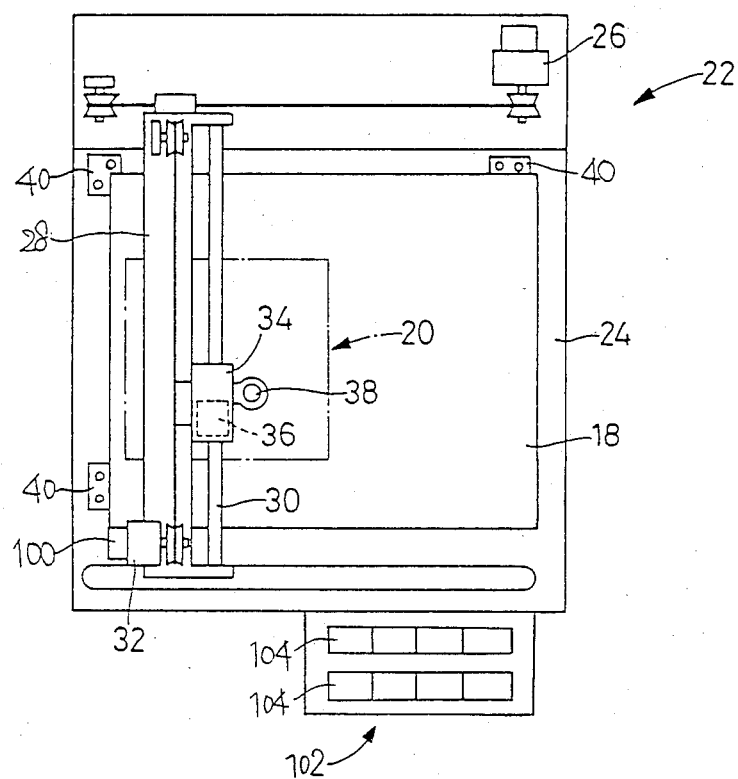
FIG. 15 is a view, corresponding to FIG. 3, showing an X-Y plotter used in the apparatus of FIG. 14.

Referring to FIGS. 14 and 15, there is illustrated an X-Y plotter 22 having a plotter control device 102. The present embodiment has a feature or recording a marking not only at a selected position in a two dimensional chart area 20 provided on an anesthesia record sheet 18 but at a selected position in an accessory area 120 provided on the same record sheet 18. The marking corresponds to the item recording of which is needed on the living body under anesthesia, such as, the title of a medicine given to the living body and the time at the administration, and the name of a medial treatment applied to the living body and the time at the treatment.

Figure 16:
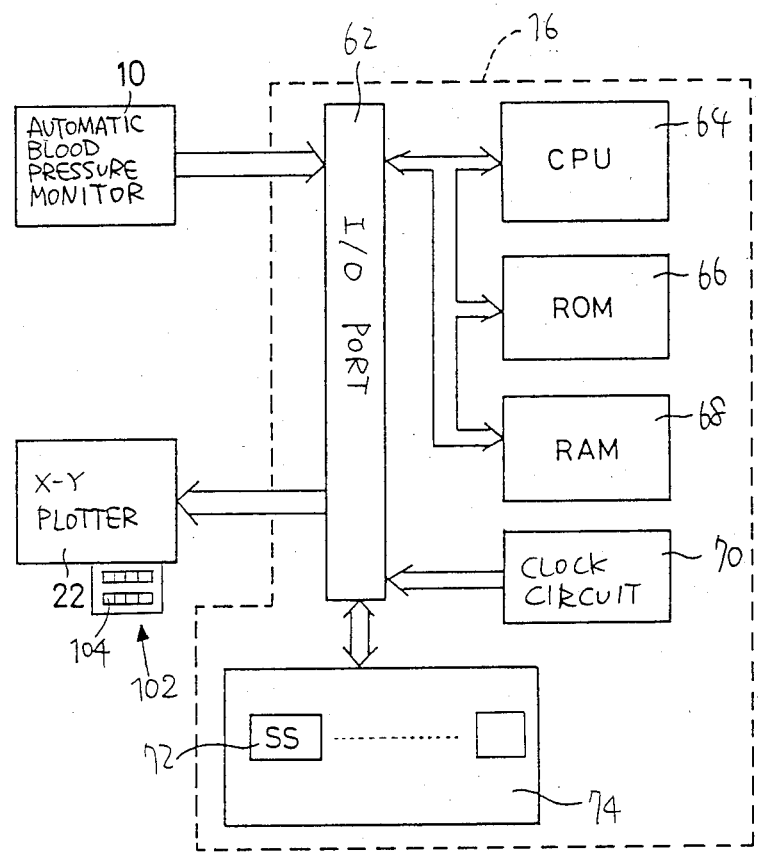
FIG. 16 is a block diagram, corresponding to FIG. 6, showing a construction of a control device of the apparatus.
Figure 17:
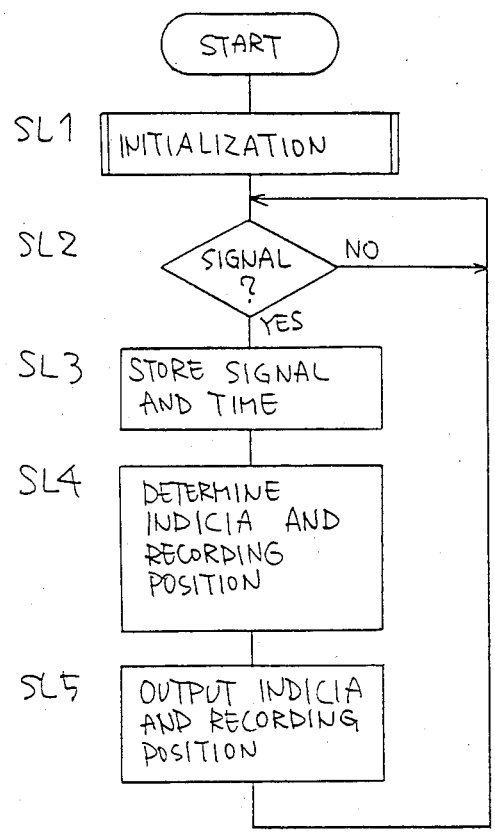
FIG. 17 is a flow chart, corresponding to FIG. 7, showing the operation of the control device of FIG. 16.

The control device 16 of this embodiment has a construction shown in FIG. 16, and operated according to a control routine indicated by a flow chart shown in FIG. 17. The control routine is started or stopped upon depression of a start/stop pushbutton 72. Prior to depression of the start/stop pushbutton 72, the automatic blood pressure monitor 10 is activated to be ready to automatically measure items of subject body information, such as blood pressure, heart rate and breathing rate, at suitable intervals. Next, on depression of the start/stop pushbutton 72, step SL1 similar to step S1 of FIG. 7 is executed for initialization. Subsequently are executed steps SL2, SL3, SL4 and SL5 respectively similar to steps S2, S3, S4 and S6 of FIG. 7, resulting in determining the indicia to be recorded and its recording position in the chart area 20, based on a detection signal which is entered from the automatic monitor 10 and the time at which the detection signal is entered and further resulting in recording the selected indicia at the determined position.

The plotter control device 102 which is disposed on the side wall of the X-Y plotter 22, has a plurality of special keys 104 for recording respective markings.

Figure 18:
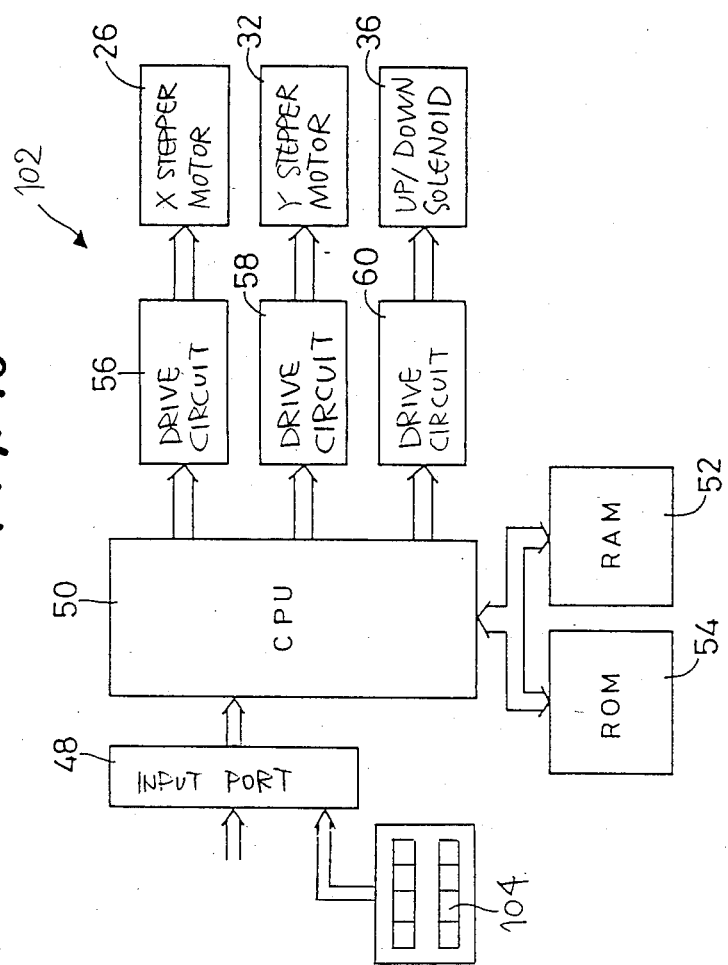
FIG. 18 is a block diagram, corresponding to FIG. 5, showing a control circuit for the X-Y plotter of FIG. 15.
Figure 19:
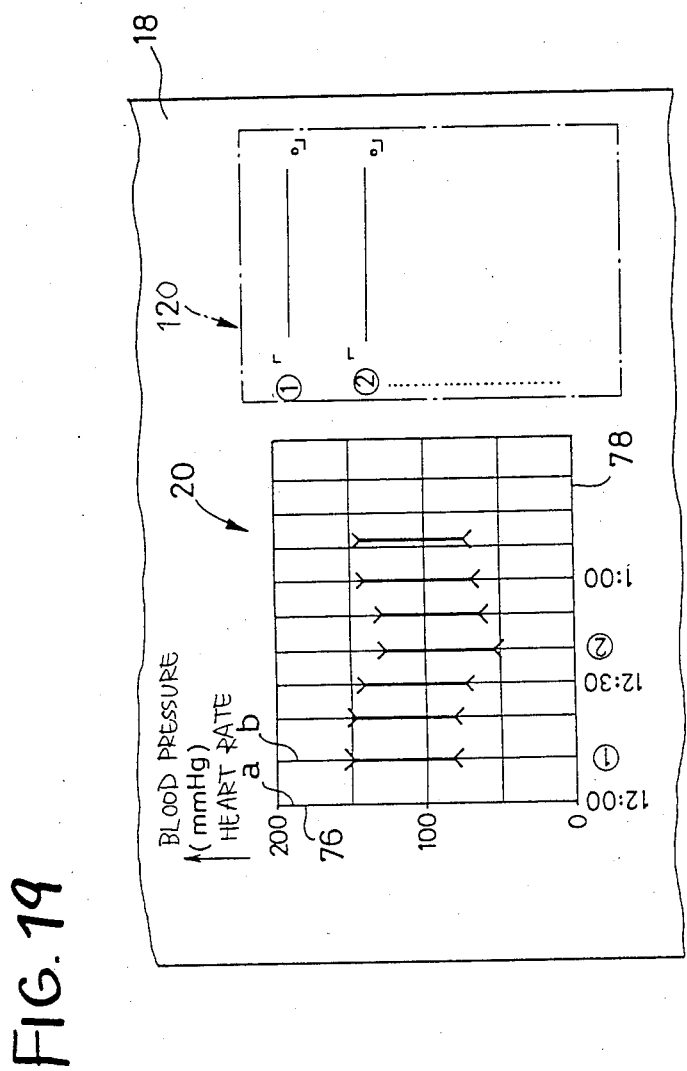
FIG. 19 is a view, corresponding to FIG. 2, showing an anesthesia record sheet used with the apparatus of FIG. 14.

The plotter control device 102 has a construction illustrated in FIG. 18. A CPU 50 of the plotter control device 102 receives at an input port 48 a record signal generated by the control device 16, and applies drive signals to respective drive circuits 56, 58 and 60, in response to the record signal received. In the meanwhile, responsive to operation of one of the special keys 104, the CPU 50 causes the X-Y plotter 22 to record the marking corresponding to the special key 104 operated, not only at the recording position in the chart area 20 corresponding to the current time at which the special key 104 is operated but at a predetermined position in the accessory area 120 provided on the same record sheet 18, which is illustrated in FIG. 19.

Figure 20:
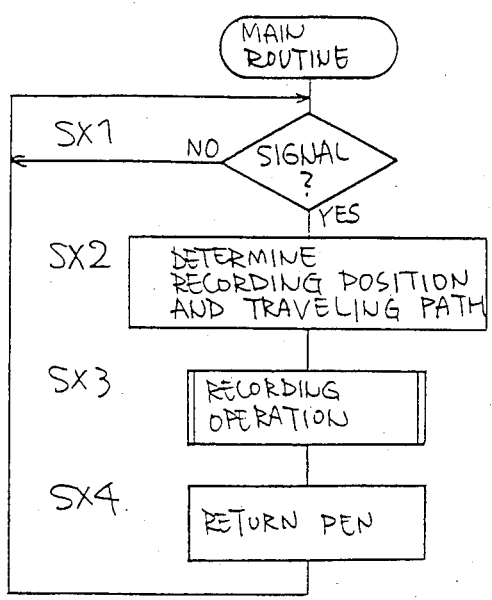
FIGS. 20 and 21 are a flow chart showing the operation of the control circuit of FIG. 18, respectively.

FIG. 20 illustrates a main routine for the operation of the X-Y plotter 22, wherein step SX1 is first executed to judge whether or not a record signal has been supplied from the control device 16. If the judgement at step SX1 is negative (NO), step SX1 is repeated until a record signal supplied is found. Once if the judgement at step SX1 turns affirmative (YES), step SX1 is followed by step SX2 wherein is determined a traveling path of the pen 38 along which the pen 38 is moved for recording the selected marking at the selected recording position. At the following step SX3, drive signals are respectively applied to the drive circuits 56, 58 and 60 so as to cause the pen 38 to actually travel along the traveling path and record the selected marking. Following completion of the recording with the pen 38, step SX4 is executed to generate a signal to return the pen 38 to its initial position, for example, the left and lower point on the support 24 (FIG. 14). With the pen 38 located at its initial position, the operator can read the record sheet 18 without interference. Therefore, step SX4 serves to permit the operator to easily observe the content or record of the record sheet 18, especially of the two dimensional chart area 20.

Figure 21:
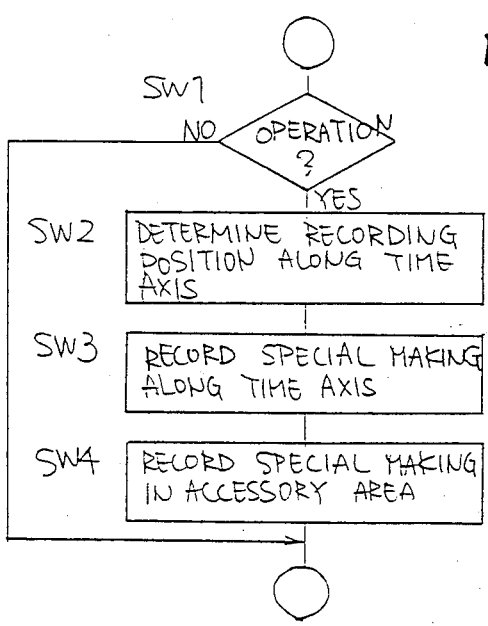

The above described main routine is interrupted by an interrupt routine shown in FIG. 21, at suitable intervals, for example, 10 milliseconds. At step SW1 of the interrupt routine, it is judged whether or not any one of the special keys 104 for recording the corresponding markings has been operated. In the case where the judgement at step SW1 is negative (NO), the interrupt routine is over. On the other hand, in the case where the judgement at step SW1 is affirmative (YES), step SW1 is followed by step SW2 wherein is determined the recording position of the selected marking in the two dimensional chart area 20. More specifically described, at step SW2, the time at which the special key 104 is operated is determined, based on a time signal from the control device 16 representative of the current time, and consequently the recording position of the selected marking corresponding to the time at which the special key 104 is operated is determined on the time axis 78 of the two dimensional chart area 20. And at the following step SX3, the special marking corresponding to the special key 104 operated is selected out of a plurality of markings which are pre-stored, and are generated drive signals to cause the pen 38 to record the selected marking at its recording position determined at step SW2. Subsequently, Step SW3 is followed by step SW4 to record the same special marking also at a predetermined position in the accessory area 120. The accessory area 120 has on its left side vertically aligned entry columns at which the marking selected are successively recorded as time elapses. On the right side of the accessory area 120 the operator can write down things associated with the marking. The numerals "1" and "2" shown in FIG. 19 designate the respective kinds of markings which have been automatically recorded based on operations of the different kinds of special keys 104.

As described hitherto, in the present embodiment, a marking is recorded by operating the corresponding special key 104 not only at the recording position along the time axis 78 which corresponds to the time at which the special key 104 is operated but at the position in the accessory area 120 corresponding to the same time. This recording method is useful for obtaining necessary items of living body information on a living body under anesthesia, such as the title of a medicine administered to the living body and the time at which the medicine is administered, or the name of a medical treatment applied to the living body and the time at which the treatment is applied. Therefore, in this embodiment, the special keys 104 serve as input means for selectively entering the marking corresponding to the required item of living body information about a living body under anesthesia. The ROM 54 for storing the program of FIG. 20, CPU 50 for executing that program and RAM 52 cooperate with each other to serve as control means for controlling a marking recording.

Thus, the present embodiment of the apparatus according to the invention has eliminated a troublesome job to record a marking corresponding to the required item of information on a living body under anesthesia, not only at the recording position in the chart area 20 corresponding to the time at which the item is required but also at the position in the accessory area 120 corresponding to the same time. Therefore, the present arrangement provides no possibility of out-of-place recordings of the marking in the two dimensional chart area 20, resulting in a higher reliability or correctness about the data recorded on the record sheet 18.

While the input means of the present embodiment is adapted to select one of the special keys 104, it may be means which selects a marking, based on vocal sound of the operator. In other words, it may be means of sound-input type.

Furthermore, in place of the CPU 50 of the plotter control device 102 for controlling the operation of recording a marking, another CPU, for example, CPU 64 of the control device 16, may be utilized to determine the marking and the recording position at which the indicia is recorded, based on a signal applied by the special key 104, and also to command the plotter control device 102 to execute the subsequent operations. In this case, the control device 16 and plotter control device 102 cooperate to serve as control means.

EXAMPLE IV

There will be described a further embodiment of the invention wherein, in the case where an erroneous measurement is made by the automatic blood pressure monitor 10, the erroneous measurement is canceled and the blood pressure monitor 10 is re-activated to obtain a good measurement.

Figure 22:
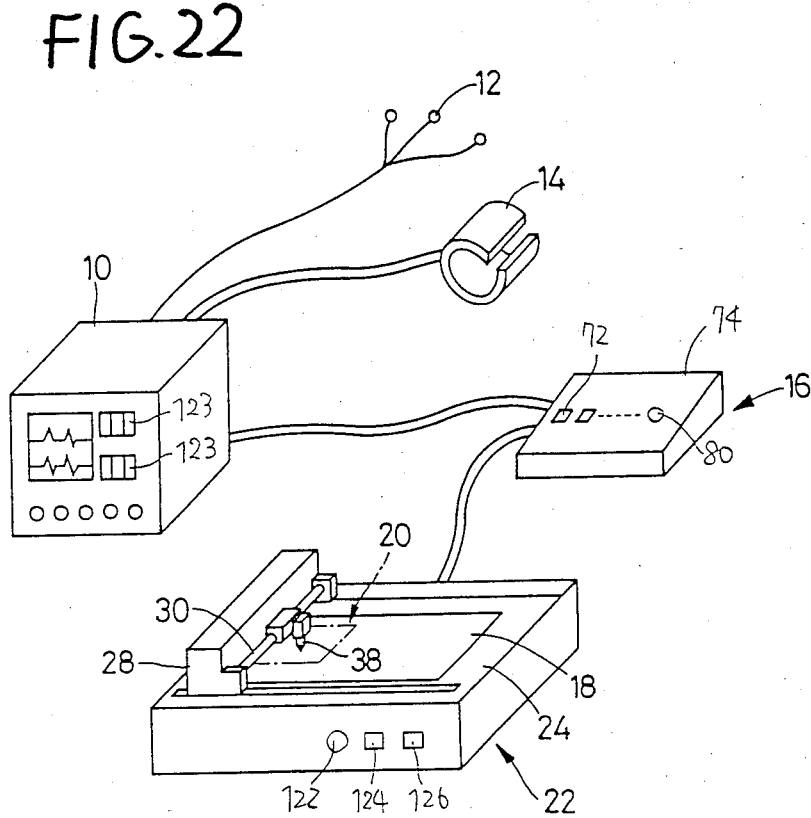
FIG. 22 is a view, corresponding to FIG. 1, showing a general arrangement of a further embodiment of the apparatus according to the present invention.
Figure 23:
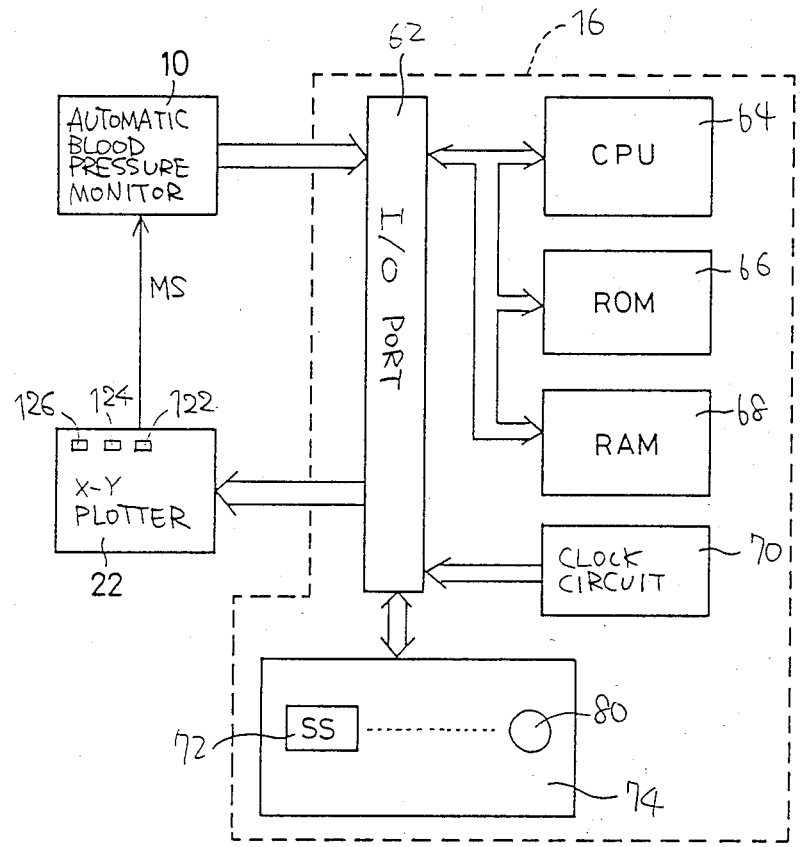
FIG. 23 is a block diagram, corresponding to FIG. 6, showing a construction of a control device of the apparatus of FIG. 22.

The present embodiment of the invention is arranged as shown in FIG. 22. A control device 16 has a construction as shown in FIG. 23, and operated according to the same flow chart as to that of FIG. 17. The control device 16 determines the indicia to be recorded and its recording position within the two dimensional chart area 20, based on a detection signal representative of a measurement supplied by the blood pressure monitor 10 and the current time at which the measurement is obtained, and generates a record signal representative of the selected indicia and its recording position, to an X-Y plotter 22.

Figure 24:
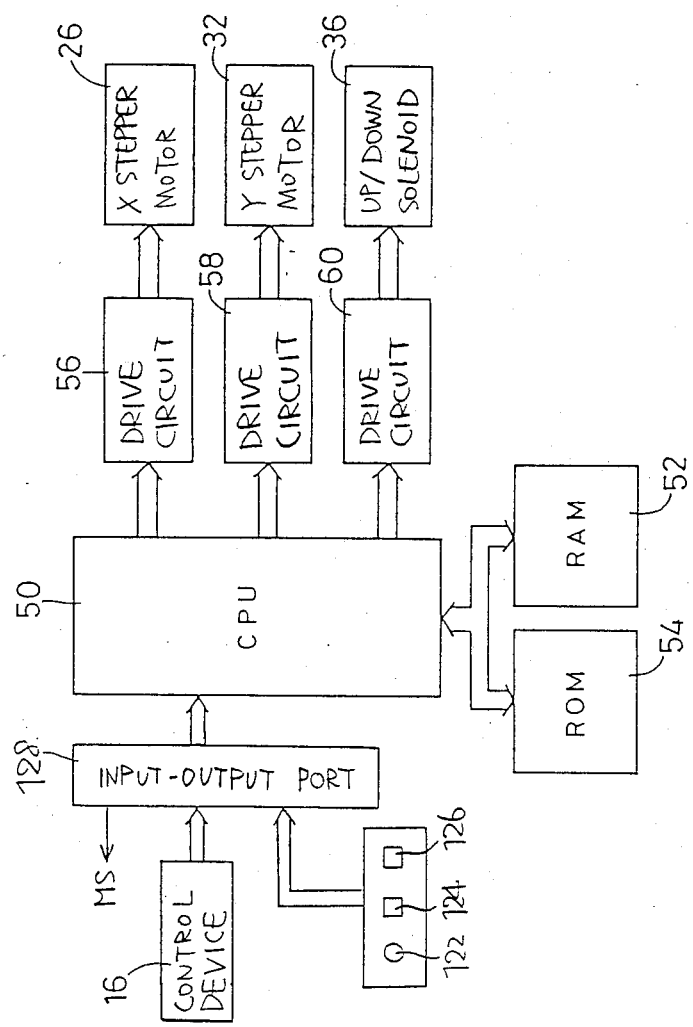
FIG. 24 is a block diagram, corresponding to FIG. 5, showing a control circuit used for an X-Y plotter of the apparatus.

As shown in FIGS. 22 and 23, the X-Y plotter 22 is provided with a CHECK lamp 122, EXECUTE key 124, and CANCEL key 126 on a side wall thereof. The CHECK lamp 122 demands the operator to give a permission to record the indicia selected. Operation of the EXECUTE key 124 means permission for the recording, while operation of the CANCEL key 126 means cancellation of the recording. FIG. 24 shows a control circuit of the X-Y plotter 22, including the CHECk lamp 122, EXECUTE key 124 and CANCEL key 126. As clearly shown in the figure, a CPU 50 receives at an input/output port 128 a record signal representative of the selected indicia and its recording position in the chart area 20 from the control device 16, and processes it by utilizing programs pre-stored in a ROM 54. The CPU 50 applies respective drive signals to drive circuits 56, 58 and 60 so as to record the selected indicia at the recording position in the two dimensional chart area 20. In the meantime, the CPU 50 applies, upon operation of the CANCEL key 126, a measurement signal MS to the automatic blood pressure monitor 10 through the input-/output port 128.

Figure 25:
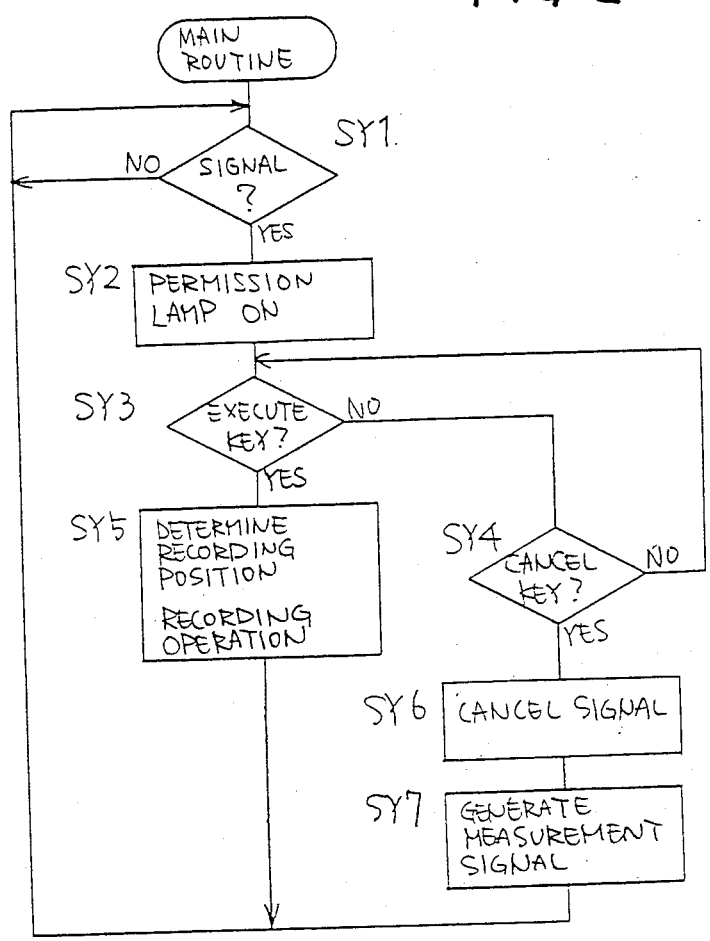
FIG. 25 is a flow chart showing the operation of the control circuit of FIG. 24.

On the above-indicated control circuit of the X-Y plotter 22, operations are executed according to a flow chart shown in FIG. 25. First, step SY1 of the flow chart is started to check whether or not there is presence of a record signal from the control device 16. If there is no signal, that is, if the judgement at step SY1 is negative (NO), step SY1 is repeated while waiting for a record signal. If there is presence of a record signal, that is, if the judgement at step SY1 is affirmative (YES), step SY1 is followed by step SY2 to turn on the CHECK lamp 122. The following steps SY3 and SY4 are repeated to see whether or not the EXECUTE key 124 has operated and whether or not the CANCEL key 126 has operated, respectively. When the CHECK lamp 122 is turned on, the operator reads the value of a measurement indicated on a display 123 to judge whether or not the value is within a statistically ordinary range. If the judgement is affirmative, that is, if the value displayed is not extraordinary, the operator will operate the EXECUTE key 124. On the other hand, if the judgement is negative (NO), that is, if the value is an extraordinary one, the operator will operate the CANCEL key 126. The erroneous measurements resulting in the extraordinary value could have been caused due to noises or physical activities of the subject's body, for example. From his technical knowledge, the operator can read extraordinary values that exceed the physiologically maximum and minimum values, or that exceeds values possibly expected on the living body from the absence or presence of the physical activities, the operating conditions of an electric knife during a surgical operation and/or the like.

In the case where the judgement at step SY3 is affirmative, step SY3 is followed by step SY5 to determine the traveling path of the pen 38 for recording the selected indicia at its recording position according to the detection signal supplied from the automatic blood pressure monitor 10. Also are generated respective drive signals to cause the drive circuits 56, 58 and 60 to move the pen 38 along the traveling path determined. However, in the case where the judgement at step SY4 is affirmative, step SY6 is subsequently executed to cancel the detection signal representative of living body information supplied from the blood pressure monitor 10, and at the following step SY7 a measurement signal MS is outputted to cause the monitor 10 to conduct a re-measuring operation. Thus, the periodic measuring operations with the automatic blood pressure monitor 10 are interrupted by the measurement signal MS, and the monitor 10 immediately starts a re-measuring operation so as to supply, to the X-Y plotter 22, another detection signal representative of the living body information newly obtained. In this embodiment, the CANCEL key 126, ROM 54 storing the program indicated by the flow chart of FIG. 25, CPU 50 working according to the flow chart of FIG. 25, RAM 52 and others cooperate with each other to serve as operator-controlled means for inhibiting the X-Y plotter 22 from recording the indicia. Meanwhile, the ROM 54 storing the program of step SY7 shown in FIG. 25, CPU 50 working according to the step SY7, RAM 52 and others serve as another operator-controlled means for re-activating the monitor 10 to obtain another measurement when a measurement is erroneous. The EXECUTE key 124 and CANCEL key 126 are utilized for commanding the X-Y plotter 22 to conduct a recording and not to conduct a recording, respectively.

As described hitherto, in the present embodiment, erroneous measurements resulting from noises or physical activities of a living body can be canceled by operation of the CANCEL key 126, providing a higher reliability about the data recorded on the record sheet 18. The control device 16 determines the current time at which a measurement is made by the blood pressure monitor 10 and the recording position at which is recorded the indicia indicative of the value of the measurement. The indicia indicative of the time and value is automatically recorded by the X-Y plotter 22 at the recording position. That is, this embodiment products the same basic advantages as the preceeding embodiments.

Furthermore, in this embodiment, the operation of the CANCEL key 126 for canceling an erroneous measurement causes, at the same time, generation of a measurement signal MS to re-activate the blood pressure monitor 10. As a result, a good measurement can be obtained through another measurement immediately after a possibly erroneous measurement due to noises or physical activities of living body, for example. In other words, the problem of lacking of the measurements due to erroneous measurements is eliminated.

Figure 26:
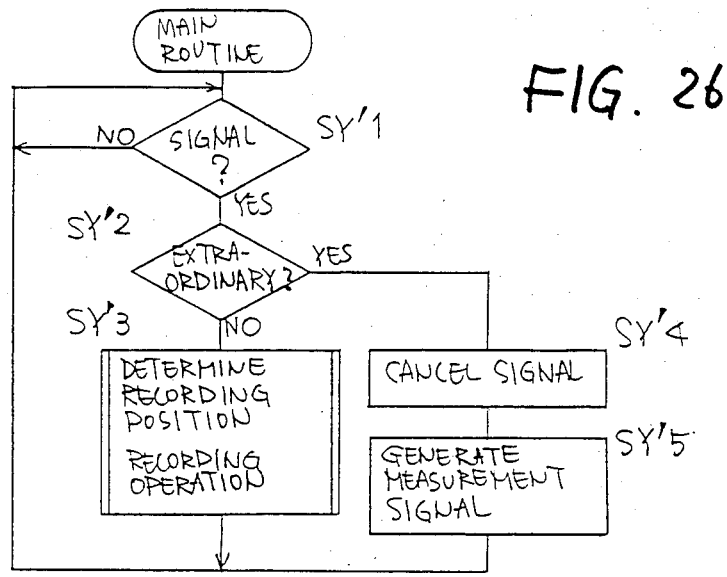
FIGS. 26 and 27 are a flow chart showing the operation of a control device used in different preferred forms of the embodiment of FIG. 22, respectively.

The control circuit for the X-Y plotter 22 of this embodiment may be operated according to a flow chart shown in FIG. 26, in place of the flow chart of FIG. 25. At the first step SY'1 of the flow chart of FIG. 26 corresponding to step SY1 of FIG. 25, it is judged whether or not there has been inputted a record signal supplied from the control device 16 representing the value of a measurement obtained by the blood pressure monitor 10. If the judgement at step SY'1 is affirmative (YES), step SY'1 is followed by step SY'2 to automatically judge whether or not the value represented by the detection signal is an extraordinary one, based on pre-stored reference range information. The reference range corresponds to the most wide range that is physiologically expected. In the case where the judgement at step SY'2 is negative (NO), step SY'3 similar to step SY5 of FIG. 25 is executed to record the indicia at the recording position according to the signal entered. On the other hand, in the case where the judgement at step SY'2 is affirmative, steps SY'4 and SY'5 similar to respective steps SY6 and SY7 of FIG. 25 are executed to cancel the signal entered and generate a measurement signal MS. The above-described flow chart can permit cancellation of the record signal representative of erroneous measurement at steps SY'2, SY'4 and SY'5, providing the same effects as the flow chart of FIG. 25. This flow chart can replace the EXECUTE and CANCEL key 124 and 126 and the technical judgements by the operator. In the instant embodiment operated according to the flow chart of FIG. 26, the ROM 54 storing programs corresponding to steps SY'2, SY'4 and SY'5, CPU executing those steps SY2', SY'4 and SY'5, RAM 52 and other members serve as judging means, inhibiting means and reactivating means.

Figure 27:
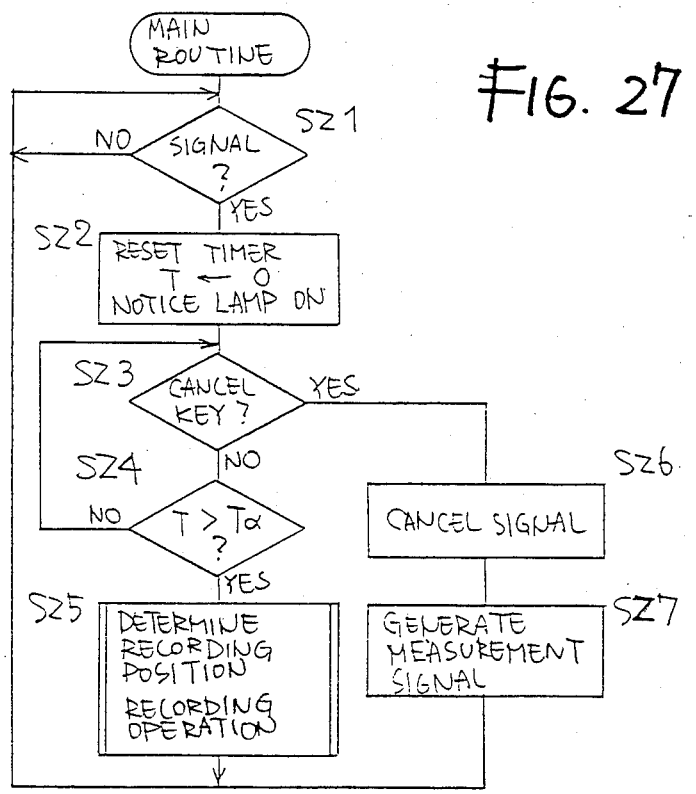

In place of the flow chart of FIG. 25 for the control circuit of the X-Y plotter 22, a flow chart shown in FIG. 27 may be employed. At step SZ1 of the flow chart similar to step SY1 of FIG. 25 is started to check whether or not there has been a record signal from the control device 16. If the judgement at step SZ1 is affirmative (YES), step SZ1 is followed by step SZ2 to reset the content of a timer T to "0" and turn on, in place of the CHECK lamp 122, a NOTICE lamp (not shown) for noticing a recording of the selected indicia corresponding to the record signal entered. The timer T counts reference pulses following the above-described resetting thereof. Therefore the content of the timer T represents an elapsed time following the resetting. The next step SZ3 is executed to see whether or not the CANCEL key 126 has been operated. If the judgement at step SZ3 is negative, step SZ3 is followed by step Z4 wherein it is judged whether or not the content of the timer T has exceeded a predetermined value, Tα. In this embodiment, the value of Tα is predetermined to be approximately one minuite. When the NOTICE lamp is turned on, the operator reads the value of a measurement indicated on the display 123 of the monitor 10. If the value is not extraordinary, the operator does not have to do anything. If the value is extraordinary, the operator should operate the CANCEL key 126. If nothing has been done, step SZ5 is subsequently executed to determine the recording position for the selected indicia corresponding to the record signal and to record the indicia at the recording position in the two dimensional chart area 20. However, if the value is extraordinary, and, if the CANCEL key 126 has been operated, steps SZ6 and SZ7 similar to respective steps SY6 and SY7 are executed to cancel the record signal and to generate a measurement signal MS. Therefore, the flow chart of FIG. 27 permits cancellation of signals representative of erroneous measurements at steps SZ3, SZ6 and SZ7, providing the same advantageous effects as in the preceding two forms of the present embodiment.

While in the present embodiment the CPU 50 of the X-Y plotter 22 is adapted to execute the flow chart shown in FIGS. 25, 26 or 27, the CPU 64 of the control device 16 may be adapted to execute the flow chart, to command the control circuit of the X-Y plotter 22 to operate or inhibit a recording, in place of the CPU 50.

EXAMPLE V

There will be described another embodiment of the invention.

Figure 28:
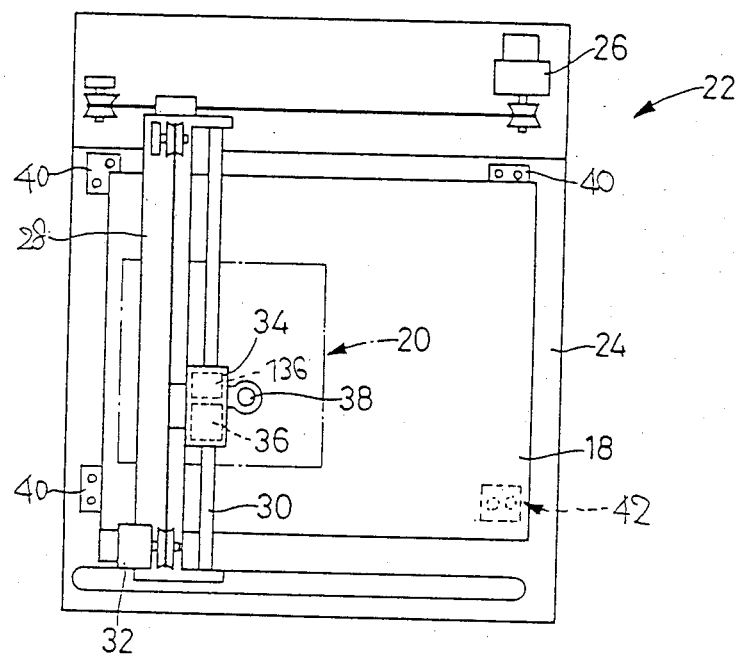
FIG. 28 is a view, corresponding to FIG. 3, showing an X-Y plotter of a still further embodiment of the apparatus.
Figure 29:
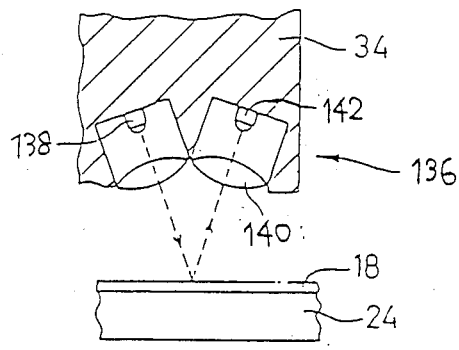
FIG. 29 is a view showing a photosensor disposed on a carriage of the X-Y plotter of FIG. 28.
Figure 30:
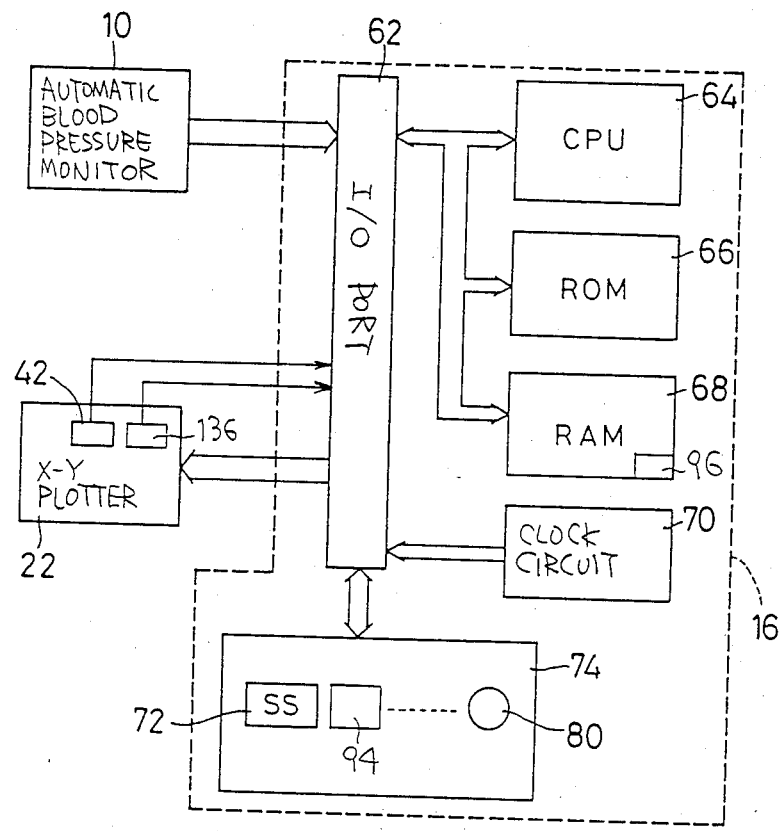
FIG. 30 is a block diagram, corresponding to FIG. 6, showing a construction of a control device in the apparatus of FIG. 28.

Referring to FIG. 28, there is provided a photosensor 136 on the carriage 34 of the X-Y plotter 22. The photosensor 136 detects a line printed on a recording sheet 18. Referring to FIG. 29, the photosensor 136 includes a light emitter 138 for emitting light beams having a specific wavelength or a specific modulated frequency, and a light receiver 142 for receiving light beams reflected by the record sheet 18 through a lens 140. The photosensor 136 detects the printed line based on the degree of intensity of the light beams from the recording sheet 18 and supplies a line signal representative of the position of the line, to a control device 16 as shown in FIG. 30. The lens 140 forms a partial picture of the record sheet 18 into an image on the light receiver 142.

Furthermore, in another mode of this embodiment, optical fiber cable may be connected its one end to the light receiver 142, which is fixed to the side portion of the X-Y plotter 22, while its another end is positioned to a place where the light emitter 138 is fixed, or a place where the record sheet 18 lies down slightly below. In this case, the optical fiber cable is arranged in the same manner of flexible flat cable (not shown) comprised in order to supply electoric power to the up/down solenoid 36.

The control device 16 of this embodiment is adapted to be operated according to a flow chart similar to that of FIG. 7. However, the step of initialization includes a chart area detecting routine shown in FIG. 31 wherein the location and size of the two dimensional chart area 20 are automatically detected or measured, and stored.

The chart area detecting routine of FIG. 31 is for automatically detecting the location and size of the chart area 20 by means of causing the photosensor 136 to scan the surface of the record sheet 18. First, at step SK1 of the routine, a signal to locate the pen 38 at its initial position is supplied to the X-Y plotter 22, and the carriage 34 is moved to its initial position, for example, point (X0, Y0) at the left and lower corner (FIG. 28) of a movement area in which the carriage 34 is movable. And the contents of an X register and a Y register are cleared up to "zero", respectively. The content of the X register is added and subtracted by the value of one each time the carriage 34 is moved by one step in the positive and negative direction along the X axis 78, respectively. Similary, the content of the Y register is added and subtracted. At the following step SK2, the carriage 34 is moved in the Y direction to a point (X0, Xc) which is assumed to correspond to the middle point of the axis of ordinate 76 of the chart area 20. At next step SK3, the carriage 34 is moved in the X direction. When the photosensor 136 detects a line printed on the record sheet 18, it generates a pulse signal corresponding to the detected line to an I/O port 62 of the control device 16. Since the two dimensional chart area 20 is a graph ruled into squares (e.g., three millimeters squares) as shown in FIG. 2, the photosensor 136 periodically generates pulse signals while the carriage 34 are passing over the chart area 20. At step SK4 are stored the positions of points (X1, Yc) and (X2, Yc) respectively corresponding to the first and last pulse signals of the regularly successive pulse signals, that is, the pulse signals at equal intervals.

Figure 32:
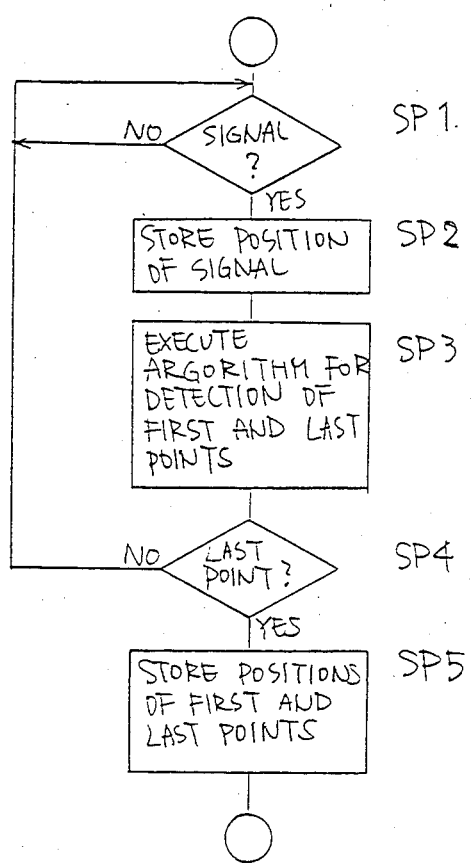

At step SK4 is executed a first/last pulses detecting routine as shown in FIG. 32. At step SP1 of this routine, it is judged whether or not the photosensor 136 has generated a pulse signal. If the judgement at step SP1 is negative (NO), step SP1 is repeated until a pulse signal is generated. If a pulse signal is generated by the photosensor 136, that is, if the judgement at step SP1 becomes affirmative (YES), step SP1 is followed by step SP2 to store the position of the carriage 34 at the time the pulse signal is generated. The contents of the X and Y registers at the time the pulse signal is generated are stored as the position of the carriage 34. At the following step SP3, algorithm is executed for detecting the pulse signals corresponding to the first or last line of the equally spaced lines. Step SK3 is followed by step SK4 wherein it is judged whether or not the pulse signal corresponding to the last line of the equally spaced lines is generated. In the case where the judgement at step SK4 is negative, step SK4 is backwardly followed by step SK1, while in the case where the judgement at step SK4 is affirmative step SK5 is subsequently executed to store the positions of points (X1, Yc) and (X2, Yc) of the carriage 34 respectively corresponding to the first and last pulse signals of the equally spaced pulse signals.

Back to the flow chart of FIG. 31, at step SK5, the carriage 34 is moved in the X direction to point (Xc, Y0) which is assumed to face the middle point of the time axis 78 of the two dimensional chart area 20. At the following step SK6, the carriage 34 is moved in the Y direction. Step SK6 is followed by step SK7 to store the positions of points (Xc, Y1) and (Xc, Y2) of the carriage 34 at the time the first and last pulse signals of the pulse signals equally spaced are generated by the photosensor 136.

Finally, at step SK8, the stored positions of points (X1, Yc), (X2, Yc), (Xc, Y1) and (Xc, Y2) are utilized to determine the positions of points P1(X1, Y1), P2(X2, Y2), P3(X3, Y3) and P4(X4, Y4) at the four corners of the two dimensional chart area 20, based on the supposition that the axes of abscissa and ordinate 78 and 76 of the two dimensional chart area 20 are parallel to the X and Y directions of the X-Y plotter 22, respectively, in which the carriage 34 is moved. At step SK8, those positions at the four corners of the chart area 20 are stored in a chart area storing region 96 of the RAM 68 (FIG. 30). The positions of points P1, P2, P3 and P4 represent the location and size of the chart area 20. Therefore, in this embodiment, the photosensor 136, CPU 64 executing the chart area detecting routine of FIG. 31, RAM 68 and others cooperate with each other to serve as chart area detecting means.

Subsequently are executed steps similar to step S2 and the following steps of FIG. 7, for determining the indicia to be recorded and the recording position in the chart area 20, based on a detection signal supplied by the automatic blood pressure monitor 10 and the current time at which the signal is supplied, and for actually recording the selected indicia at its recording position.

The full-scale values for the axes of abscissa and oridinate 78 and 76 of the chart area 20 are pre-stored in this embodiment. Further, if there is a distance between the position at which the detecting operation of the photosensor 136 is made, and the position at which the recording operations of the pen 38 is made, the distance is taken into consideration, that is, compensated by a suitable method.

In the present embodiment, the actual location and size of the two dimensional chart area 20 is automatically detected by the photosensor 136 disposed on the carriage 34 and other members, and stored in the chart area storing region 96. In the thus obtained chart area 20 the indicia representative of living body information is recorded at the recording position. Therefore this embodiment provides reliable recordings of indicias on the record sheet 18, in spite of possibly out-of-place printings of the chart area 20 on the sheet 18, variation of the location of the chart area 20 on the sheet 18 due to shrinkage or expansion of the sheet 18, out-of-place placements of the sheet 18 onto the support 24, or the like. In the embodiment, the control device 16 determines the current time at which a measurement is made by the monitor 10 and the recording position in the chart area 20 for the indicia corresponding to the measurement, while the X-Y plotter 22 automatically records the selected indicia at the recording position determined, like the preceding embodiments.

Since the record sheet 18 is directly placed on the support 24, auxiliary items, such as the names of medicines administered and the times at which the medicines are administered, can be noted in suitable positions on the same record sheet 18, directly by hand, even if the X-Y plotter 22 is in operation for automatical recording.

The present embodiment provides various applications.

While the chart area detecting means of this embodiment includes the photosensor 136 for detecting the two dimensional chart area 20, the photosensor 136 may be replaced by a magnetic sensor (not shown) disposed on the carriage 34 which detects lines printed on the sheet 18 with magnetic ink. Furthermore, the chart area detecting means may be arranged such that the two dimensional chart area 20 may have at the four corners thereof marks or holes which can be detected by well known mechanical means, electric means, electromagnetic means, or photoelectric means and that each hole or mark at the corner of the chart area 20 is automatically detected.

The location and size of the two dimensional chart area 20 may be detected by means of two scannings of the photosensor 136 along two spaced imaginary lines parallel to the Y direction together with two scannings of the same 136 along two spaced imaginary lines parallel to the X direction, in place of two scannings of the photosensor 136 across the central portion of the chart area 20, one scanning in the X direction and the other in the Y direction. This method permits detection of the inclination and deformation of the two dimensional chart area 20 as well as its location and size, resulting in still higher exactitude in recording indicias.

Further, in the case where the two dimensional chart area 20 having a specific size is exactly printed at predetermined distances from the side edges of the record sheet 18, the chart area 20 can be indirectly detected by means of detecting the side edges of the sheet 18 with the photosensor 136. This indirect method may be employed in this embodiment, in place of the direct method described above.

EXAMPLE VI

There will be described yet another embodiment of the invention.

Figure 33:
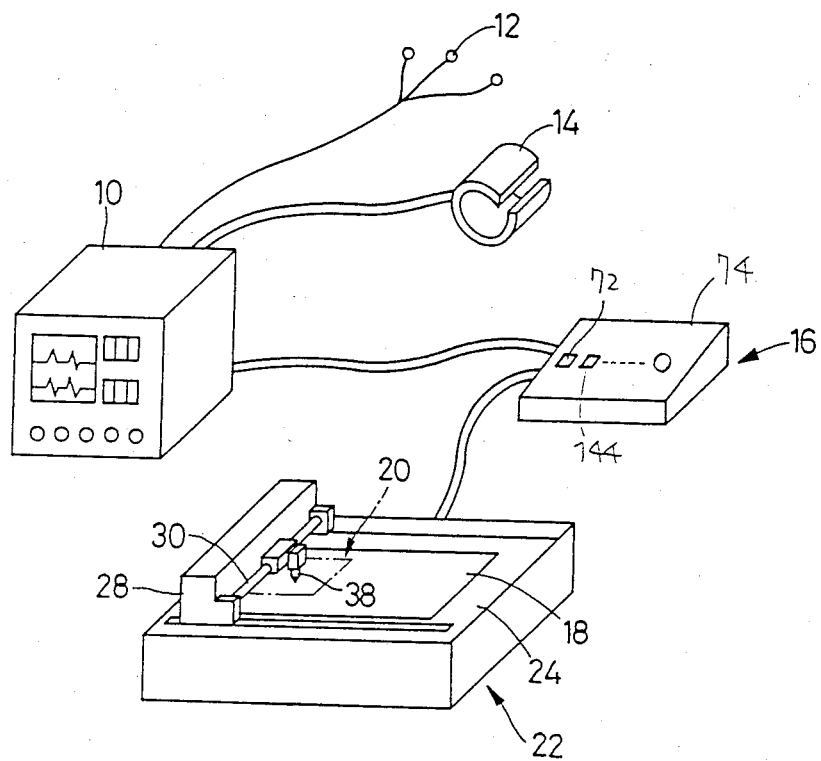
FIG. 33 is a view, corresponding to FIG. 1, showing a general arrangement of another embodiment of the apparatus of the invention.
Figure 34:
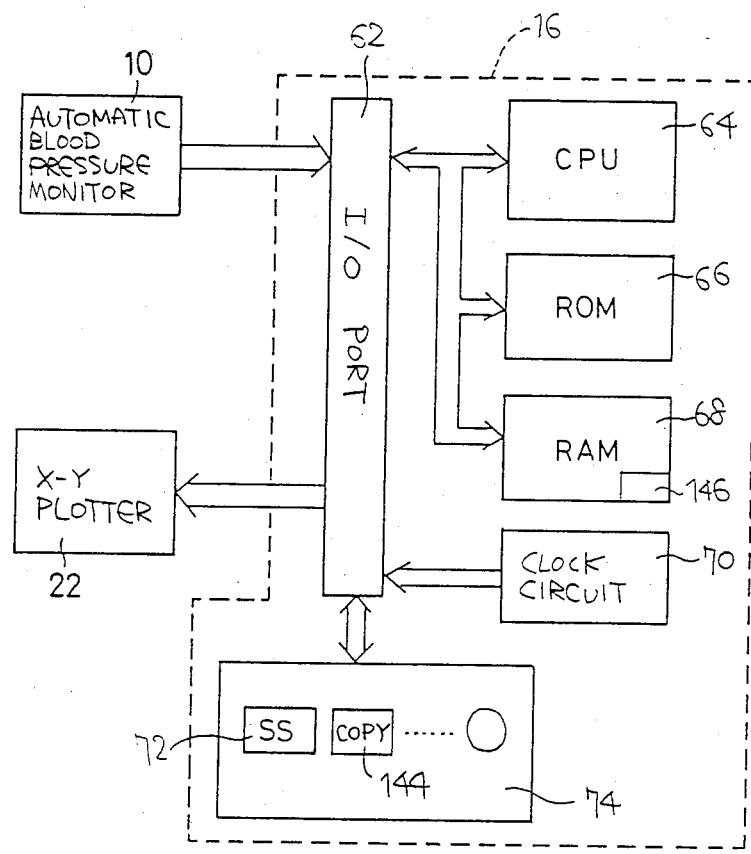
FIG. 34 is a block diagram, corresponding to FIG. 6, showing a construction of a control device of the apparatus of FIG. 33.

Referring to FIGS. 33 and 34, an input console 74 of a control device 16 includes a COPY key 144. A RAM 68 includes a record data storing region 146.

Figure 35:
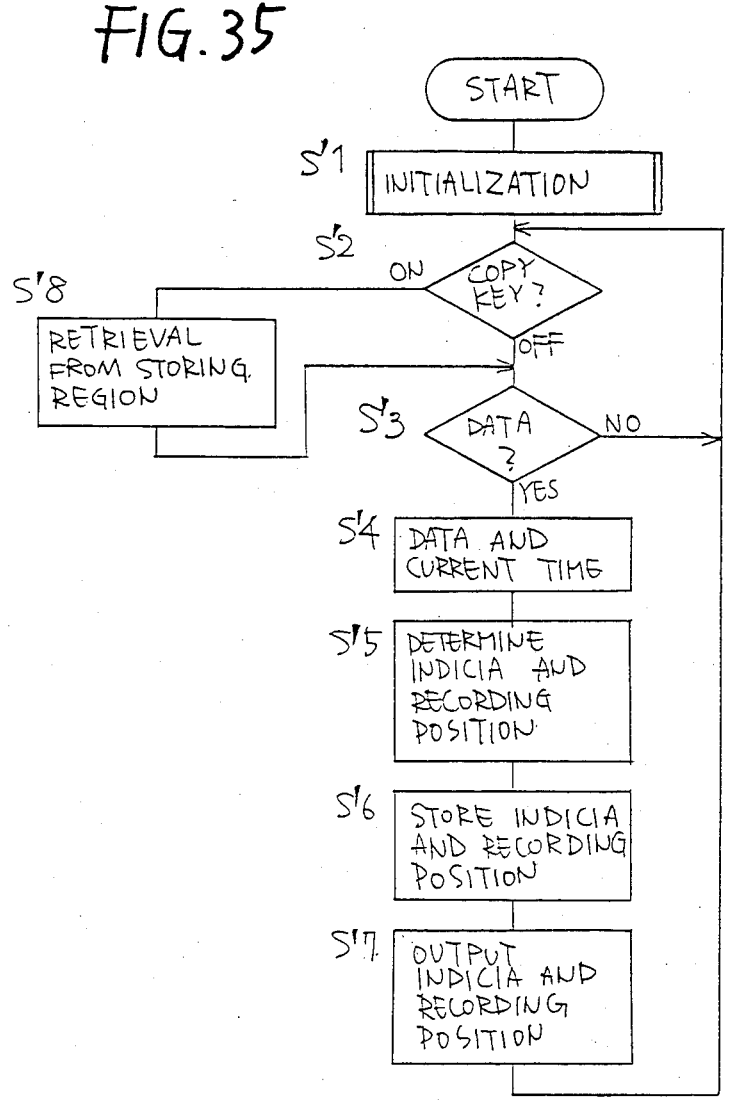
FIG. 35 is a flow chart, corresponding to FIG. 7, showing the operation of the control device of FIG. 34.

The operation of the control device 16 will be described hereinafter with reference to a flow chart shown in FIG. 35. This flow chart represents a control routine which is executed upon depression of a start/stop pushbutton 72. The control routine is stopped upon the next depression of the start/stop pushbutton 72.

In general, prior to depression of the start/stop pushbutton 72, an automatic blood pressure monitor 10 is activated to be ready for periodically measuring maximum and minimum blood pressure, heart rate, breathing rate, and the like of a subject. Upon depression of the start/stop pushbutton 72, step S'1 similar to step S1 of FIG. 7 is executed for initialization. At the following step S'2, it is judged whether or not the COPY key 144 has been operated. Since the COPY key 144 has not been operated at the beginning, step S'3 similar to step S2 of FIG. 7 is executed. In the case where the judgement at step S'3 is affirmative (YES), that is, where a detection signal is entered from the automatic blood pressure monitor 10, are successively executed steps S'4, S'5, S'6 and S'7 respectively similar to steps S3, S4, S5 and S6 of FIG. 7, so as to record the indicia corresponding to the detection signal, at the recording position in a two dimensional chart area 20.

After repetition of execution steps described above, the indicia indicating maximum and minimum blood pressure and other indicias indicating other measurement items are recorded along the time axis 78 of the two dimensional chart area 20 as shown in FIG. 2. In other words, timewise varying trends of items of living body information are recorded on the chart area 20. Further, record signals which indicate the selected indicias and their recording positions and which are supplied to the X-Y plotter 22 are stored one by one in the record data storing region 146 of the RAM 68.

If an indicia being currently recorded in the two dimensional chart area 20 becomes scratchy due to, for example, drying-up or shortness of ink with the pen 38, the COPY key 144 is operated to re-record the indicia for assuring a clear reading. Also, for obtaining a copy of the recorded chart area 20, the COPY key 144 is operated after the record sheet 18 with the recorded chart area 20 is removed from top of a plurality of record sheets 18 laid one upon another, or replaced by another record sheet 18. Upon operation of the COPY key 144 in the cases described above for example, the judgement at step S'2 turns affirmative (YES), and step S'2 is followed by step S'8 to re-record the indicias representative of items of living body information in the two dimensional chart area 20, according to the record signals which have already caused recordings of the same indicias in the chart area 20 and which have been stored in the record data storing region 146 at step S'6. In other words, step S'8 is executed to re-record the timewise varying trends of items of living body information. An operation of the COPY key 144 results in providing in copy of the recorded chart area 20. Therefore, in the present embodiment, the record data storing region 146 corresponds to memory means for storing record signals representative of the kinds of indicias which have once recorded in the chart area 20 and of their recording positions at which the indicias have been actually recorded. The COPY key 144 corresponds to operator-controlled means for commanding re-recording. The ROM 66 storing programs corresponding to steps S'2 and S'8, CPU 64 executing those steps S'2 and S'8, and RAM 68 cooperate with each other to serve as re-recording control means.

As described hitherto, on this embodiment of the invention, operation of the COPY key 144 permits execution of recording in the two dimensional chart area 20. Therefore, in the case where an indicia being currently recorded become scratchy or blurred due to drying-up or shortness of ink with the pen 38, the COPY key 144 is operated to command re-recording for assuring a clear recording. In the meantime, the present embodiment produces preferable effects similar to those of the preceding embodiment, because the control device 16 determines the recording position for an indicia which corresponds to a detection signal supplied from the automatic blood pressure monitor 10, together with the current time at which the signal is supplied, and because the X-Y plotter 22 automatically records the selected indicia at the recording position determined.

In the case where a plurality of copying or carbon sheets laid one upon another are used in this embodiment, the required number of copies are obtained by means of operating the COPY key 144 after removing the record sheet 18 on top of the stacked sheets 18 on which the indicias have been already recorded. An operation of the COPY key 144 causes the pen 38 to move along the same traveling path as that for the last recording so as to re-record a copy. In this connection, manually recorded living body information items other than automatically recorded one are clearly transferred from the recording sheet 18 on top to the next sheet 18 below, under comparatively large writing forces.

Further, in the case where the plural kinds of indicias corresponding to the respective items of living body information are recorded with different colors, a copy is available with each indicia having a corresponding color, in this embodiment.

Although the X-Y plotter 22 of this embodiment repeats recording of living body information in the two dimensional chart area 20 upon operation of the COPY key 144, it is appreciated that the COPY key 144 may be replaced with other means for commanding re-recording, such as pedal means or voice-responsive means.

Moreover, while the CPU 64 provided for the control device 16 is utilized in the embodiment to control, responsive to operation of the COPY key 144, re-recording of living body information, it is possible to use another CPU, such as the CPU 50 of the control circuit for the X-Y plotter 22, so as to cause the X-Y plotter 22 to re-record living body information in response to a signal supplied from the COPY key 144. This arrangement requires the ROM 54 of the control circuit for the X-Y plotter 22 to store programs corresponding to steps S'2 and S'8, and the RAM 52 of the same to have a region corresponding to the record data storing region 146.

EXAMPLE VII

There will be described another embodiment according to the present invention.

Figure 37:
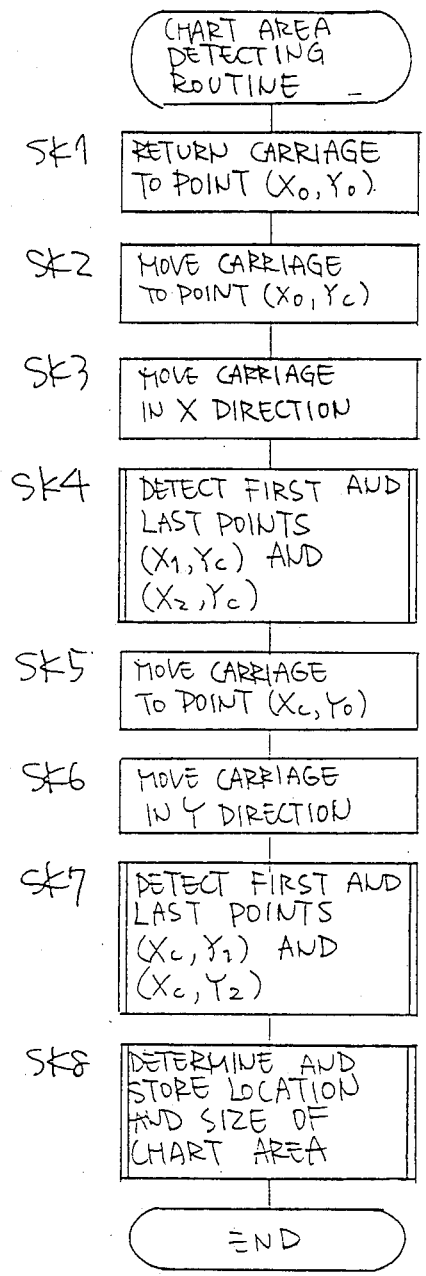
FIG. 37 is a view, corresponding to FIG. 3, showing an X-Y plotter of the apparatus of FIG. 36.
Figure 36:
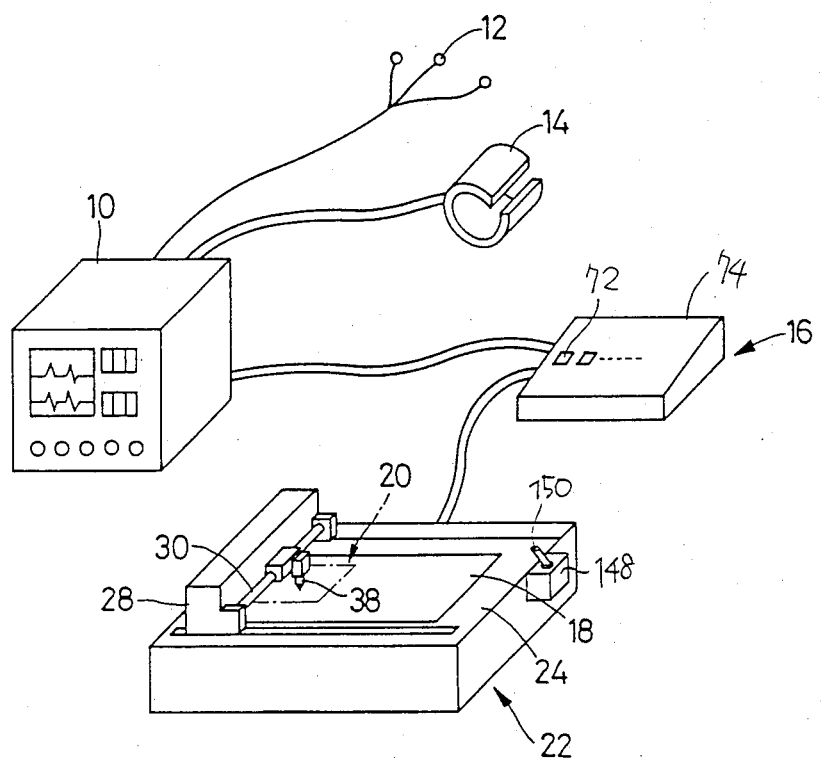
FIG. 36 is a view, corresponding to FIG. 1, showing a general arrangement of still another embodiment of the apparatus of the invention.
Figure 37:
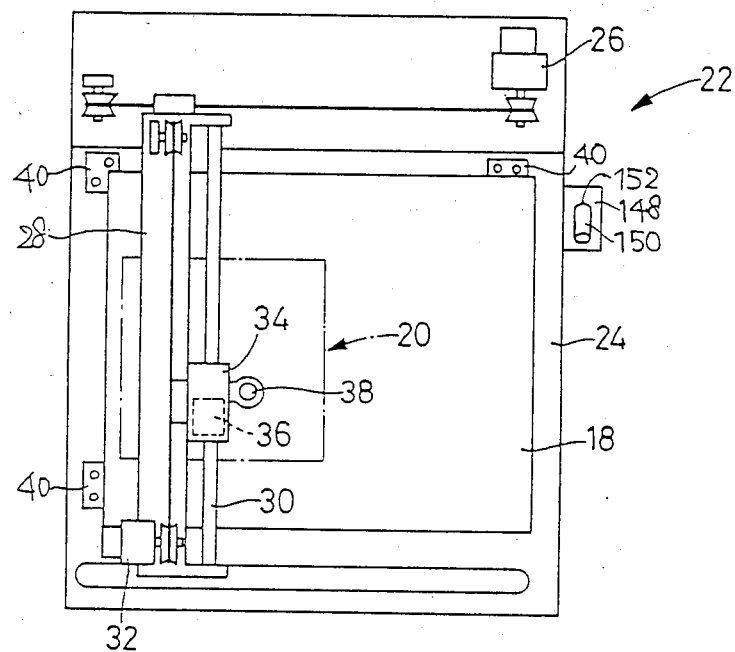
Figure 38:
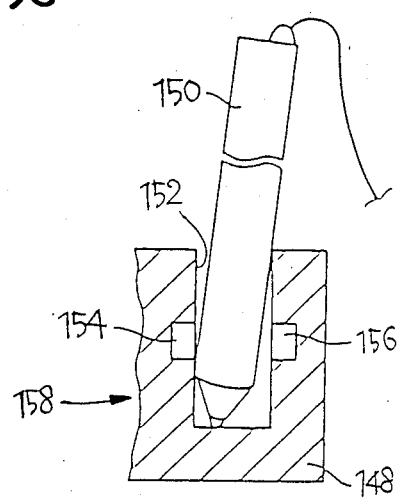
FIG. 38 is a view showing a pen sensor which is disposed on the X-Y plotter of FIG. 37.

Referring to FIGS. 36 and 37, there is shown a pen stand 148 fixed to a side wall of an X-Y plotter 22. As shown in FIG. 38, the pen stand 148 has a holder hole 152 for holding a marker or a a writing pen 150, and a pen sensor 158 disposed in the hole 152 and including a light emitter 154 and a light receiver 156. The writing pen 150 is used for manual recording in an accessory area on an anesthesia record sheet 18. The pen sensor 158 detects the absence or presence of the writing pen 150 in the holder hole 152 of the pen stand 148. The absence of the pen 150 from the holder hole 152 means that the pen 150 is currently in use for mannual recording operation. Therefore, the writing pen 150 and pen sensor 158 cooperate with each other to serve as a manual-recording state detector of this embodiment. The pen sensor 158 generates a signal when the light receiver 156 receives light beams emitted by the light emitter 154. The signal generated by the sensor 158 corresponds to a mannual recording signal.

Figure 39:
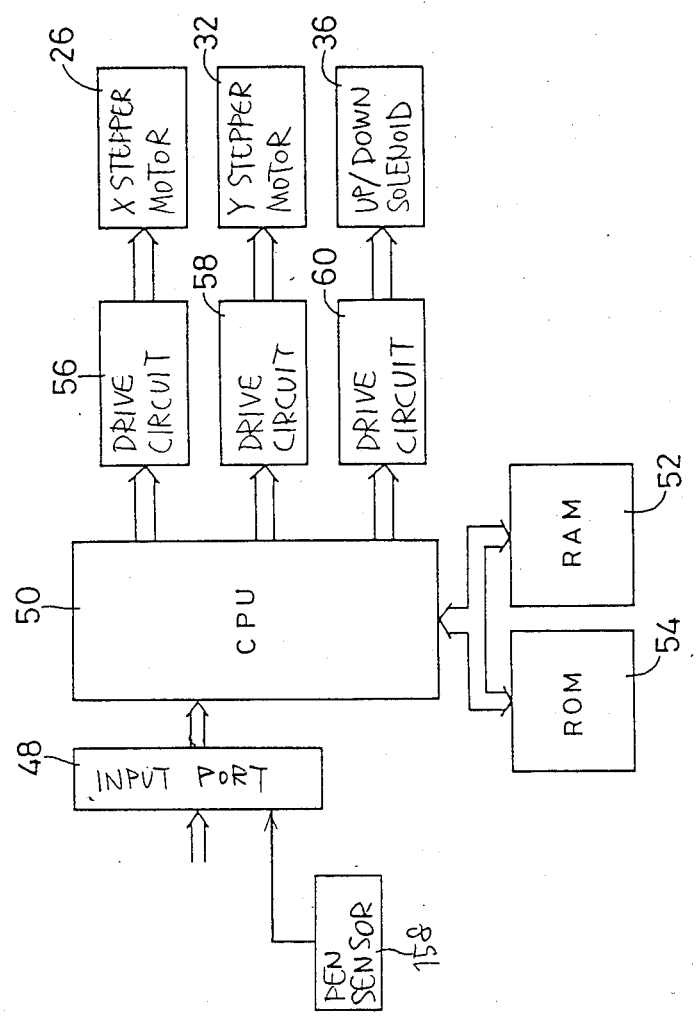
FIG. 39 is a block diagram, corresponding to FIG. 5, showing a control circuit for the X-Y plotter of FIG. 37.

Referring to FIG. 39, there is illustrated a control circuit of an X-Y plotter 22 of this embodiment. The control circuit includes an X stepper motor 26, Y stepper motor 32 and up/down solenoid 36 which cooperate with each other to move a pen 38 for effecting automatic recordings. The automatic recordings are permitted while is absent the manual recording signal from the pen sensor 158 which indicates that the manual pen 150 is not held in the holder hole 152 of the pen stand 148, that is, while the light receiver 156 does not detect the light beams emitted from the light emitter 154. On the other hand, while the manual recording signal is present, that is, while the light receiver 156 detects the light beams emitted by the light emitter 154, a CPU 50 generates drive signals to cause the pen 38 to be moved to its retracted position where the pen 38 does not interfere with the operator's mannual recording using the writing pen 150.

The X-Y plotter 22 is operated according to a main routine similar to that indicated by the flow chart of FIG. 20. The main routine of this embodiment is periodically, for example, at intervals of 10 msec. interrupted by an interrupt routine shown in FIG. 40. At step SW'1 of this interrupt routine, it is judged whether or not the writing pen 150 is currently used by the operator's hand, depending upon the presence or absence of the signal from the pen sensor 158. If the judgement at step SW'1 is negative (NO), the interrupt routine is over. If the judgement at step SW'1 is affirmative (YES), step SW'1 is followed by step SW'2 wherein is generated a drive signal to cause the pen 38 to be moved to its initial position, i.e., its retracted position where the pen 38 does not interfere with the operator's hand having the mannual writing pen 150 to write down the auxiliary items of living body information.

Thus, the operator can record the titles of medicines and the names of treatments in suitable areas on the record sheet 18 without interference by the recording pen 38, even while the X-Y plotter 22 is in the automatic recording state. This is because, if the writing pen 150 is lifted out of the pen stand 148 by the operator, the recording pen 38 currently effecting automatic recording is immediately all retracted to its initial or retracted position. While the writing pen 150 is out of the pen stand 148, the pen 38 is not permitted to be moved from its retracted position even though the X-Y plotter receives a record signal representative of the indicia to be recorded and its recording position that is generated by the control device 16 constructed as shown in FIG. 41. Consequently, the operator can do his recording operation without interference by the recording pen 38. Therefore, the ROM 54 storing program corresponding to the flow chart of FIG. 40, CPU 50 executing the program and RAM 52 cooperate with each other to serve as retraction control means for causing the carriage 34 to be retracted to its retracted position so as not to interfere with the operator's hand above the support 24.

Figure 40:
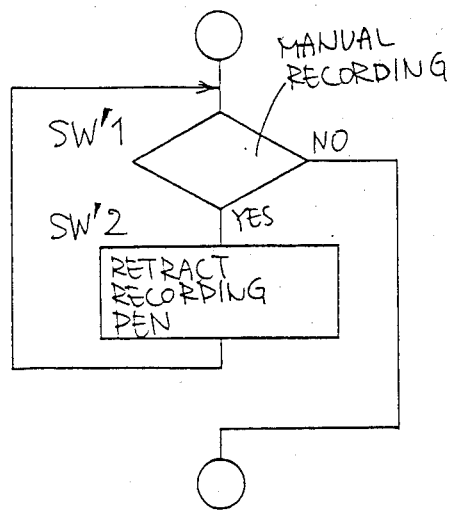
FIG. 40 is a flow chart showing the operation of the control circuit of FIG. 39.
Figure 41:
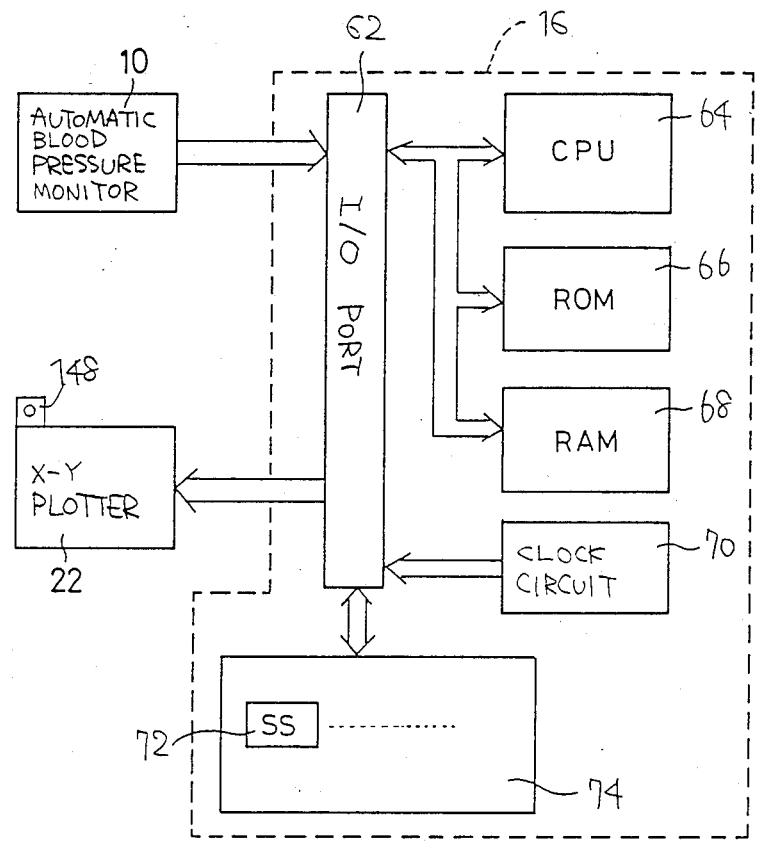
FIG. 41 is a block diagram, corresponding to FIG. 6, showing a construction of a control device in the apparatus of FIG. 36.

As described hitherto, in this embodiment, step SW'2 of FIG. 40 is executed to cause the carriage 34 to be retracted to its initial (retracted) position, upon detection of the manual pen 150 taken out of the pen stand 148 by the pen sensor 158 as the manual recording state detector. In this way, it reliably prevents the recording pen 38 from interfering with the operator's hand effecting manual recording. In other words, if the operator takes the manual pen 150 out of the pen stand 148 for performing manual recording on the record sheet 18 while the carriage 34 of the X-Y plotter 22 is working for automatic recording, the carriage 34 is immediately retracted to its initial (retracted) position where the carriage 34 does not interfere with the operator's hand using the writing pen 150. Further, the X-Y plotter 22 does not cause the carriage 34 to be moved from the retracted position during the mannual recording state, resulting in no possibility of interference with the operator's hand by the carriage 34. Thus, the operator is made free from mental pressure he may feel when he must do manual recording on the record sheet 18 placed on the support 24 with possibility of starting of the plotter 22. The control device 16 of this embodiment determines the current time at which the automatic blood pressure monitor 10 obtains a measurement, and the recording position in the two dimensional chart area 20 for the indicia corresponding to the value of the measurement. The X-Y plotter 22 automatically records the selected indicia indicative of the measurement value and the current time at the recording position determined. Therefore, this embodiment produces the same effects as those of the previous embodiments.

In the present embodiment, the carriage 34 and the recording pen 38 of the X-Y plotter 22 are retracted to its initial position each time an automatic recording based on a record signal from the control device 16 is completed. As a result, the operator can read the records on the record sheet 18 with ease, especially on the two dimensional chart area 20. In this connection, the carriage 34 may be retracted to some other position where the carriage 34 does not interfere with the operator's reading, in place of its initial position.

Figure 42:
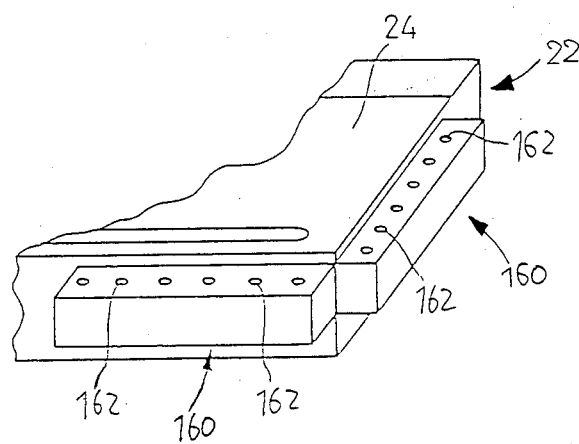
FIG. 42 is a view showing a manual-recording state detector employed in a preferred form of the embodiment of FIG. 36.

Referring to FIG. 42, there is illustrated a photoelectric sensor array of reflection type 160 utilized as the manual recording state detector, in place of the pen sensor 158. As shown in the figure, the photoelectric sensor array 160 includes photoelectric sensors of reflection type 162 each of which consists of a light emitter for emitting light beams upward and a light receiver for sensing reflected light beams from upward. The array of photoelectric sensors 160 is diposed along the periphery of the support 24. In the case where the operator's hand is moved over the X-Y plotter 22 across the periphery of the same for mannual recording on the record sheet 18, at least one of the photoelectric sensors 162 senses the movement of the operator's hand. Consequently, a signal indicative of that movement of the operator's hand is supplied from the sensor 160 to an input port 48 of a control circuit for the X-Y plotter (FIG. 39) in this arrangement. It is appreciated that the writing pen 150 is not limited to a specified one, i.e., other pens are usable for the mannual recording.

While the recording pen 38 is retracted to its initial position upon detection of the mannual recording state by the mannual recoding state detector, the pen 38 may be retracted to a left and upper position in FIG. 37, for example. Alternatively, it is possible that the movable member 28 is moved to its retracted position while the carriage 34 is not moved. A single requirement is such that the carriage 34 does not interfere with the operator's hand.

Furthermore, in place of the pen sensor 158 or reflection photoelectric sensor array 160 is mentioned above, other sensors such as an ultrasonic sensor, infrared-ray sensor, capacitance sensor may be employed for detecting the mannual recording state.

The detector for detecting the mannual recording state may be disposed on a desk on which the X-Y plotter 22 is placed, an object around the desk such as a chair or the movable member 28 or carriage 34 of the X-Y plotter 22, other than on the periphery of the X-Y plotter 22. The movable member 28 or carriage 34 may be adapted to keep a predetermined distance from a movable operator's hand, unlike the above mentioned method in which the movable member 28 or the carriage 34 is retracted to a suitable position. The above-identified predetermined distance corresponds to a detectable distance of the detector, and therefore the retracted position of the recording pen 38 is movable depending upon the operator's hand.

While the CPU 50 provided in the X-Y plotter 22 is utilized as control means for controlling the retraction of the carriage 34 in this embodiment, an external CPU, for example, CPU 64 for the control device 16 may be used. In this case, the CPU 64 commands, based on a signal from the pen sensor 158, the control circuit of the X-Y plotter 22 to cause the carriage 34 to be retracted to its retracted position.

EXAMPLE VIII

There will be described yet another embodiment according to the invention.

Figure 43:
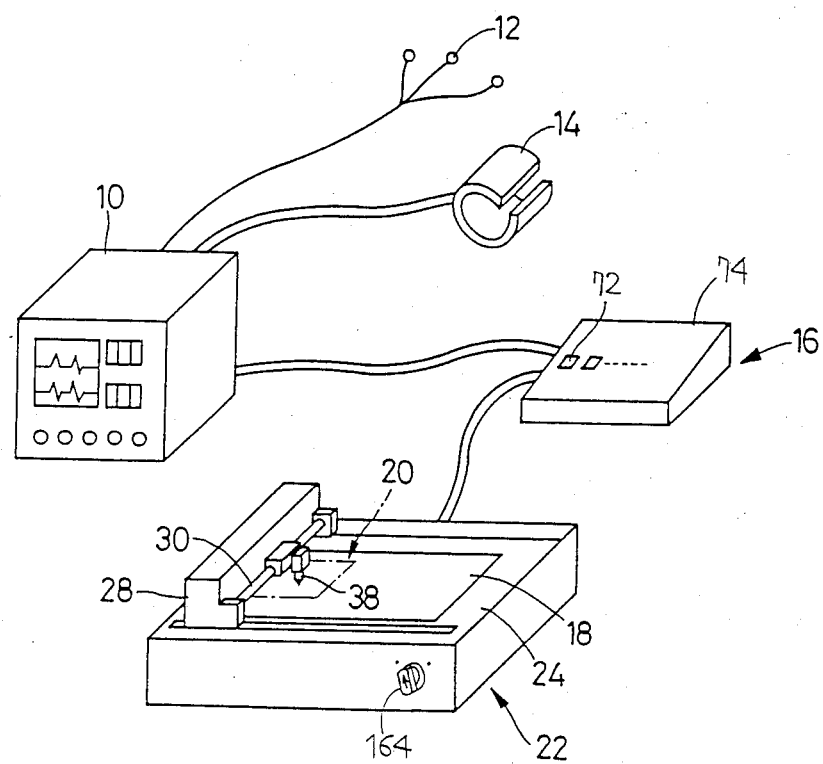
FIG. 43 is a view, corresponding to FIG. 1, showing a general arrangement of a further embodiment of the apparatus according to the present invention.
Figure 44:
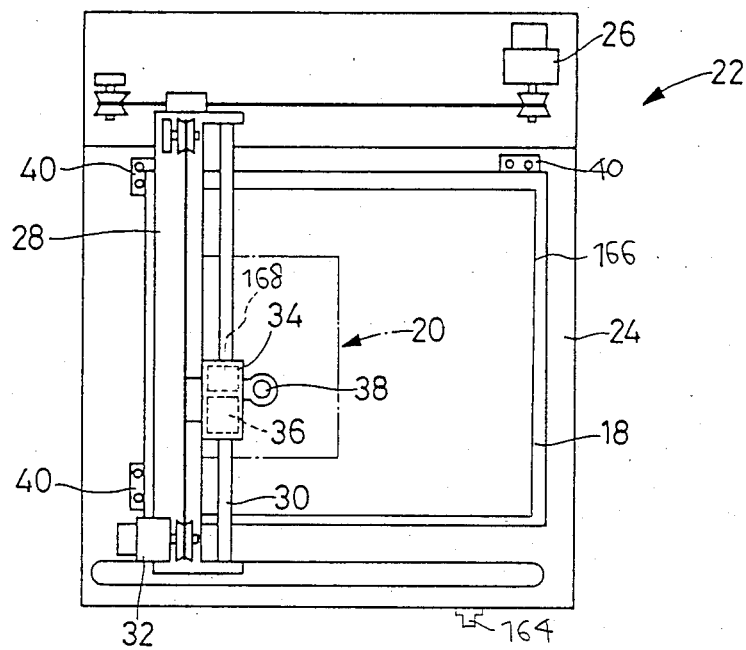
FIG. 44 is a view showing an X-Y plotter of the apparatus of FIG. 43.

Referring to FIGS. 43 and 44, there is provided a MODE switch 164 on a side wall of an X-Y plotter 22 of the present embodiment. The MODE switch 164 is utilized to switch the X-Y plotter 22 to an automatic compensation (AC) mode or a non-compensation (NC) mode. The AC mode is selected for avoiding possibly out-of-place recordings in a two dimensional chart area 20 due to shrinkage or expansion of the sheet 18. In the NC mode, the X-Y plotter 22 does not do such compensation.

In this embodiment, the record sheet 18 has frame lines 166 along its periphery, as shown in FIG. 44.

Figure 45:
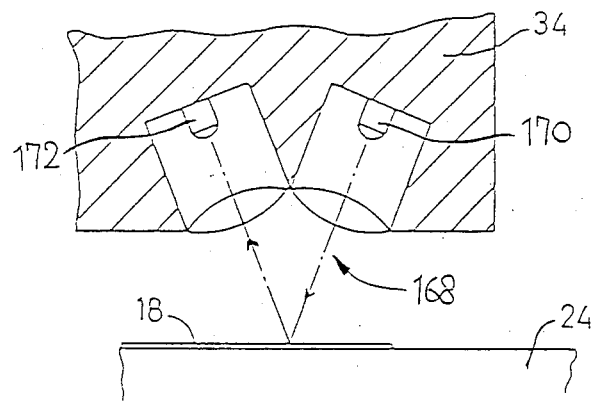
FIG. 45 is a view showing a sheet position sensor disposed on the X-Y plotter of FIG. 44.

In the under surface of a carriage 34, there is embedded a sheet sensor 168, as shown in FIG. 45, for detecting the frame lines 166 printed along the periphery of the record sheet 18. The sheet sensor 168 includes a light emitter 170 for emitting light beams toward the record sheet 18 and a light receiver 172 for receiving the light beams reflected by the sheet 18. The sheet sensor 168 detects the frame lines 166 based on alteration in intensity of the light beams received by the light receiver 172. The frame lines 166 includes two pairs of opposed lines, and an acutal distance between the opposed lines of each of the two pairs is measured by the sheet sensor 168.

Figure 46:
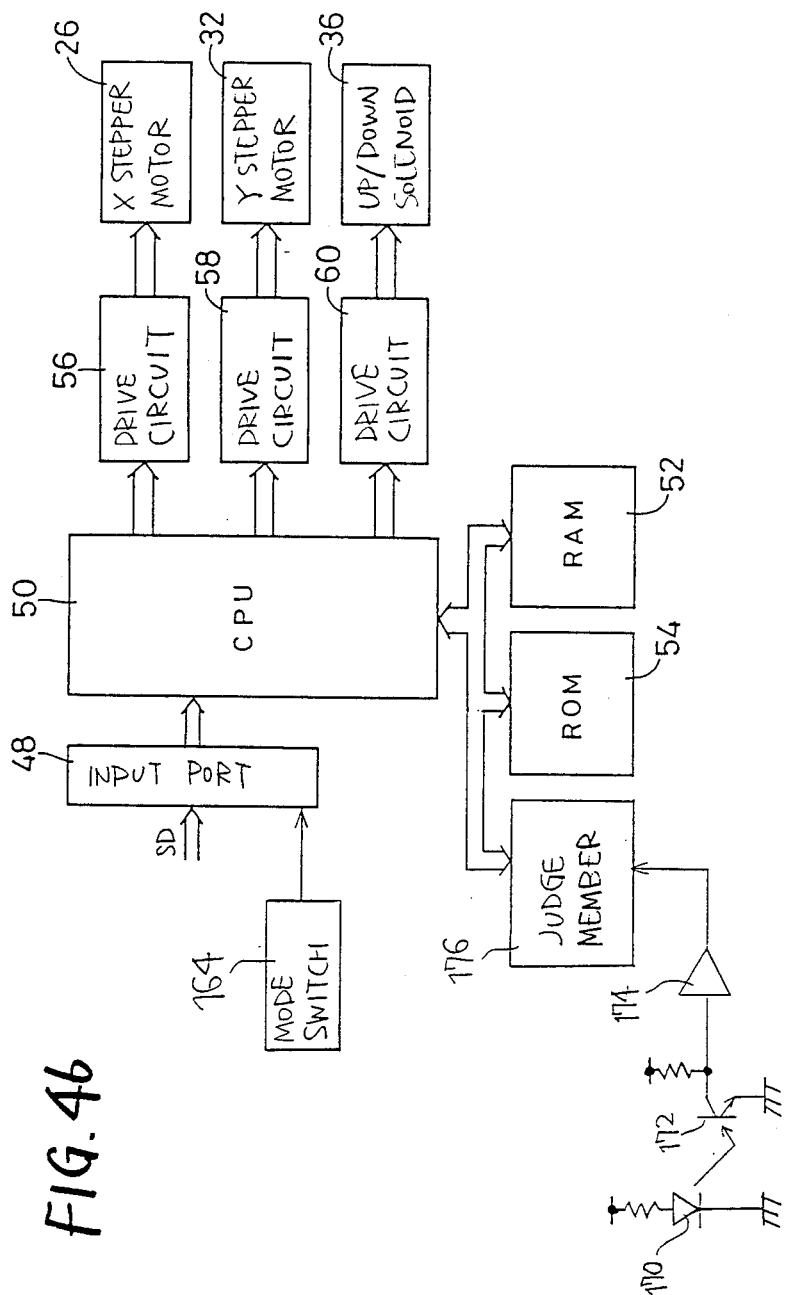
FIG. 46 is a block diagram, corresponding to FIG. 5, showing a control circuit used for the X-Y plotter.
Figure 47:
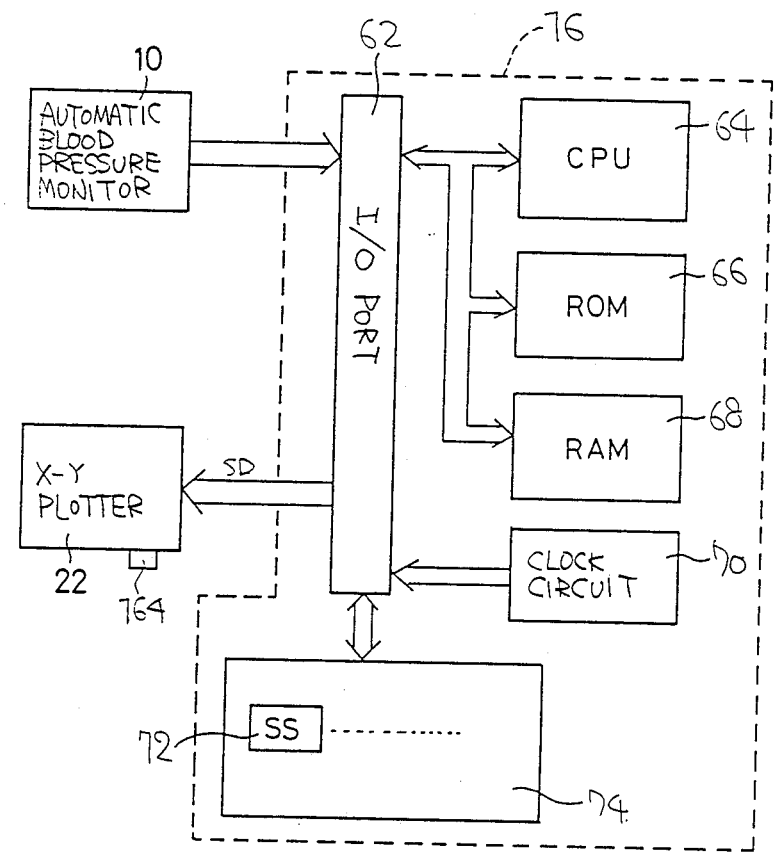
FIG. 47 is a block diagram, corresponding to FIG. 6, showing a construction of a control device of the apparatus of FIG. 43.

Referring to FIG. 46, there is illustrated a control circuit of the X-Y plotter 22. As shown in FIG. 47, an input port 48 receives from a control device 16 a record signal SD representative of the indicia to be recorded and its recording position in the two dimensional chart area 20. A signal from the light receiver 172 is supplied to a judge member 176 by way of an amplifier 174. The judge member 176 judges whether or not the intensity of the light beams received by the receiver 172 has decreased under a reference value. When the sheet sensor 168 passes over the frame line 166, the intensity of the light beams received decreases. Therefore, the judge member 176 detects the frame line 166, and supplies a signal indicating that the frame line 166 has been detected, to a CPU 50.

Figure 48:
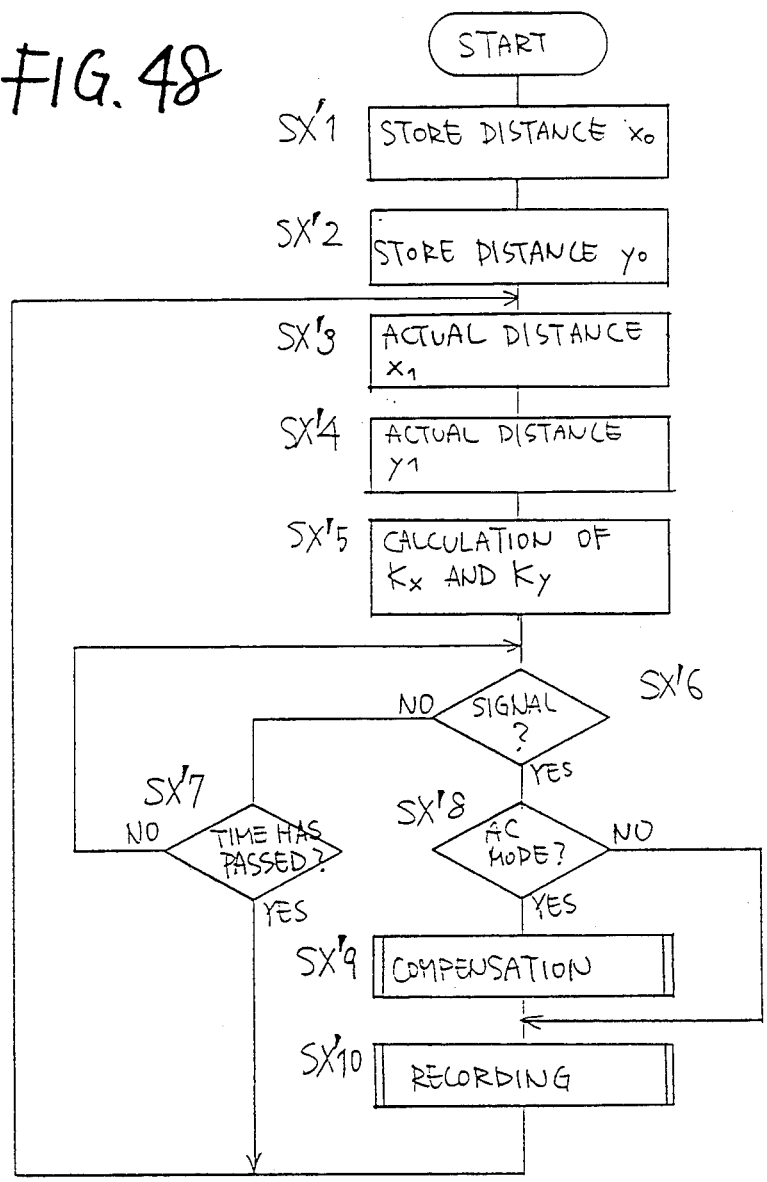
FIG. 48 is a flow chart showing the operation of the control circuit of FIG. 46.

Hereinafter, there will be described the control operation of the X-Y plotter 22 with reference to a flow chart shown in FIG. 48.

First, step SX'1 is executed to fetch a pre-stored distance x1 between two of the frame lines 166 which is perpendicular to an X direction (rightward-leftward direction as viewed in FIG. 44). Next, step SX'2 is executed to fetch a pre-stored distance y1 between two of the frame lines 166 which is perpendicular to a Y direction (upward-downward direction as viewed in FIG. 44). These values x1 and y1 are predetermined according to the print pattern of the record sheet 18, and pre-stored through operation of suitable keys, so as to be utilized as reference values. The recording position of the indicia corresponding to a record signal SD supplied from the control device 16 is determined on the supposition that the degree in shrinkage or expansion of the record sheet 18 is negligible, i.e., the distance values x1 and y1 as reference values has the same distances as the frame lines 166 of the record sheet 18 employed.

Step SX'2 is followed by step SX'3 wherein the carriage 34 is moved over the record sheet 18 from end to end in the X direction, and wherein are detected the positions of two of the frame lines 166 which are normal to the X direction. Therefore, at step SX'3, the actual distance x0 between the actual frame lines 166 is determined and stored. At the next step SX'4, the actual distance y0 between the other two of the frame lines 166 which are normal to the Y direction are determined and stored, similarly to step SX'3, that is, by means of moving the carriage 34 over the record sheet 18 from end to end in the Y direction.

Then, step SX'5 is executed to calculate compensation coefficients Kx and Ky fro the X and Y directions, respectively, according to the following expressions (1) and (2);

$$Kx = x1/x0 \quad (1)$$

$$Ky = x1/x0 \quad (2)$$

These coefficients Kx and Ky indicates a relation between the reference distance x1 and the actual distance x0, and a relation between the reference distances y1 and y0, respectively. In other words, these coefficients mean the degree in shrinkage or expansion of the record sheet 18. Therefore, steps SX'3, SX'4 and SX'5 serve as shrinkage/expansion determining means of this embodiment.

Step SX'5 is followed by step SX'6 to judge whether or not the input port 48 has received a record signal SD from the control device 16. In the case where the judgement at step SX'6 is negative (NO), step SX'6 is followed by step SX'7 to judge whether or not a predetermined time has elapsed after the last calculation of the coefficient Kx and Ky was made at step SX'5. The predetermined time is ten minutes, in this embodiment. If the judgement at step SX'7 is negative, step SX'6 is repeated to wait for passage of the time. And if the judgement at step SX'7 turns affirmative (YES), that is, after the predetermined time has passed, step SX'7 is backwardly followed by SX'3 to again execute step SX'3 and the following steps. If the judgement at step SX'6 turns from negative to affirmative during repetition of the steps SX'3 through SX'6 mentioned above, that is, if the input port 48 has received a record signal SD, step SX'6 is followed by step SX'8 to see whether or not the X-Y plotter 22 is currently placed in the AC (automatic compensation) mode. Based on the position of the MODE switch 164, it is judged whether or not drive signals to drive the carriage 34 should be compensated for avoiding out-of-place recordings on the record sheet 18 due to shrinkage or expansion of the sheet 18.

In the case where the judgement at step SX'8 is negative, that is, where the X-Y plotter 22 is positioned in the NC (non-compensation) mode, step SX'8 is followed by step SX'10 to conduct a recording. On the other hand, in the case where the judgement at step SX'8 is affirmative, step SX'8 is followed by step SX'9 to compensate drive signals to drive the carriage 34, and then at step SX'10 a recording operation is performed. More specifically described, at step SX'9, first is determined a traveling path of the carriage 34 for recording the indicia at its recording position according to a recording signal SD supplied from the control device 16. Second, an actual traveling path is obtained by multiplying the X and Y directions traveling distances for the traveling path of the carriage 34 by the coefficients Kx and Ky, respectively. Finally, are generated drive signals for driving the carriage 34 along the actual traveling path acquired. In this connection, drive signals to be supplied to a drive circuit 56 and a drive circuit 58 are modified or compensated for adjustment to the degree in shrinkage or expansion of the recording sheet 18. Therefore, step SX'9 corresponds to compensation means of this embodiment. At step SX'10, the drive signals modified at step SX'9 are supplied to the drive circuits 56 and 58 and a drive circuit 60 so as to effect an automatic recording using the pen 38.

As described hitherto, with the X-Y plotter 22 of this embodiment, the degree in shrinkage or expansion of the record sheet 18 is detected by way of obtaining the compensation coefficients by means of comparing the respective actual distances between two of the four frame lines 166 facing to each other and between the other two of the lines 166 facing to each other, with the predetermined reference distances. The pair of actual distances are measured by the sheet sensor 168. Drive signals supplied to the drive circuits 56 and 58 for driving an X stepper motor 26 and a Y stepper motor 32 are modified based on the compensation coefficients so as not to cause an out-of-place recording in the two dimensional chart area 20 in spite of expansion or shrinkage of the record sheet 18. As a result, the present embodiment is free from out-of-place recordings on the record sheet 18.

The present embodiment of the invention may take other arrangements.

For example, in the case where the difference between the degree in shrinkage or expansion of the sheet 18 in the X direction and that of the same in the Y direction is rather small, one of the compensation coefficients Kx and Ky may be used optionally for modifying the drive signals.

Further, the compensation coefficients Kx and Ky may be calculated for each record signal SD before the corresponding recording operation is performed, unlike the periodic calculation as described above.

Furthermore, for determining the degree in shrinkage or expansion of the record sheet 18, the peripheral edges of the sheet 18 may be utilized as markings to be detected by the sheet sensor 168, in place of the frame lines 166 printed along the peripheral edges. For utilizing the peripheral edges as markings, it is preferable to employ a color sheet for the recording sheet 18 or to use a dark support 24. This is because the peripheral edges are detected based on a difference in light intensity between the light beams reflected by the sheet 18 and those reflected by the support 24.

Since the requirement of the sheet sensor 168 is to measure a distance between a pair of predetermined positions spaced from each other on the record sheet 18, other markings may be utilized such as marks printed on the record sheet 18, in place of the frame lines 166 or the peripheral edges of the sheet 18.

The frame lines 166 may be printed on the record sheet 18 by means of the recording pen 38 driven by the X-Y plotter 22, unlike using the record sheet 18 preprinted with the frame lines 166.

Moreover, the sheet sensor 168 may be disposed on the support 24 such that the sensor 168 may detect the position of the peripheral edge of the sheet 18 facing the peripheral edge positioned by a positioning member 40.

EXAMPLE IX

There will be described a further embodiment according to the present invention.

Figure 49:
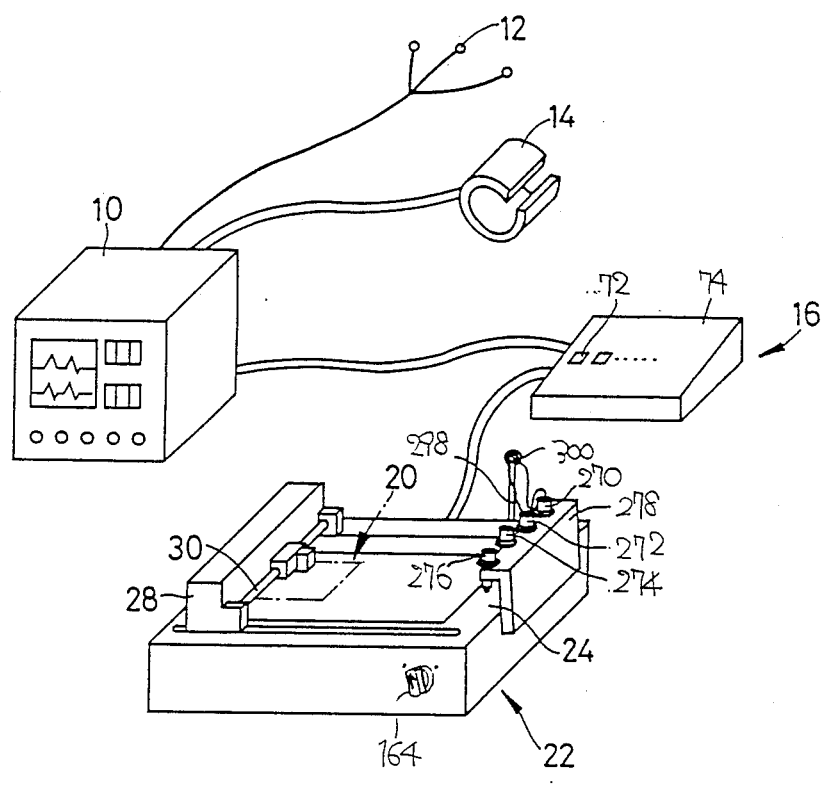
FIG. 49 is a view, corresponding to FIG. 1, showing a general arrangement of a still further embodiment of the apparatus.
Figure 50:
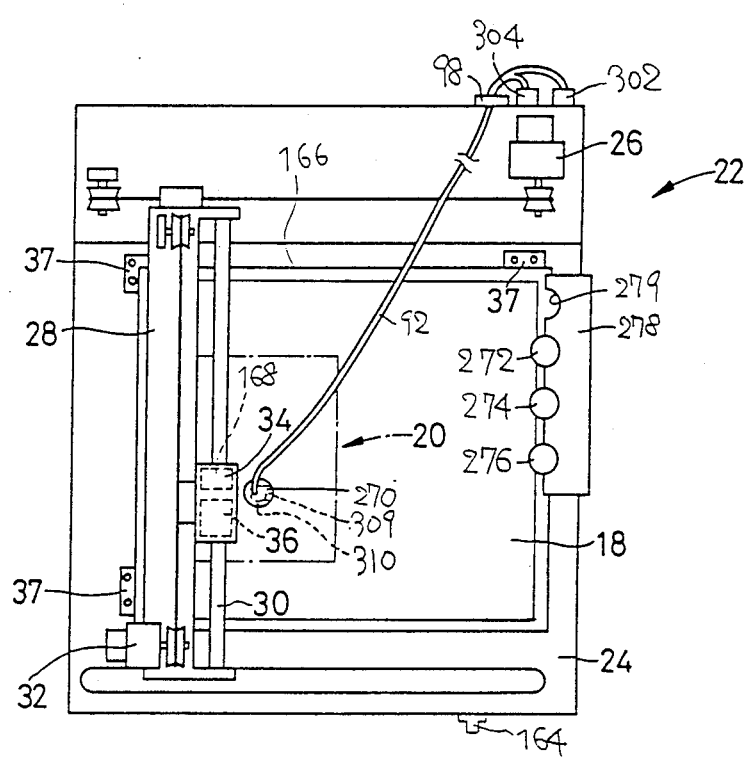
FIG. 50 is a view, corresponding to FIG. 3, showing an X-Y plotter of the apparatus of FIG. 49.

As illustrated in FIGS. 49 and 50, the instant embodiment of the invention includes a sensor pen 270 for detecting positions of frame lines 166 printed along four side edges of an anesthesia record sheet 18 so as to determine the degree of expansion or shrinkage of the sheet 18. The sensor pen 270 is employed in place of the sheet sensor 168 of the preceding embodiment of FIG. 43.

When not in use, the sensor pen 270, together with writing pens 272, 274 and 276, is held by a pen holder 278 which is disposed on an X-Y plotter 22 and has four circular recesses 279. The sensor pen 270 and writing pens 272, 274 and 276 are each moved over the record sheet 18 by a carraige 34 of the X-Y plotter 22 while being held by a support head (described below) formed with the carriage 34.

As shown in FIG. 51, the sensor pen 270 consists of a flanged cylinder 286, a cap 288, a shading cylinder 290, and an optical fiber cable 292. The flanged cylinder 286 has a first, a second, and a third annular flanges 280, 282, and 284. The cap 288 is engaged with an upper end of the flanged cylinder 286 so as to close an opening at the upper end of the flanged cylinder 286. The shading cylinder 290 is fixed to a lower end of the flanged cylinder 286. The optical fiber cable 292 passes through a hole (not shown) formed with the cap 288 and extends within the flanged cylinder 286 to the inside of the shading cylinder 290.

The first flange 280 of the flanged cylinder 286 has a slightly larger diameter than that of the recesses 279 of the pen holder 278, while the cylindrical portion of the flanged cylinder 286 has a slightly smaller diameter than that of the recesses 279. Therefore, when the sensor pen 270 is held by one of the recesses 279 of the pen holder 278, the lower surface of the first flange 280 is brought into abutment with respect to the upper surface of the pen holder 278.

The writing pens 272, 274 and 276 are constructed as the sensor pen 270, except that the pens 272, 274, and 276 are provided color inks in the flanged cylinder 286 from which the cap 288 removed in place of the optical fiber cable 292, and that each of the pens 272, 274 and 276 has in place of the shading cylinder 290 a pen tip to which the ink is supplied. The writing pens 272, 274 and 276 are held by the pen holder 278 as the sensor pen 270.

The colors of the inks for the writing pens 272, 274, and 276 are different from each other.

Referring to FIG. 52(b), the optical fiber cable 292 consists of a single first fiber 294 and six second fibers 296 arranged around the first fiber 294. The second fibers 296 are utilized for emitting light beams, while the first fiber is utilized for receiving light beams. The optical fiber cable 292 is disposed within the sensor pen 270 such that one end of the cable 292 is positioned a short distance away from an opening at the lower end of the shading cylinder 290, as shown in FIG. 52(a). The fiber cable 292 comes out of the sensor pen 270 and then passes through a ring 300 formed at the tip of a guide member 298 (FIGS. 49 and 50) the lower end of which is fixed to a side wall of the X-Y plotter 22. After passing through the ring 300, the cable 292 forks into the first fiber 294 and the second fibers 296 which are respectively connected to a light receiver 302 and a light emitter 304 at their respective ends other than the end positioned in the shading cylinder 290. The light emitter 304 is connected to a power source (not shown) which supplies the light emitter 304 with electric power, so as to enable the emitter 304 to emit light beams.

The carriage 34 of the X-Y plotter 22 is provided with a support head 310 having a circular recess 309 with a diameter slightly larger than that of the cylindrical portion of the flanged cylinder of each of the sensor and writing pens 270, 272, 274 and 276 and slightly smaller than that of the second and third flanges of the flanged cylinder of each. In the case where any one of the sensor and writing pens 270, 272, 274, and 276 is held by the support head 310 of the carriage 34, the cylindrical portion between the second and third flanges is catched or accommodated by the recess 309 of the support head 310. When each of the pens 270, 272, 274, and 276 is lifted up by the carriage, the lower surface of the third flange is brought into abutment on the upper surface of the support head 310. On the other hand, when each of the pens 270, 272, 274, and 276 is held by the carriage 34 and moved on the record sheet 18, the upper surface of the second flange is forcedly brought into abutment with respect to the lower surface of the support head 310. Thus, the sensor and writing pens 270, 272, 274, 276 are advantageously held by, and moved with, the carriage 34. The carriage 34 is moved in an X direction, a Y direction, and a vertical direction by an X stepper motor 26, a Y stepper motor 32, and an up/down solenoid 36 (FIG. 53), respectively.

Figure 54:
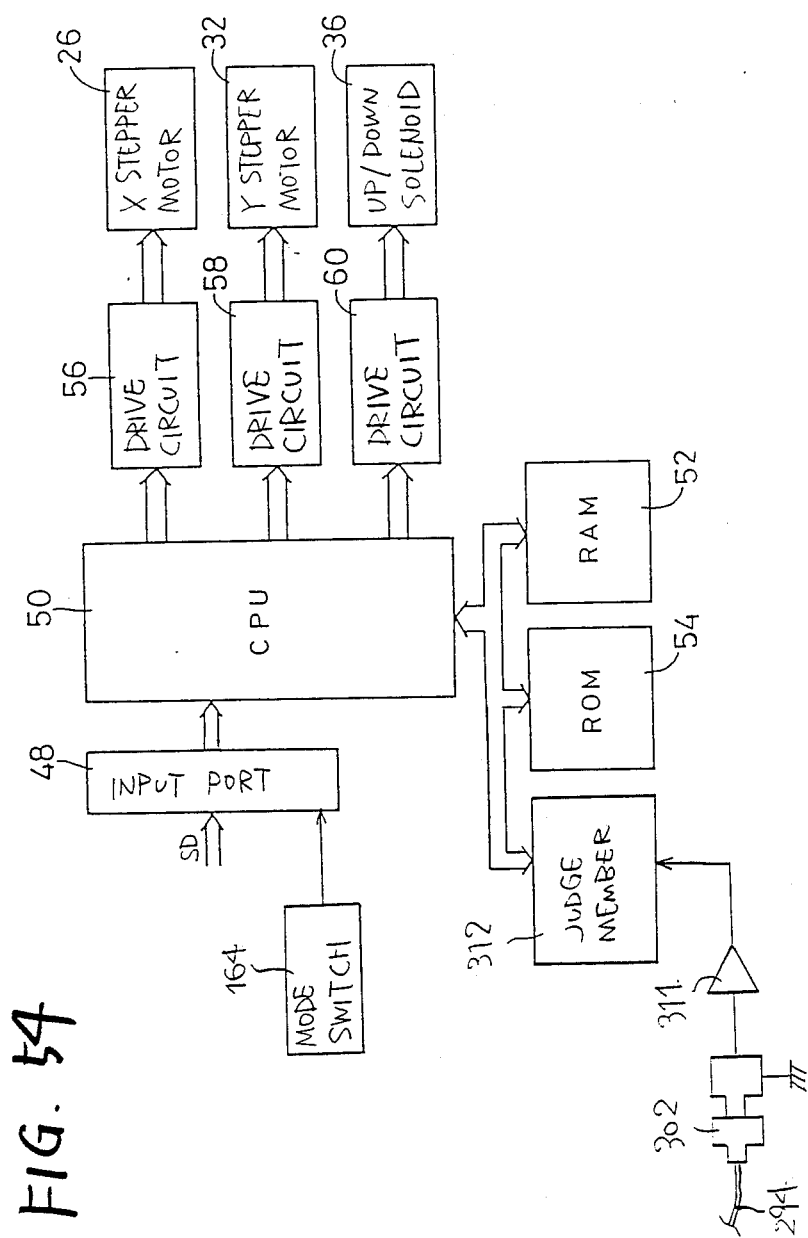
FIG. 54 is a block diagram, corresponding to FIG. 5, showing a control circuit for the X-Y plotter of FIG. 50.

In the X-Y plotter 22 constructed as described above, the degree of shrinkage or expansion of the record sheet 18 is detected prior to starting recording operation of indicias representative of items of living body information. As illustrated at arrows in FIG. 53, when the sensor pen 270 is moved on the record sheet 18, light beams are emitted from the second fibers 296 toward the record sheet 18 and the light beams reflected by the record sheet 18 are received by the first fiber 294. The light beams received by the first fiber 294 are transmitted to the light receiver 302. The information about the intensity of the light beams received by the light receiver 302 is supplied via an amplifier 311 to a judge member 312 of a control circuit for the X-Y plotter 22 shown (FIG. 54).

The distance "h" between the lower end of the shading cylinder 290 and the end surface of the optical fiber cable 292, i.e., between the fiber cable 292 and the record sheet 18 is determined depending upon the diameter of the first or second fiber 194 or 196, or other parameters.

As the sensor pen 270 is moved on the record sheet 18, the judge member 312 judges whether or not the intensity of the light beams received by the light receiver 302 is decreased under a predetermined reference value. When the sensor pen 270 passes one of the frame lines 166, the intensity of the light beams reflected is decreased by 30% in comparison with the intensity of the light beams reflected by non-printed, white portion of the sheet 18. Thus, the judge member 312 detects the frame lines 166, and generates signals representative of the presence of the frame lines 166. A CPU 50 receives the signals from the judge member 312, and calculates compensation coefficients that are utilized for compensating the shrinkage or expansion of the record sheet 18.

Figure 55:
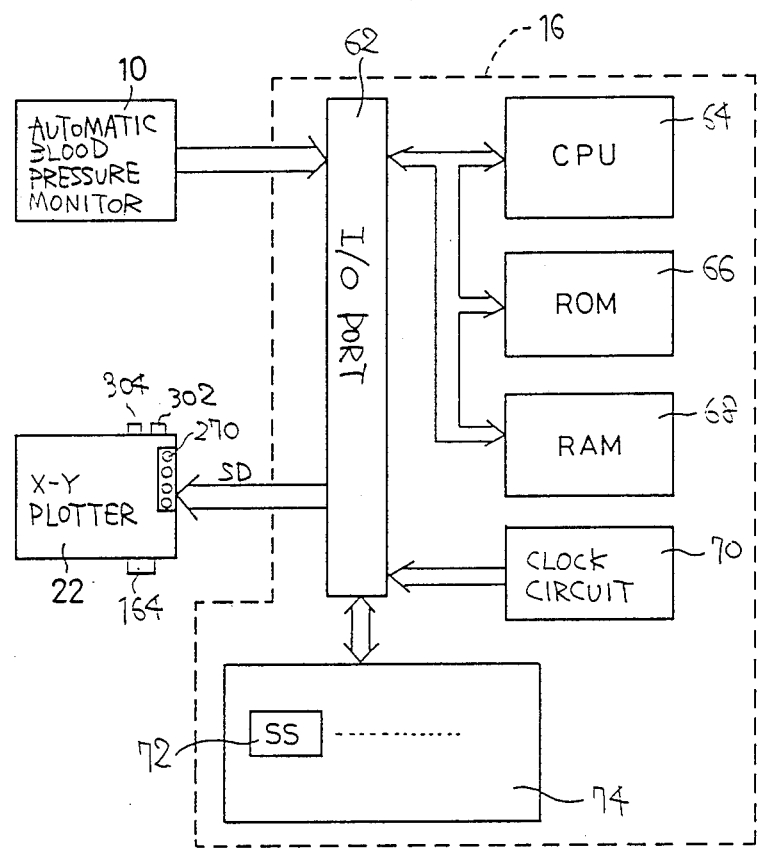
FIG. 55 is a block diagram, corresponding to FIG. 6, showing a construction of a control device in the apparatus of FIG. 49.

If a measurement of living body information is supplied from an automatic blood pressure monitor 10 (FIG. 49) to a control device 126, as shown in FIG. 55, and a record signal is supplied by the control device 16 to the CPU 50 in the control circuit of the X-Y plotter 22 through an input port 48 (FIG. 54), the CPU 50 generates respective drive signals to a drive circuit 56, a drive circuit 58, and a drive circuit 60.

Eventually, the X and Y stepper motors 26 and 32 and the up/down solenoid 36 move the carriage 34, according to the drive signals supplied from the CPU 50. The carriage 34 returns the sensor pen 270 held at the support head 310 thereof to the corresponding one of the recesses 279 of the pen holder 278. And the carriage 34 selects out of the writing pens 272, 274, and 276 held by the respective recesses 279 of the holder member 278 one writing pen corresponding to the indicia to be recorded, and holds the selected pen at the support head 310. In this connection, the writing pens 272, 274, 276 are used, for example, such that a red pen of the three pens is used for recording the indicias representative of the item of blood pressure, a yellow pen is used for breathing rate, and a blue pen is used for indicating administrations of a medicine.

In the case where a mode switch 164 is placed in an automatic compensation (AC) mode, the CPU 50 compensates drive signals to be supplied to the respective drive circuits 56, 58, and 60, by utilizing the compensation coefficients calculated. The drive circuits 56, 58, 60 drive the X stepper motor 26, the Y stepper motor 32 and the up/down solenoid 36 based on the drive signals compensated. Eventually, the carriage 34 is driven according to the compensated drive signals so as not to cause out-of-place recordings due to the expansion or shrinkage of the record sheet 18. Thus, the indicia representative of the selected item of living body information is accurately recorded at its recording position on the record sheet 18. It is also appreciated that the selected indicia is record with the corresponding one of the writing pens 272, 274, and 276 having a specified color.

The sensor pen 270 detects the degree of expansion or shrinkage of the record sheet 18 by means of measuring an actual distance between a pair of the frame lines 166 extending in the X direction and an actual distance between the other pair of the frame lines 166 extending in the Y direction. Based on the thus-obtained actual distances, the indicia representative of an item of living body information is recorded on the record sheet 18. Thus, the present embodiment of the invention provides the advantage of eliminating out-of-place recordings of the indicias on the record sheet 18 as the preceding embodiment previously described.

In this connection, it is appreciated that the present embodiment does not require the compensation means that is needed for the preceding embodiment for compensating a distance between the sensing means and the recording means. The sensor pen 270 (sensing means) and the writing pens 272, 274, and 276 (recording means) of the present embodiment are held at the same place, at the support head 310 of the carriage 34, when they are moved on the record sheet 18, such that the sensor pen 270 detects the frame lines 166 and the writing pens 272, 274, 276 records indicias. Therefore, a distance between the record sheet 18 and the sensing means is equal to a distance between the record sheet 18 and the recording means, and the compensation means required in the preceding embodiment is not needed in this embodiment.

Further, the present embodiment is advantageous in that the indicias are recorded with different colors by means of selectively using the plural writing pens (three pens 272, 274, and 276 in this embodiment) having different color inks. In other words, the indicia indicative of an item of living body information is recorded with a specified color by the corresponding one of the writing pens, and the indicia indicative of another item is recorded with another color by the corresponding writing pen.

While the present embodiment employs the optical fiber cable 292 including the single first fiber 294 and the six second fibers 296 which is adapted to detect the frame lines 166 having a single color, it is possible to employ an optical fiber cable 318 as shown in FIG. 56. The fiber cable 318 has three first fibers 314 (shadowed in the figure) for light reception and nine second fibers 316 for light emission. The three first fibers 314 includes a fiber 314R connected to a red-light sensing element (not shown), a fiber 314Y connected to a yellow-light sensing element (not shown), and a fiber 314B connected to a blue-light sensing element (not shown). The red-, yellow-, and blue-light sensing elements sense exclusively red, yellow, and blue light beams, respectively.

When the sensor pen 270 proved with the above-described optical fiber cable 318 is moved on the record sheet 18 provided with red, yellow, and blue frame lines, the nine second fibers 316 emit light beams against the record sheet 18 and the light beams reflected by the record sheet 18 are detected by the three light sensing elements by way of the first fibers 314R, 314Y, and 314B.

Where the sensor pen 270 passes a red frame line on the record sheet 18, the intensity of the blue light beams (a complementary color of red) received by the blue-light sensing element becomes lower by approximately 30% than that of the light beams reflected by the non-lined, white portion of the record sheet 18. This is because the blue light beams emitted from the second fibers 316 are partially absorbed by the red line when reflected, and the red-light sensing element receives the light beams that has been partially absorbed, through the first fiber 314R. The CPU 50 detects the position of the red line, as a result of the judgement that the intensity of the light beams received has decreased below a predetermined value in comparison with the pre-stored reference intensity for the non-printed, white portion of the record sheet 18. Similarly, the position of a yellow or a blue line is detected.

Therefore, in the instant form of the embodiment, any one of the red, yellow, and blue frame lines is detected when the sensor pen 270 passes it, because the corresponding fiber of the first fibers 314R, 314Y, and 314B receives the light beams that has been absorbed by approximately 30% of the light beams reflected by the white portion, and transmits them to the corresponding light sensing element. Thus, the position of a frame line is accurately detected, irrespective of the color of the frame line.

In the case where a frame line on the record sheet 18 has a color between any pair of the three colors (red, yellow, and blue), frame lines which are printed with any neutral tint between any pair of the three colors are detected by the sensing means of this form of the embodiment.

While the detected of the frame lines 166 by the sensor pen 170 is operated in the control circuit of the X-Y plotter 22 in the present embodiment, the detection of the frame lines 166 may be operated in the initiation operation of the control device 16, as the embodiment of the FIGS. 28, 29, 30, 31, and 32. In this case, the MODE switch 164 could be omitted, and the shrinkage or expansion of the record sheet 18 may be detected by detecting the presence of section lines (shown in FIG. 2) composing the two-dimensional chart area 20, in place of detecting the presence of the frame lines 166.

Since the actual location and size of the two-dimensional chart area 20 is automatically detected by the sensor pen 170 and other members in this mode of the embodiment, it is also possible to obtain the same advantages as the embodiment of the FIGS. 28–32 adding to the advantages of this embodiment above described, that is; reliable recordings of indicias on the record sheet 18, in spite of possibly out-of-place printings of the chart area 20 on the sheet 18, variation of the location of the chart area 20 on the record sheet 18 due to shrinkage or expansion of the sheet 18 onto the support 24, or the like.

EXAMPLE X

There will be described another embodiment of the invention.

The present embodiment includes an X-Y plotter 22 provided with a plurality of special keys 104 similar to those of the embodiment shown in FIGS. 14 and 15. Each of the special keys 104 is operated for recording the marking corresponding to an auxiliary item of living body information, not only in a two dimensional chart area 20 provided on an anesthesia record sheet 18 but also in an accessory area 120 on the same sheet 18. The title of a medicine administered to a living body or patient under anesthesia, the time at which the medicine was administered, the name of a medical treatment applied to the patient, the time at which the treatment was applied, and the like are required to be recorded as auxiliary items of living body information during a surgical operation.

As illustrated in broken lines in FIG. 57, the two dimensional chart area 20 on the record sheet 18 includes a plurality of recording tracks 320 along an axis of abscissa (time axis) 78 thereof. When one of the special keys 104 is operated, the corresponding marking is recorded in one of the plural recording tracks 320 at a position corresponding to the time at which the special key 104 is operated. The plural recording tracks 320 of this embodiment consists of three tracks.

The present embodiment also has a plotter control device 102 similar to that of the embodiment of FIG. 14. The plotter control device 102 interrupts the X-Y plotter 22 while the plotter 22 drives a carriage 34 based on a record signal supplied from a control device 16 so as to record an indicia representative of an item of living body information in the chart area 20. The interruption by the plotter control device 102 is executed periodically, for example, an intervals of 10 ms.

The above-indicated interruption routine as shown in FIG. 58 consists of the steps described below. At step ST'1, it is judged whether or not any one of the special keys 104 has been operated for recording the corresponding marking. If the judgement at step ST'1 is affirmative (YES), step ST'1 is followed by step ST'2 wherein the time at which the selected special key 104 is operated is determined based on the time represented by a signal supplied from the control device 16. Also, the position at which the selected marking is to be recorded is determined, based on the above-identified time, in a first (upper) recording track 320a of the three tracks 320 along the time axis 78 of the chart area 20.

At the step ST'3, it is judged whether or not a marking has been already recorded at the position determined at step ST'1. At the beginning of recording operation, no marking has been recorded yet. Therefore, the judgement at step ST'3 is negative (NO). And at step ST'4, the CPU 50 of the plotter control device 102 generates drive signals so as to drive the carriage 34, and the selected marking (e.g., the figure "1" shown in FIG. 57), is recorded at the determined position in the first track 320a. At the same time, the figure "1" is recorded in the accessory area 120 at a position corresponding to the time at which the special key 104 is operated. Then, step ST'4 is followed by step ST'1.

If, at step ST'1, one of the special keys 104 is again operated after the above-indicated operation of the special key 104, a position at which the marking corresponding to the currently operated special key 104 is to be recorded is determined in the first track 220a, at step ST'2. And at step ST'3 it is judged whether or not a marking has been already recorded at the position determined at step ST'2.

In the case where the judgement at step ST'3 is affirmative, that is, if it is judged that the marking corresponding to the currently selected special key 104 completely or partially overlaps the marking which has been recorded in the first track 320a, step ST'3 is followed by step ST'5. The CPU 50 makes the judgement at step ST'3 based on a difference between the respective two times at which the two special key operations are conducted.

At step ST'5, it is judged whether or not a marking has been already recorded in a second (middle) track 320b of the three tracks 320 at a position corresponding to the time at which the special key 104 is operated. In the case where the judgement at step ST'5 is negative, step ST'5 is followed by step ST'6 wherein the current marking, for example, the figure "2" shown in FIG. 57, is recorded at the determined position in the second track 320b.

Further, if one of the special keys 104 corresponding to a marking "3" shown in the FIG. 57 is operated just after the above-indicated recording of the figure "2" in the second track 320b, the judgement is affirmative in the step ST'3 and also the step ST'5. It is because that the elapsed time between the time when the marking "3" is inputting by the special key 104 and the time when the marking "1" or "2" is inputting, is not enough for the marking "3" not to overlap the previous markings "1" and "2". Subsequently, step ST'7 is executed to record the marking "3" in the corresponding place in the third track 320c, where no other marking is recorded.

Moreover, if succeeding markings "4" and "5" (shown in the FIG. 57) are input by the corresponding special keys 104, after enough long time not to overlap the previous marking "1" in the case of recording of the succeeding markings "4" and "5" in the first track 320a, the judgement in the step ST'3 is negative so that the markings "4" and "5" are recorded in the first track 320a, respectively.

As described hitherto, in the present embodiment, the markings corresponding to the respective special keys 104 which have been operated in a rather short time are recorded in the respective, different recording tracks 220. As a result, the markings are prevented from overlappings of each other when being recorded, aand they are easily read by the operator or medical worker.

The number of the recording tracks 220 is limited in order that the recorded markings can be easily related to the time axis 78 and the recorded indicias in the two dimensional chart area 20, and so that the tracks 220 would not invade other recording areas for other items. The recording tracks 220 of the present embodiment consists of three tracks 220a, 220b, and 220c.

While the axis of abscissa 78 of the chart area 20 is utilized for the time axis and the recording tracks 220 are provided along the axis of abscissa 78, it is possible to utilized the axis of ordinate 76 for the time axis and provide the recording tracks 220 along the axis of ordinate 78, in this embodiment.

What is claimed is:

1. An apparatus for effecting automatic repetitive detection of at least one item of living-subject information selected from a plurality of items of information on a living subject, and for automatically recording the detected living-subject information in a predetermined two-dimensional chart area provided on a recording medium, by means of recording respective indicia representative of said living-subject information, at respective recording positions in the chart area, which correspond to times of detection of the living-subject information, comprising:

a sensing device for detecting said living-subject information;

a recording device including a support means for supporting said recording medium so as to permit manual recording of auxiliary information other than said living-subject information on the recording medium, and further including recording means movable relative to said recording medium for recording said indicia in said chart area; and control means, responsive to said sensing device, for determining the recording positions of said indicia based on the detected living-subject information and said times of detection of said living-subject information, and for controlling said recording device so as to record said indicia at the determined recording positions in said chart area.

2. An apparatus according to claim 1, further comprising a clock circuit which generates time signals representative of said times of detection, said control means determining said recording positions based on said times signals and said living-subject information.

3. An apparatus according to claim 2, wherein each of said recording positions on said indicia is determined along a first and a second chart axis of said two-dimensional chart area, said times of detection and a value of said detected living-subject information being taken along said first and second chart axes, respectively, said control means including alarm means for producing an alarm signal when the recording position which has been determined last is located outside said chart area in a direction along said first chart axis.

4. An apparatus according to claim 1, wherein said control means includes a detector for producing a signal indicative of the presence or absence of said recording medium on said support, and means for inhibiting the recording of said indicia while said signal indicates the absence of said recording medium, and permitting the recording of said indicia while said signal indicates the presence of said recording medium.

5. An apparatus according to claim 1, further comprising input means for specifying a location and a size of said two-dimensional chart area, by means of tracing a periphery of said chart area, and memory means for storing area data representative of said location and size of said chart area entered through said input means, said control means determining the location and size of said chart area based on said area data stored in said memory means, and determining said recording positions of said indicia in the determined chart area, based on said living-subject information and said times of detection.

6. An apparatus according to claim 5, wherein said input means comprises means for generating position signals indicative of operator-controlled movements of said recording means among said periphery of said charge area, said control means determining said area data based on said position signals.

7. An apparatus according to claim 5, wherein said input means comprises operator-controlled means for moving said recording means relative to said recording medium along said periphery of said chart area, said area data being stored into said memory means as said operator-controlled means is operated to move said recording means along said periphery of said chart area.

8. An apparatus according to claim 5, wherein each of said recording positions of said indicia is determined along a first and a second chart axis of said two-dimensional chart area, said times of detection and a value of said detected living-subject information being taken along said first and second chart axes, respectively, said input means comprising operator-controlled means for specifying maximum values that are taken along said first and second chart axes.

9. An apparatus according to claim 5, wherein said control means comprises means for moving said recording means according to said area data stored in said memory means, to permit verification of said location and size of the specified chart area through movements of said recording means.

10. An apparatus according to claim 1, further comprising input means for selecting one of a plurality of markings indicative of items of said auxiliary information, and wherein said control means is responsive to said input means, for activating said recording device to record the selected marking in said chart area at a position corresponding to time of recording of said selected marking, and to record said selected marking at a corresponding position in an auxliary recording area provided on said recording medium for recording said auxiliary information.

11. An apparatus according to claim 10, wherein said two dimensional chart area includes a plurality of recording tracks provided along one of adjacent two sides thereof, said control means judging whether or not a marking has been already recorded at a position at which said selected marking is to be recorded, in one of said plurality of recording tracks, and recording the selected marking at said position if said judgement is negative, but recording the selected marking at a position corresponding to said time in another recording track of said plural recording tracks if said judgement is affirmative.

12. An apparatus according to claim 1, further comprising a display device for indicating the living-subject information detected by said sensing device, and operator-controlled means for inhibiting said recording device from recording the indicia representative of the living-subject information indicated on said display device, in said chart area.

13. An apparatus according to claim 12, further comprising another operator-controlled means for activating said sensing device to re-detect the selected item of living-subject information whose previous value has been indicated on said display device, said another operator-controlled means being operable after the operation of said recording device is inhibited by activation of said operator-controlled means.

14. An apparatus according to claim 1, further comprising judging means for checking if a value of the living-subject information detected by said sensing device falls within a predetermined valid range, and inhibiting means for inhibiting said recording device from recording the indicia representative of the detected living-subject information if said judging means judges that the detected value does not fall within said predetermined valid range.

15. An apparatus according to claim 14, further comprising operator-controlled means for activating said sensing device to re-detect the selected item of living-subject information, said operator-controlled means being operable after said inhibiting means is activated to inhibit the operation of said recording device.

16. An apparatus according to claim 1, further comprising sensing means for detecting a location of said predetermined chart area on said recording medium on said support, and memory means for storing position data representative of the detected location of said chart area, said control means determining said recording positions of said indicia in said chart area, based on the detected living-subject information, said times of detection and said position data stored in said memory means.

17. An apparatus according to claim 16, wherein said recording device further includes a carriage capable of holding said recording means and movable relative to said recording medium, and wherein said sensing means includes a photosensor which is disposed on said carriage and detects light reflected by said recording medium, said sensing means detecting the location of said predetermined chart area on the recording medium by means of said photosensor.

18. An apparatus according to claim 16, wherein said recording device further includes a carriage movable relative to said recording medium in an X direction and a Y direction normal to said X direction, and a holder member fixed to said support means and capable of holding a plurality of said recording means, said carriage being capable of selectively fetching one of said plural recording means from said holder member and returning said one recording means to said holder member, and wherein said sensing means includes a light receiving element and an optical fiber which is connected to said light receiving element at one end thereof and fixed at the other end thereof to a lower end portion of one of said plural recording means, said optical fiber receiving light reflected by said recording medium and transmitting said light to said light receiving element.

19. An apparatus according to claim 1, further comprising: memory means for storing said detected living-subject information and position data representative of said recording positions of the corresponding indicia which have been recorded in said chart area; operator-controlled means for commanding re-recording of said corresponding indicia; and re-recording control means, responsive to said operator-controlled means, for activating said recording device according to said living-subject information and said position data stored in said memory means, for re-recording said corresponding indicia.

20. An apparatus according to claim 1, wherein said recording device is an X-Y plotter including drive means for moving said recording means relative to said recording medium on said support means, along an X axis and a Y axis in a plane parallel to a recording surface of said recording medium, said apparatus further comprising: a detector means for detecting a manual-recording state in which said manual recording of said auxiliary information on said recording medium is permitted, said detector means generating a manual-recording signal when said manual-recording state is detected; and drive control means, responsive to said manual-recording signal, for controlling said drive means so as to retract said recording means to a predetermined retracted position which is selected so that said recording means located at said retracted position will not interfere with a hand of a person who achieves said manual recording of said auxiliary information, said recording means being held at said retracted position while said manual-recording signal is present.

21. An apparatus according to claim 20, wherein said detector means includes a pen holder for accommodating a marker used for effecting said manual-recording of said auxiliary information, and a sensor means for sensing said marker accommodated in said pen holder.

22. An apparatus according to claim 20, wherein said detector means includes a photoelectric sensor array of reflection type for sensing the hand of said person positioned above said support means of said recording device.

23. An apparatus according to claim 1, further comprising: sensor means for detecting positions of at least two markings provided on said recording medium such that said markings are spaced apart from each other by a predetermined nominal distance from each other in a plane parallel to said recording medium; determining means for determining an actual distance between said two markings based on the detected positions thereof, and determining a ratio of said determined actual distance to said nominal distance, which indicates a degree of shrinkage or expansion of said recording medium; and compensation means for modifying drive signals to be applied to drive means to operate said recording means according to said ratio, so as to compensate said recording positions of said indicia for a variation of said actual distance from said nominal distance.

24. An apparatus according to claim 23, wherein said determining means determines said ratio before said recording device records said indicia, or at predetermined time intervals during an entire period of recording of said indicia on said recording medium.

25. An apparatus according to claim 23, wherein said chart area is substantially rectangular and said at least two markings include a pair of first markings which are spaced from each other by a first nominal distance along a first axis parallel to one of two adjacent sides of said chart area, and a pair of second markings which are spaced from each other by a second nominal distance along a second axis parallel to the other of said two adjacent sides, said sensor means detecting a first actual distance between said first markings, and a second actual distance between said second markings, said determining means determining a first ratio of said first actual distance to said first nominal distance, and a second ratio of said second actual distance to said second nominal distance, said compensation means modifying said drive signals according to the determined first and second ratios, to compensate said recording positions of said indicia for variations of said first and second actual distances from said first and second nominal distances, respectively.

26. An apparatus according to claim 1, wherein said plurality of items of information on a living body comprise blood pressure, heart rate, respiration rate, body temperature, concentration of an anesthetic contained in the expiration, and degree of saturation of oxygen in the blood.

* * * * *